United States Patent
Wang et al.

(10) Patent No.: US 11,390,679 B2
(45) Date of Patent: Jul. 19, 2022

(54) ANTI-LAG-3 ANTIBODIES AND USES THEREOF

(71) Applicant: Phanes Therapeutics, Inc., San Diego, CA (US)

(72) Inventors: Minghan Wang, San Diego, CA (US); Hui Zou, Dallas, TX (US); Haiqun Jia, San Diego, CA (US)

(73) Assignee: Phanes Therapeutics, Inc., San Diego, CA (US)

(*) Notice: Subject to any disclaimer, the term of this patent is extended or adjusted under 35 U.S.C. 154(b) by 180 days.

(21) Appl. No.: 16/639,827

(22) PCT Filed: Aug. 28, 2018

(86) PCT No.: PCT/US2018/048221
§ 371 (c)(1),
(2) Date: Feb. 18, 2020

(87) PCT Pub. No.: WO2019/046225
PCT Pub. Date: Mar. 7, 2019

(65) Prior Publication Data
US 2021/0032331 A1    Feb. 4, 2021

Related U.S. Application Data

(60) Provisional application No. 62/626,310, filed on Feb. 5, 2018, provisional application No. 62/588,475, filed on Nov. 20, 2017, provisional application No. 62/551,927, filed on Aug. 30, 2017.

(51) Int. Cl.
*G01N 33/577* (2006.01)
*C07K 16/28* (2006.01)

(52) U.S. Cl.
CPC ....... *C07K 16/2803* (2013.01); *G01N 33/577* (2013.01); *C07K 2317/24* (2013.01); *C07K 2317/31* (2013.01); *C07K 2317/565* (2013.01)

(58) Field of Classification Search
CPC .............. G01N 33/577; C07K 2317/56; C07K 2317/565; C07K 16/2896
USPC ........................................... 424/133.1, 136.1
See application file for complete search history.

(56) References Cited

U.S. PATENT DOCUMENTS

| | | | |
|---|---|---|---|
| 5,559,019 | A | 9/1996 | Gui et al. |
| 2009/0280128 | A1 | 11/2009 | Kamogawa et al. |
| 2010/0233183 | A1 | 9/2010 | Triebel et al. |
| 2011/0150892 | A1* | 6/2011 | Thudium ................ A61P 31/18 424/142.1 |
| 2016/0194402 | A1 | 7/2016 | Van Eenennaam et al. |
| 2016/0280771 | A1 | 9/2016 | Pincus et al. |

FOREIGN PATENT DOCUMENTS

| | | |
|---|---|---|
| CN | 104059151 A | 9/2014 |
| WO | 1995030750 A2 | 11/1995 |
| WO | 2008132601 A1 | 11/2008 |
| WO | 2010019570 A2 | 2/2010 |
| WO | 2014008218 A1 | 1/2014 |
| WO | 2014140180 A1 | 9/2014 |
| WO | 2015042246 A1 | 3/2015 |
| WO | 2015116539 A1 | 8/2015 |
| WO | 2015138920 A1 | 9/2015 |
| WO | 2015200119 A1 | 12/2015 |
| WO | 2016126858 A2 | 8/2016 |
| WO | 2016200782 A1 | 12/2016 |
| WO | 2017015560 A2 | 1/2017 |
| WO | 2017019894 A1 | 2/2017 |
| WO | 2017037203 A1 | 3/2017 |
| WO | 2017062888 A1 | 4/2017 |

OTHER PUBLICATIONS

Triebel F, et al. (The Journal of Experimental Medicine 171 (5): 1393-405 ((May 1990)).*
Kim SS et al., Veterinary Immunology and Immunopathology. 133 (1): 72-9 (Jan. 2010)).*
International Search Report and Written Opinion dated Dec. 18, 2018 in International Application No. PCT/US2018/048221.
Baixeras et al., "Characterization of the Lymphocyte Activation Gene 3-Encoded Protein. A New Ligand for Human Leukocyte Antigen Class II Antigens" J. Exp. Med, vol. 176, Aug. 1992, pp. 327-337.
Hahn et al., "The future of immune checkpoint cancer therapy after PD-1 and CTLA-4" Immunotherapy, vol. 9(8), pp. 681-692 (2017).
Huang et al., "Role of LAG-3 in Regulatory T Cells" Immunity, vol. 21, pp. 503-513, Oct. 2004.
Huard et al., "Cellular expression and tissue distribution of the human LAG-3-Encoded Protein, an MHC class II Ligand" Immunogenetics, vol. 39, pp. 213-217, 1994.
Huard et al., "Characterization of the major histocomjpatibility complex class II binding site on LAG-3 protein" Proc. Natl. Acad. Sit. USA, vol. 94, pp. 5744-5749, May 1997.
Kisielow et al., "Expression of lymphocyte activation gene 3 (LAG-3) on B cells is induced by T cells" Eur. J. Immunol, vol. 35, pp. 2081-2088, 2005.
Liang et al., "Regulatory T Cells Inhibit Dendritic Cells by Lymphocyte Activation Gene-3 Engagement of MHC Class II" The Journal of Immunology, vol. 180, pp. 5916-5926, 2008.
Triebel et al., "LAG-3, a Novel Lymphocyte Activation Gene Closely Related to CD4," J. Exp. Med., vol. 171, pp. 1393-1405, May 1990.

(Continued)

*Primary Examiner* — Lynn A Bristol
(74) *Attorney, Agent, or Firm* — Ice Miller LLP

(57) ABSTRACT

Anti-LAG-3 antibodies and antigen-binding fragments thereof are described. Also described are nucleic acids encoding the antibodies, compositions comprising the antibodies, and methods of producing the antibodies and using the antibodies for treating or preventing diseases such as cancer, an inflammatory disease, an autoimmune disease, type 1 diabetes, and/or infectious diseases.

17 Claims, 14 Drawing Sheets
Specification includes a Sequence Listing.

(56) References Cited

OTHER PUBLICATIONS

Workman et al., "LAG-3 Regulates Plasmacytoid Dendritic Cell Homeostasis" J. Immunol, vol. 182(4), pp. 1885-1891 (2009).
Xu et al., "LSECtin Expressed on Melanoma Cells Promotes Tumor Progression by Inhibiting Antitumor T-cell Reponses" Cancer Res. vol. 74(13), pp. 3418-3428, Jul. 1, 2014.
Zhang et al., "LAG-3 limits regulatory T cell proliferation and function in autoimmune diabetes" Sci Immunol, vol. 2 (9), pp. 1-24, Mar. 31, 2017.
Sierro et al., "The CD4-like molecule LAG-3, biology and therapeutic applications," Expert Opin. Ther. Targets, vol. 15 (1), pp. 91-101 (2011).

\* cited by examiner

SEQUENCE LISTING

<160> NUMBER OF SEQ ID NOS: 210

<210> SEQ ID NO 1
<211> LENGTH: 120
<212> TYPE: PRT
<213> ORGANISM: Artificial Sequence
<220> FEATURE:
<223> OTHER INFORMATION: B1 Heavy Chain Variable Region

<400> SEQUENCE: 1

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Asp Tyr Ser Gly Ile Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Glu Asp Thr Ala Thr Tyr Tyr Cys
                85                  90                  95

Ala Arg Glu Asp His Tyr Asp Leu Ala Trp Phe Ala Tyr Trp Gly Gln
            100                 105                 110

Gly Thr Leu Val Thr Val Ser Ala
        115                 120

<210> SEQ ID NO 2
<211> LENGTH: 107
<212> TYPE: PRT
<213> ORGANISM: Artificial Sequence
<220> FEATURE:
<223> OTHER INFORMATION: B1 Light Chain Variable Region

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys His Gln Tyr Ser Asn Arg Pro Pro
                85                  90                  95

Thr Phe Gly Gly Gly Thr Lys Leu Glu Ile Lys
            100                 105

<210> SEQ ID NO 3
<211> LENGTH: 120
<212> TYPE: PRT
<213> ORGANISM: Artificial Sequence
<220> FEATURE:
<223> OTHER INFORMATION: B2 Heavy Chain Variable Region

<400> SEQUENCE: 3

Gln Val His Leu Gln Gln Ser Gly Pro Gln Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Arg Pro Gly Gln Gly Leu Glu Trp Ile
        35                  40                  45

Gly Trp Ile Phe Pro Gly Ser Gly Ser Thr Tyr Tyr Asn Glu Lys Phe
    50                  55                  60

Lys Gly Lys Ala Thr Leu Thr Val Asp Lys Ser Ser Ser Thr Ala Tyr
65                  70                  75                  80

Met Leu Leu Ser Ser Leu Thr Ser Glu Asp Ser Ala Val Tyr Phe Cys
                85                  90                  95

Val Arg Ile His Phe Asp Tyr Asp Trp Phe Asp Val Trp Gly Thr
            100                 105                 110

Gly Thr Thr Val Thr Val Ser Ser
        115                 120

<210> SEQ ID NO 4
<211> LENGTH: 112
<212> TYPE: PRT
<213> ORGANISM: Artificial Sequence
<220> FEATURE:
<223> OTHER INFORMATION: B2 Light Chain Variable Region

<400> SEQUENCE: 4

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Phe Tyr Trp Tyr Leu Gln Lys Pro Gly Gln Ser
        35                  40                  45

Pro Asn Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Val Tyr Tyr Cys Phe Gln Gly
                85                  90                  95

Thr His Val Pro Tyr Thr Phe Gly Gly Gly Thr Lys Leu Glu Ile Lys
            100                 105                 110
```

<210> SEQ ID NO 5
<211> LENGTH: 120
<212> TYPE: PRT
<213> ORGANISM: Artificial Sequence
<220> FEATURE:
<223> OTHER INFORMATION: B3 Heavy Chain Variable Region

<400> SEQUENCE: 5

```
Gln Val Gln Leu Gln Gln Pro Gly Ala Glu Leu Leu Lys Pro Gly Ala
1               5                   10                  15

Ser Val Lys Met Ser Cys Lys Ala Ser Gly Tyr Thr Phe Thr Ser Tyr
            20                  25                  30

Asp Ile His Trp Leu Lys Gln Thr Pro Gly Gln Gly Leu Glu Trp Ile
        35                  40                  45

Gly Ala Ile Tyr Pro Glu Asn Gly Asp Ser Ser Tyr Ser Gln Lys Phe
    50                  55                  60

Lys Asp Lys Ala Thr Leu Thr Ala Asp Lys Ser Ser Asn Thr Ala Tyr
65                  70                  75                  80

Ile His Leu Ser Ser Leu Thr Ser Glu Asp Ser Ala Val Tyr Tyr Cys
                85                  90                  95

Ala Arg Gly Gly Tyr Tyr Asp Tyr Val Trp Phe Pro Tyr Trp Gly Gln
            100                 105                 110

Gly Thr Leu Val Thr Val Ser Ala
        115                 120
```

<210> SEQ ID NO 6
<211> LENGTH: 112
<212> TYPE: PRT
<213> ORGANISM: Artificial Sequence
<220> FEATURE:
<223> OTHER INFORMATION: B3 Light Chain Variable Region

<400> SEQUENCE: 6

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu Tyr Ser
            20                  25                  30
```

```
Asn Gly Tyr Thr Tyr Leu Glu Trp Tyr Leu Gln Lys Pro Gly Gln Ser
            35                  40                  45

Pro Lys Leu Leu Ile Tyr Gly Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ser Glu Asp Met Gly Val Tyr Tyr Cys Phe Gln Gly
                 85                  90                  95

Thr His Val Pro Leu Thr Phe Gly Ala Gly Thr Lys Leu Glu Leu Lys
            100                 105                 110
```

<210> SEQ ID NO 7
<211> LENGTH: 120
<212> TYPE: PRT
<213> ORGANISM: Artificial Sequence
<220> FEATURE:
<223> OTHER INFORMATION: B4 Heavy Chain Variable Region

<400> SEQUENCE: 7

```
Gln Val Gln Leu Gln Gln Pro Gly Ala Glu Leu Leu Lys Pro Gly Ala
 1               5                  10                  15

Ser Val Lys Met Ser Cys Lys Ala Ser Gly Tyr Thr Phe Thr Ser Tyr
                 20                  25                  30

Asp Ile His Trp Leu Lys Gln Thr Pro Gly Gln Gly Leu Glu Trp Ile
            35                  40                  45

Gly Ala Ile Tyr Pro Glu Asn Gly Asp Ser Ser Tyr Ser Gln Lys Phe
 50                  55                  60

Lys Gly Lys Ala Thr Leu Thr Ala Asp Lys Ser Ser Asn Thr Ala Tyr
 65                  70                  75                  80

Ile His Leu Ser Ser Leu Thr Ser Glu Asp Ser Ala Val Tyr Tyr Cys
                 85                  90                  95

Ala Arg Gly Gly Tyr Phe Asp Tyr Val Trp Phe Pro Tyr Trp Gly Gln
            100                 105                 110

Gly Thr Leu Val Thr Val Ser Ala
            115                 120
```

<210> SEQ ID NO 8
<211> LENGTH: 112
<212> TYPE: PRT
<213> ORGANISM: Artificial Sequence
<220> FEATURE:
<223> OTHER INFORMATION: B4 Light Chain Variable Region

<400> SEQUENCE: 8

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val Tyr Ser
                 20                  25                  30

Asn Gly Tyr Thr Tyr Leu Glu Trp Tyr Leu Gln Lys Pro Gly Gln Ser
            35                  40                  45

Pro Lys Leu Leu Ile Tyr Gly Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Met Gly Val Tyr Tyr Cys Phe Gln Gly
                 85                  90                  95

Thr His Val Pro Leu Thr Phe Gly Ala Gly Thr Lys Leu Glu Leu Lys
```

-continued

<210> SEQ ID NO 9
<211> LENGTH: 120
<212> TYPE: PRT
<213> ORGANISM: Artificial Sequence
<220> FEATURE:
<223> OTHER INFORMATION: B5 Heavy Chain Variable Region

<400> SEQUENCE: 9

Glu Val Gln Leu Arg Gln Ser Gly Pro Val Leu Val Lys Pro Gly Ala
1               5                   10                  15

Ser Val Lys Met Ser Cys Lys Ala Ser Gly Tyr Thr Phe Thr Gly Tyr
            20                  25                  30

Tyr Met Asn Trp Met Lys Gln Ser His Gly Lys Ser Leu Glu Trp Leu
        35                  40                  45

Ala Val Ile Asn Pro Tyr Asn Gly Asp Thr Ala Tyr Asn Arg Lys Phe
    50                  55                  60

Lys Gly Arg Ala Ile Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Val Arg Asp Asp Gly Tyr His Val Arg Phe Phe Asp Val Trp Gly Thr
            100                 105                 110

Gly Thr Thr Val Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: B5 Light Chain Variable Region

<400> SEQUENCE: 10

Asp Ile Gln Met Thr Gln Ser Pro Ser Ser Leu Ser Ala Ser Leu Gly
1               5                   10                  15

Glu Arg Val Ser Leu Thr Cys Arg Ser Ser Gln Asp Ile Ser Asp Tyr
            20                  25                  30

Leu Ser Trp Leu Gln Gln Lys Pro Asp Gly Thr Ile Lys Arg Leu Ile
        35                  40                  45

Tyr Ser Thr Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Ser Pro Pro
                85                  90                  95

Thr Phe Gly Gly Gly Thr Lys Leu Glu Ile Lys
            100                 105

<210> SEQ ID NO 11
<211> LENGTH: 120
<212> TYPE: PRT
<213> ORGANISM: Artificial Sequence
<220> FEATURE:
<223> OTHER INFORMATION: B9 Heavy Chain Variable Region

<400> SEQUENCE: 11

Glu Val Gln Leu Arg Gln Ser Gly Pro Val Leu Val Lys Pro Gly Ala
1               5                   10                  15

Ser Val Lys Met Ser Cys Lys Ala Ser Gly Tyr Thr Phe Thr Gly Tyr
            20                  25                  30

Tyr Met Asn Trp Val Lys Gln Ser His Gly Lys Ser Leu Glu Trp Leu
        35                  40                  45

Ala Val Ile Asn Pro Tyr Asn Gly Asp Thr Ala Tyr Asn Arg Lys Phe
 50                  55                  60

Lys Gly Arg Ala Thr Leu Thr Val Asp Lys Ser Ser Ser Thr Ala Tyr
 65                  70                  75                  80

Met Glu Leu Asn Arg Leu Thr Ser Glu Asp Ser Ala Val Tyr Tyr Cys
                85                  90                  95

Val Arg Asp Asp Gly Tyr His Val Arg Tyr Phe Asp Val Trp Gly Thr
                100                 105                 110

Gly Thr Thr Val Thr Val Ser Ser
            115                 120

<210> SEQ ID NO 12
<211> LENGTH: 107
<212> TYPE: PRT
<213> ORGANISM: Artificial Sequence
<220> FEATURE:
<223> OTHER INFORMATION: B9 Light Chain Variable Region

<400> SEQUENCE: 12

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Ser Asp Ser
            20                  25                  30

Leu Cys Trp Leu Gln Gln Lys Pro Asp Gly Thr Ile Lys Arg Leu Ile
        35                  40                  45

Tyr Ser Thr Ser Thr Leu Asp Ser Gly Val Pro Lys Arg Phe Ser Gly
 50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Ser Pro Pro
                85                  90                  95

Thr Phe Gly Gly Gly Thr Lys Leu Glu Ile Lys
                100                 105

<210> SEQ ID NO 13
<211> LENGTH: 120
<212> TYPE: PRT
<213> ORGANISM: Artificial Sequence
<220> FEATURE:
<223> OTHER INFORMATION: B6 Heavy Chain Variable Region

<400> SEQUENCE: 13

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Leu Ser Asn Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ala Tyr Asn Leu Lys Phe
 50                  55                  60

Lys Gly Lys Ala Thr Leu Thr Ala Asp Leu Ser Ser Asn Thr Ala Tyr
 65                  70                  75                  80

Met Asp Phe Asn Ser Leu Thr Ser Glu Asp Ser Ala Val Tyr Tyr Cys

```
                85                  90                  95

Ala Arg Asp Asp Gly Tyr His Val Tyr Tyr Phe Asp Tyr Trp Gly Gln
            100                 105                 110

Gly Thr Thr Leu Thr Val Ser Ser
        115                 120

<210> SEQ ID NO 14
<211> LENGTH: 107
<212> TYPE: PRT
<213> ORGANISM: Artificial Sequence
<220> FEATURE:
<223> OTHER INFORMATION: B6 Light Chain Variable Region

<400> SEQUENCE: 14

Asp Ile Gln Leu Thr Gln Ser Pro Ser Ser Leu Ser Ala Ser Leu Gly
1               5                   10                  15

Gln Arg Val Ser Leu Thr Cys Arg Ala Ser Gln Asp Ile Ser Gly Arg
            20                  25                  30

Leu Ser Cys Leu Gln Gln Lys Pro Asp Gly Thr Ile Lys Arg Leu Ile
        35                  40                  45

Tyr Ser Thr Ser Thr Leu Asp Ser Gly Val Pro Lys Arg Phe Ser Gly
 50                  55                  60

Ser Arg Ser Gly Ser Asp Phe Ser Leu Thr Ile Ser Ser Leu Glu Ser
65                  70                  75                  80

Glu Asp Phe Ala Asp Tyr Tyr Cys Leu Gln Cys Val Ser Ser Pro Pro
                85                  90                  95

Thr Phe Gly Gly Gly Thr Lys Leu Glu Ile Lys
            100                 105

<210> SEQ ID NO 15
<211> LENGTH: 120
<212> TYPE: PRT
<213> ORGANISM: Artificial Sequence
<220> FEATURE:
<223> OTHER INFORMATION: B11 Heavy Chain Variable Region

<400> SEQUENCE: 15

Glu Val Gln Leu Gln Gln Ser Gly Pro Val Leu Val Arg Pro Gly Ala
1               5                   10                  15

Ser Val Lys Met Ser Cys Lys Ala Ser Gly Tyr Thr Phe Thr Asn Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Ile Ala Tyr Ser Gln Lys Phe
 50                  55                  60

Lys Gly Lys Ala Thr Leu Thr Val Asp Lys Ser Ser Ser Thr Ala Tyr
65                  70                  75                  80

Met Glu Leu Lys Ser Leu Thr Ser Glu Asp Ser Ala Val Tyr Tyr Cys
                85                  90                  95

Ala Arg Asp Asp Gly Tyr Tyr Val Tyr Tyr Phe Asp Cys Trp Gly Gln
            100                 105                 110

Gly Thr Thr Leu Thr Val Ser Ser
        115                 120

<210> SEQ ID NO 16
<211> LENGTH: 107
<212> TYPE: PRT
<213> ORGANISM: Artificial Sequence
<220> FEATURE:
```

<223> OTHER INFORMATION: B11 Light Chain Variable Region

<400> SEQUENCE: 16

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Gly Ser
            20                  25                  30

Leu Asn Trp Leu Gln Gln Lys Pro Asp Gly Thr Ile Lys Arg Leu Ile
        35                  40                  45

Tyr Ser Thr Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Asn Ala Asn Ser Pro Pro
                85                  90                  95

Thr Phe Gly Gly Gly Thr Lys Leu Glu Ile Lys
            100                 105
```

<210> SEQ ID NO 17
<211> LENGTH: 112
<212> TYPE: PRT
<213> ORGANISM: Artificial Sequence
<220> FEATURE:
<223> OTHER INFORMATION: B7 Heavy Chain Variable Region

<400> SEQUENCE: 17

```
Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
            20                  25                  30

Asn Leu Asn Trp Val Lys Gln Ser Asn Gly Lys Thr Leu Glu Trp Ile
        35                  40                  45

Gly Leu Ile Asn Leu Asp Ser Ala Ala Thr Val Tyr Asn Gln Lys Phe
    50                  55                  60

Lys Gly Lys Ala Thr Leu Thr Ile Asp Gln Ser Ser Thr Thr Ala Tyr
65                  70                  75                  80

Met Gln Leu Asn Ser Leu Thr Ser Asp Ser Ala Val Tyr Tyr Cys
                85                  90                  95

Ala Ser Tyr Asp Tyr Trp Gly Gln Gly Thr Thr Leu Thr Val Ser Ser
            100                 105                 110
```

<210> SEQ ID NO 18
<211> LENGTH: 107
<212> TYPE: PRT
<213> ORGANISM: Artificial Sequence
<220> FEATURE:
<223> OTHER INFORMATION: B7 Light Chain Variable Region

<400> SEQUENCE: 18

```
Asp Ile Gln Met Thr Gln Ser Pro Ser Ser Leu Ser Ala Ser Leu Gly
1               5                   10                  15

Glu Arg Val Ser Leu Ser Cys Arg Ala Ser Gln Asp Ile Ser His Tyr
            20                  25                  30

Leu Asn Trp Phe Gln Gln Lys Pro Asp Gly Thr Phe Lys Arg Leu Ile
        35                  40                  45

Tyr Glu Thr Ser Thr Leu Asp Phe Gly Val Pro Lys Arg Phe Ser Gly
    50                  55                  60

Ser Arg Ser Gly Ser Asp Tyr Ser Leu Thr Ile Gly Ser Leu Glu Ser
```

```
                65                  70                  75                  80
Glu Asp Phe Ala Asp Tyr Tyr Cys Leu Gln Tyr Ala Thr Tyr Pro Leu
                    85                  90                  95

Thr Phe Gly Ala Gly Thr Lys Leu Glu Leu Lys
            100                 105

<210> SEQ ID NO 19
<211> LENGTH: 112
<212> TYPE: PRT
<213> ORGANISM: Artificial Sequence
<220> FEATURE:
<223> OTHER INFORMATION: B10 Heavy Chain Variable Region

<400> SEQUENCE: 19

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
                20                  25                  30

Asn Leu Asn Trp Val Lys Glu Ser Asn Gly Lys Ser Leu Glu Trp Ile
            35                  40                  45

Gly Leu Ile Thr Leu Asp Tyr Gly Thr Thr Ile Tyr Asn Gln Lys Phe
50                  55                  60

Lys Gly Lys Ala Thr Leu Thr Val Asp Gln Ser Ser Ser Ile Ala Tyr
65                  70                  75                  80

Met Gln Leu Asn Ser Leu Thr Ser Asp Ser Ala Val Tyr Tyr Cys
                85                  90                  95

Ala Cys Tyr Asp Tyr Trp Gly Gln Gly Thr Thr Leu Thr Val Ser Ser
            100                 105                 110

<210> SEQ ID NO 20
<211> LENGTH: 107
<212> TYPE: PRT
<213> ORGANISM: Artificial Sequence
<220> FEATURE:
<223> OTHER INFORMATION: B10 Light Chain Variable Region

<400> SEQUENCE: 20

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Ser Asn Tyr
                20                  25                  30

Leu Asn Trp Phe Gln Gln Lys Pro Asp Gly Thr Phe Lys Arg Leu Ile
            35                  40                  45

Tyr Ala Thr Ser Thr Leu Asp Phe Gly Val Pro Lys Arg Phe Ser Gly
            50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Leu Lys
            100                 105

<210> SEQ ID NO 21
<211> LENGTH: 118
<212> TYPE: PRT
<213> ORGANISM: Artificial Sequence
<220> FEATURE:
<223> OTHER INFORMATION: B12 Heavy Chain Variable Region

<400> SEQUENCE: 21
```

```
Glu Val Lys Leu Leu Glu Ser Gly Gly Ser Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Arg Asp Glu Phe Ile Ile Ser Arg Asp Asn Ala Lys Asn Thr Leu Phe
65                  70                  75                  80

Leu Gln Met Ser Lys Val Ile Ser Glu Asp Thr Ala Leu Tyr Tyr Cys
                85                  90                  95

Ala Arg Ile Thr Ser Gly Tyr Tyr Phe Asp Tyr Trp Gly Gln Gly Thr
                100                 105                 110

Thr Leu Thr Val Ser Ser
                115
```

<210> SEQ ID NO 22
<211> LENGTH: 112
<212> TYPE: PRT
<213> ORGANISM: Artificial Sequence
<220> FEATURE:
<223> OTHER INFORMATION: B12 Light Chain Variable Region

<400> SEQUENCE: 22

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Thr Ile Val Tyr Ser
            20                  25                  30

Asn Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Met Gly Val Tyr Tyr Cys Phe Gln Gly
                85                  90                  95

Thr His Val Pro Phe Thr Phe Gly Ser Gly Thr Lys Leu Glu Met Lys
                100                 105                 110
```

<210> SEQ ID NO 23
<211> LENGTH: 123
<212> TYPE: PRT
<213> ORGANISM: Artificial Sequence
<220> FEATURE:
<223> OTHER INFORMATION: B13 Heavy Chain Variable Region

<400> SEQUENCE: 23

```
Glu Val Met Leu Val Glu Ser Gly Gly Gly Leu Val Lys Pro Gly Gly
1               5                   10                  15

Ser Leu Lys Val Ser Cys Ala Ala Ser Gly Phe Thr Phe Ser Ile Tyr
            20                  25                  30

Ala Met Cys Trp Val Arg Gln Thr Pro Glu Lys Arg Leu Glu Trp Val
        35                  40                  45

Ala Thr Ile Ser Ser Gly Gly Ser Asn Thr Tyr Tyr Pro Asp Ser Val
    50                  55                  60

Lys Gly Arg Phe Thr Ile Ser Arg Asp Asn Ala Lys Asn Thr Leu Tyr
```

```
                 65                  70                  75                  80
Leu Gln Met Ser Ser Leu Arg Ser Glu Asp Thr Ala Val Tyr Tyr Cys
                 85                  90                  95

Ala Arg Gly Asp Val Tyr Tyr Asp Tyr Asp Gly Arg Gly Phe Asp Tyr
                100                 105                 110

Trp Gly Gln Gly Thr Thr Leu Thr Val Ser Ser
            115                 120

<210> SEQ ID NO 24
<211> LENGTH: 113
<212> TYPE: PRT
<213> ORGANISM: Artificial Sequence
<220> FEATURE:
<223> OTHER INFORMATION: B13 Light Chain Variable Region

<400> SEQUENCE: 24

Asp Ile Val Met Thr Gln Ser Pro Ser Ser Leu Thr Val Thr Ala Gly
1               5                  10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Met Leu Ile Tyr Trp Ala Ser Thr Arg Glu Ser Gly Val
    50                  55                  60

Pro Glu Arg Phe Thr Gly Ser Gly Ser Gly Thr Asp Phe Thr Leu Thr
65                  70                  75                  80

Ile Asn Ser Val Gln Ala Glu Asp Met Ala Ile Tyr Tyr Cys Gln Asn
                85                  90                  95

Asp Tyr Gly Tyr Pro Leu Ala Phe Gly Ala Gly Thr Arg Leu Glu Leu
                100                 105                 110

Lys

<210> SEQ ID NO 25
<211> LENGTH: 112
<212> TYPE: PRT
<213> ORGANISM: Artificial Sequence
<220> FEATURE:
<223> OTHER INFORMATION: B15 Heavy Chain Variable Region

<400> SEQUENCE: 25

Glu Val Gln Leu Gln Gln Ser Gly Ala Glu Leu Val Arg Pro Gly Ala
1               5                  10                  15

Ser Val Lys Leu Ser Cys Thr Ala Ser Gly Phe Asn Ile Lys Asp Asp
                20                  25                  30

Tyr Met Phe Trp Val Lys Gln Arg Pro Glu Gln Gly Leu Glu Trp Ile
            35                  40                  45

Gly Trp Ile Asp Pro Glu Asn Gly Asp Thr Glu Tyr Ala Ser Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Leu Tyr Ala Tyr Trp Gly Gln Gly Thr Leu Val Thr Val Ser Ala
                100                 105                 110

<210> SEQ ID NO 26
<211> LENGTH: 112
<212> TYPE: PRT
```

<213> ORGANISM: Artificial Sequence
<220> FEATURE:
<223> OTHER INFORMATION: B15 Light Chain Variable Region

<400> SEQUENCE: 26

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Ser Trp Leu Leu Gln Arg Pro Gly Gln Ser
        35                  40                  45

Pro Lys Arg Leu Ile Tyr Leu Val Ser Lys Leu Asp Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Gln Thr Phe Gly Gly Gly Thr Lys Leu Glu Ile Lys
            100                 105                 110

<210> SEQ ID NO 27
<211> LENGTH: 113
<212> TYPE: PRT
<213> ORGANISM: Artificial Sequence
<220> FEATURE:
<223> OTHER INFORMATION: B16 Heavy Chain Variable Region

<400> SEQUENCE: 27

Glu Val Gln Leu His Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Arg Thr Ser Tyr Asn Leu Lys Phe
50                  55                  60

Lys Gly Lys Ala Thr Leu Thr Val Asp Lys Ser Ser Thr Ala Tyr
65                  70                  75                  80

Met Asp Leu Asn Ser Leu Thr Ser Glu Asp Ser Ala Val Tyr Tyr Cys
                85                  90                  95

Ala Ser Pro Glu Gly Tyr Trp Gly Gln Gly Thr Thr Leu Thr Val Ser
            100                 105                 110

Ser

<210> SEQ ID NO 28
<211> LENGTH: 111
<212> TYPE: PRT
<213> ORGANISM: Artificial Sequence
<220> FEATURE:
<223> OTHER INFORMATION: B16 Light Chain Variable Region

<400> SEQUENCE: 28

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Thr Val Asp Asp Ser
            20                  25                  30

Gly Ile Ser Phe Met His Trp Tyr Gln Gln Lys Pro Gly Gln Pro Pro
        35                  40                  45

```
Arg Leu Leu Ile Tyr Arg Ala Ser Lys Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Thr Asp Val Ala Thr Tyr Tyr Cys Gln Gln Asn Asn
                 85                  90                  95

Lys Asp Pro Leu Thr Phe Gly Ala Gly Thr Lys Leu Glu Leu Arg
            100                 105                 110
```

<210> SEQ ID NO 29
<211> LENGTH: 120
<212> TYPE: PRT
<213> ORGANISM: Artificial Sequence
<220> FEATURE:
<223> OTHER INFORMATION: BG27 Heavy Chain Variable Region

<400> SEQUENCE: 29

```
Gln Ala Tyr Leu Gln Gln Ser Gly Ala Asp Leu Val Arg Pro Gly Ala
 1               5                  10                  15

Ser Val Lys Met Ser Cys Lys Ala Ser Gly Tyr Thr Phe Thr Ser Tyr
                20                  25                  30

Asp Met His Trp Val Lys Gln Thr Pro Arg Gln Gly Leu Glu Trp Ile
             35                  40                  45

Gly Ala Ile Tyr Pro Gly Asn Gly Asp Ala Ser Tyr Asn Gln Lys Phe
 50                  55                  60

Lys Gly Lys Ala Thr Leu Thr Val Asp Lys Ala Ser Ser Thr Ala Phe
 65                  70                  75                  80

Met Gln Leu Ser Ser Leu Thr Ser Glu Asp Ser Ala Val Tyr Phe Cys
                 85                  90                  95

Ala Arg Gly Asp Tyr Gly Asn Tyr Val Trp Phe Ala Tyr Trp Gly Gln
            100                 105                 110

Gly Thr Leu Val Thr Val Ser Ala
            115                 120
```

<210> SEQ ID NO 30
<211> LENGTH: 112
<212> TYPE: PRT
<213> ORGANISM: Artificial Sequence
<220> FEATURE:
<223> OTHER INFORMATION: BG27 Light Chain Variable Region

<400> SEQUENCE: 30

```
Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Thr Ile Val His Ser
                20                  25                  30

Asn Arg Tyr Thr Tyr Leu Glu Trp Tyr Leu Gln Lys Pro Gly Gln Ser
             35                  40                  45

Leu Lys Leu Leu Ile Tyr Gly Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Met Gly Val Tyr Tyr Cys Phe Gln Gly
                 85                  90                  95

Thr His Val Pro Pro Thr Phe Gly Ala Gly Thr Lys Leu Glu Leu Lys
            100                 105                 110
```

<210> SEQ ID NO 31

```
<211> LENGTH: 117
<212> TYPE: PRT
<213> ORGANISM: Artificial Sequence
<220> FEATURE:
<223> OTHER INFORMATION: BG29 Heavy Chain Variable Region

<400> SEQUENCE: 31

Gln Ile Gln Leu Gln Gln Ser Gly Pro Glu Val Val Lys Pro Gly Ala
1               5                   10                  15

Ser Val Arg Ile Ser Cys Lys Ala Ser Gly Tyr Thr Phe Ser Asp Tyr
            20                  25                  30

His Ile Asn Trp Val Lys Gln Lys Pro Gly Gln Gly Leu Glu Trp Ile
        35                  40                  45

Gly Trp Ile Tyr Pro Gly Arg Gly Asp Pro Glu Tyr Asn Glu Lys Phe
    50                  55                  60

Lys Gly Lys Ala Thr Leu Thr Val Asp Arg Ser Ala Ser Thr Ala Tyr
65                  70                  75                  80

Met Gln Leu Ser Ser Leu Thr Ser Glu Asp Thr Ser Val Tyr Phe Cys
                85                  90                  95

Glu Ile Tyr Tyr Gly Asn Tyr Ile Asp Tyr Trp Gly Gln Gly Thr Thr
            100                 105                 110

Leu Thr Val Ser Ser
        115

<210> SEQ ID NO 32
<211> LENGTH: 112
<212> TYPE: PRT
<213> ORGANISM: Artificial Sequence
<220> FEATURE:
<223> OTHER INFORMATION: BG29 Light Chain Variable Region

<400> SEQUENCE: 32

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asp Gly Lys Thr Tyr Leu Tyr Trp Phe Leu Gln Arg Pro Gly Gln Ser
        35                  40                  45

Pro Gln Arg Leu Ile Tyr Tyr Met Ser Asn Leu Ala Ser Gly Val Pro
    50                  55                  60

Asp Arg Phe Ser Gly Arg Gly Ser Gly Thr Asp Phe Thr Leu Arg Ile
65                  70                  75                  80

Ser Arg Val Glu Ala Glu Asp Val Gly Val Tyr Tyr Cys Met Gln Ser
                85                  90                  95

Leu Glu Tyr Pro Trp Thr Phe Gly Gly Gly Thr Lys Leu Glu Ile Lys
            100                 105                 110

<210> SEQ ID NO 33
<211> LENGTH: 117
<212> TYPE: PRT
<213> ORGANISM: Artificial Sequence
<220> FEATURE:
<223> OTHER INFORMATION: BG33 Heavy Chain Variable Region

<400> SEQUENCE: 33

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Ser Asp Tyr
            20                  25                  30
```

His Ile Asn Trp Val Lys Gln Lys Pro Gly Gln Gly Leu Glu Trp Ile
            35                  40                  45

Gly Trp Ile Tyr Pro Gly Arg Gly Asn Pro Glu Tyr Asn Glu Lys Phe
 50                  55                  60

Lys Gly Lys Ala Thr Leu Thr Val Asp Arg Ser Ala Asn Thr Ala Tyr
 65                  70                  75                  80

Met Gln Leu Ser Ser Leu Thr Ser Glu Asp Ser Ser Val Tyr Phe Cys
                 85                  90                  95

Glu Ile Tyr Tyr Gly Asn Tyr Leu Asp Tyr Trp Gly Gln Gly Thr Thr
                100                 105                 110

Leu Thr Val Ser Ser
            115

<210> SEQ ID NO 34
<211> LENGTH: 112
<212> TYPE: PRT
<213> ORGANISM: Artificial Sequence
<220> FEATURE:
<223> OTHER INFORMATION: BG33 Light Chain Variable Region

<400> SEQUENCE: 34

Asp Ile Val Met Thr Gln Ala Ala Pro Ser Val Pro Thr Pro Gly
 1               5                  10                  15

Glu Ser Val Ser Ile Ser Cys Arg Ser Ser Lys Ser Leu Leu His Ser
             20                  25                  30

Asp Gly Lys Thr Tyr Leu Tyr Trp Phe Leu Gln Arg Pro Gly Gln Ser
            35                  40                  45

Pro Gln Arg Leu Ile Tyr Tyr Met Ser Asn Leu Ala Ser Gly Val Pro
 50                  55                  60

Asp Arg Phe Ser Gly Arg Gly Ser Gly Thr Asp Phe Thr Leu Arg Ile
 65                  70                  75                  80

Ser Arg Val Glu Ala Glu Asp Val Gly Val Tyr Tyr Cys Met Gln Ser
                 85                  90                  95

Leu Glu Tyr Pro Trp Thr Phe Gly Gly Thr Lys Leu Glu Ile Lys
                100                 105                 110

<210> SEQ ID NO 35
<211> LENGTH: 9
<212> TYPE: PRT
<213> ORGANISM: Artificial Sequence
<220> FEATURE:
<223> OTHER INFORMATION: B1 HC CDR1

<400> SEQUENCE: 35

Gly Tyr Ser Ile Thr Ser Asp Tyr Ala
 1               5

<210> SEQ ID NO 36
<211> LENGTH: 7
<212> TYPE: PRT
<213> ORGANISM: Artificial Sequence
<220> FEATURE:
<223> OTHER INFORMATION: B1 HC CDR2

<400> SEQUENCE: 36

Ile Asp Tyr Ser Gly Ile Thr
 1               5

<210> SEQ ID NO 37
<211> LENGTH: 13
<212> TYPE: PRT

```
<213> ORGANISM: Artificial Sequence
<220> FEATURE:
<223> OTHER INFORMATION: B1 HC CDR3

<400> SEQUENCE: 37

Ala Arg Glu Asp His Tyr Asp Leu Ala Trp Phe Ala Tyr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: B2 HC CDR1

<400> SEQUENCE: 38

Gly Tyr Thr Phe Thr Asp Tyr Tyr
1               5

<210> SEQ ID NO 39
<211> LENGTH: 8
<212> TYPE: PRT
<213> ORGANISM: Artificial Sequence
<220> FEATURE:
<223> OTHER INFORMATION: B2 HC CDR2

<400> SEQUENCE: 39

Ile Phe Pro Gly Ser Gly Ser Thr
1               5

<210> SEQ ID NO 40
<211> LENGTH: 13
<212> TYPE: PRT
<213> ORGANISM: Artificial Sequence
<220> FEATURE:
<223> OTHER INFORMATION: B2 HC CDR3

<400> SEQUENCE: 40

Val Arg Ile His Phe Asp Tyr Asp Trp Phe Phe Asp Val
1               5                   10

<210> SEQ ID NO 41
<211> LENGTH: 8
<212> TYPE: PRT
<213> ORGANISM: Artificial Sequence
<220> FEATURE:
<223> OTHER INFORMATION: B3 HC CDR1

<400> SEQUENCE: 41

Gly Tyr Thr Phe Thr Ser Tyr Asp
1               5

<210> SEQ ID NO 42
<211> LENGTH: 8
<212> TYPE: PRT
<213> ORGANISM: Artificial Sequence
<220> FEATURE:
<223> OTHER INFORMATION: B3 HC CDR2

<400> SEQUENCE: 42

Ile Tyr Pro Glu Asn Gly Asp Ser
1               5

<210> SEQ ID NO 43
<211> LENGTH: 13
<212> TYPE: PRT
<213> ORGANISM: Artificial Sequence
```

```
<220> FEATURE:
<223> OTHER INFORMATION: B3 HC CDR3

<400> SEQUENCE: 43

Ala Arg Gly Gly Tyr Tyr Asp Tyr Val Trp Phe Pro Tyr
1               5                   10

<210> SEQ ID NO 44
<211> LENGTH: 8
<212> TYPE: PRT
<213> ORGANISM: Artificial Sequence
<220> FEATURE:
<223> OTHER INFORMATION: B4 HC CDR1

<400> SEQUENCE: 44

Gly Tyr Thr Phe Thr Ser Tyr Asp
1               5

<210> SEQ ID NO 45
<211> LENGTH: 8
<212> TYPE: PRT
<213> ORGANISM: Artificial Sequence
<220> FEATURE:
<223> OTHER INFORMATION: B4 HC CDR2

<400> SEQUENCE: 45

Ile Tyr Pro Glu Asn Gly Asp Ser
1               5

<210> SEQ ID NO 46
<211> LENGTH: 13
<212> TYPE: PRT
<213> ORGANISM: Artificial Sequence
<220> FEATURE:
<223> OTHER INFORMATION: B4 HC CDR3

<400> SEQUENCE: 46

Ala Arg Gly Gly Tyr Phe Asp Tyr Val Trp Phe Pro Tyr
1               5                   10

<210> SEQ ID NO 47
<211> LENGTH: 8
<212> TYPE: PRT
<213> ORGANISM: Artificial Sequence
<220> FEATURE:
<223> OTHER INFORMATION: B5 HC CDR1

<400> SEQUENCE: 47

Gly Tyr Thr Phe Thr Gly Tyr Tyr
1               5

<210> SEQ ID NO 48
<211> LENGTH: 8
<212> TYPE: PRT
<213> ORGANISM: Artificial Sequence
<220> FEATURE:
<223> OTHER INFORMATION: B5 HC CDR2

<400> SEQUENCE: 48

Ile Asn Pro Tyr Asn Gly Asp Thr
1               5

<210> SEQ ID NO 49
<211> LENGTH: 13
<212> TYPE: PRT
<213> ORGANISM: Artificial Sequence
<220> FEATURE:
```

```
<223> OTHER INFORMATION: B5 HC CDR3

<400> SEQUENCE: 49

Val Arg Asp Asp Gly Tyr His Val Arg Phe Phe Asp Val
1               5                   10

<210> SEQ ID NO 50
<211> LENGTH: 8
<212> TYPE: PRT
<213> ORGANISM: Artificial Sequence
<220> FEATURE:
<223> OTHER INFORMATION: B9 HC CDR1

<400> SEQUENCE: 50

Gly Tyr Thr Phe Thr Gly Tyr Tyr
1               5

<210> SEQ ID NO 51
<211> LENGTH: 8
<212> TYPE: PRT
<213> ORGANISM: Artificial Sequence
<220> FEATURE:
<223> OTHER INFORMATION: B9 HC CDR2

<400> SEQUENCE: 51

Ile Asn Pro Tyr Asn Gly Asp Thr
1               5

<210> SEQ ID NO 52
<211> LENGTH: 13
<212> TYPE: PRT
<213> ORGANISM: Artificial Sequence
<220> FEATURE:
<223> OTHER INFORMATION: B9 HC CDR3

<400> SEQUENCE: 52

Val Arg Asp Asp Gly Tyr His Val Arg Tyr Phe Asp Val
1               5                   10

<210> SEQ ID NO 53
<211> LENGTH: 8
<212> TYPE: PRT
<213> ORGANISM: Artificial Sequence
<220> FEATURE:
<223> OTHER INFORMATION: B6 HC CDR1

<400> SEQUENCE: 53

Gly Tyr Thr Leu Ser Asn Tyr Tyr
1               5

<210> SEQ ID NO 54
<211> LENGTH: 8
<212> TYPE: PRT
<213> ORGANISM: Artificial Sequence
<220> FEATURE:
<223> OTHER INFORMATION: B6 HC CDR2

<400> SEQUENCE: 54

Ile Asn Pro Tyr Asn Gly Asp Thr
1               5

<210> SEQ ID NO 55
<211> LENGTH: 13
<212> TYPE: PRT
<213> ORGANISM: Artificial Sequence
<220> FEATURE:
<223> OTHER INFORMATION: B6 HC CDR3
```

<400> SEQUENCE: 55

Ala Arg Asp Asp Gly Tyr His Val Tyr Tyr Phe Asp Tyr
1               5                   10

<210> SEQ ID NO 56
<211> LENGTH: 8
<212> TYPE: PRT
<213> ORGANISM: Artificial Sequence
<220> FEATURE:
<223> OTHER INFORMATION: B11 HC CDR1

<400> SEQUENCE: 56

Gly Tyr Thr Phe Thr Asn Tyr Tyr
1               5

<210> SEQ ID NO 57
<211> LENGTH: 8
<212> TYPE: PRT
<213> ORGANISM: Artificial Sequence
<220> FEATURE:
<223> OTHER INFORMATION: B11 HC CDR2

<400> SEQUENCE: 57

Ile Asn Pro Tyr Asn Gly Asp Ile
1               5

<210> SEQ ID NO 58
<211> LENGTH: 13
<212> TYPE: PRT
<213> ORGANISM: Artificial Sequence
<220> FEATURE:
<223> OTHER INFORMATION: B11 HC CDR3

<400> SEQUENCE: 58

Ala Arg Asp Asp Gly Tyr Tyr Val Tyr Tyr Phe Asp Cys
1               5                   10

<210> SEQ ID NO 59
<211> LENGTH: 8
<212> TYPE: PRT
<213> ORGANISM: Artificial Sequence
<220> FEATURE:
<223> OTHER INFORMATION: B7 HC CDR1

<400> SEQUENCE: 59

Gly Tyr Ser Phe Ser Asp Tyr Asn
1               5

<210> SEQ ID NO 60
<211> LENGTH: 8
<212> TYPE: PRT
<213> ORGANISM: Artificial Sequence
<220> FEATURE:
<223> OTHER INFORMATION: B7 HC CDR2

<400> SEQUENCE: 60

Ile Asn Leu Asp Ser Ala Ala Thr
1               5

<210> SEQ ID NO 61
<211> LENGTH: 5
<212> TYPE: PRT
<213> ORGANISM: Artificial Sequence
<220> FEATURE:
<223> OTHER INFORMATION: B7 HC CDR3

```
<400> SEQUENCE: 61

Ala Ser Tyr Asp Tyr
1               5

<210> SEQ ID NO 62
<211> LENGTH: 8
<212> TYPE: PRT
<213> ORGANISM: Artificial Sequence
<220> FEATURE:
<223> OTHER INFORMATION: B10 HC CDR1

<400> SEQUENCE: 62

Gly Tyr Ser Phe Thr Asp Tyr Asn
1               5

<210> SEQ ID NO 63
<211> LENGTH: 8
<212> TYPE: PRT
<213> ORGANISM: Artificial Sequence
<220> FEATURE:
<223> OTHER INFORMATION: B10 HC CDR2

<400> SEQUENCE: 63

Ile Thr Leu Asp Tyr Gly Thr Thr
1               5

<210> SEQ ID NO 64
<211> LENGTH: 5
<212> TYPE: PRT
<213> ORGANISM: Artificial Sequence
<220> FEATURE:
<223> OTHER INFORMATION: B10 HC CDR3

<400> SEQUENCE: 64

Ala Cys Tyr Asp Tyr
1               5

<210> SEQ ID NO 65
<211> LENGTH: 8
<212> TYPE: PRT
<213> ORGANISM: Artificial Sequence
<220> FEATURE:
<223> OTHER INFORMATION: B12 HC CDR1

<400> SEQUENCE: 65

Gly Phe Asp Phe Ser Arg Tyr Trp
1               5

<210> SEQ ID NO 66
<211> LENGTH: 8
<212> TYPE: PRT
<213> ORGANISM: Artificial Sequence
<220> FEATURE:
<223> OTHER INFORMATION: B12 HC CDR2

<400> SEQUENCE: 66

Ile Asn Pro Asp Ser Ser Thr Ile
1               5

<210> SEQ ID NO 67
<211> LENGTH: 11
<212> TYPE: PRT
<213> ORGANISM: Artificial Sequence
<220> FEATURE:
<223> OTHER INFORMATION: B12 HC CDR3

<400> SEQUENCE: 67
```

Ala Arg Ile Thr Ser Gly Tyr Tyr Phe Asp Tyr
1               5                   10

<210> SEQ ID NO 68
<211> LENGTH: 8
<212> TYPE: PRT
<213> ORGANISM: Artificial Sequence
<220> FEATURE:
<223> OTHER INFORMATION: B13 HC CDR1

<400> SEQUENCE: 68

Gly Phe Thr Phe Ser Ile Tyr Ala
1               5

<210> SEQ ID NO 69
<211> LENGTH: 8
<212> TYPE: PRT
<213> ORGANISM: Artificial Sequence
<220> FEATURE:
<223> OTHER INFORMATION: B13 HC CDR2

<400> SEQUENCE: 69

Ile Ser Ser Gly Gly Ser Asn Thr
1               5

<210> SEQ ID NO 70
<211> LENGTH: 16
<212> TYPE: PRT
<213> ORGANISM: Artificial Sequence
<220> FEATURE:
<223> OTHER INFORMATION: B13 HC CDR3

<400> SEQUENCE: 70

Ala Arg Gly Asp Val Tyr Tyr Asp Tyr Asp Gly Arg Gly Phe Asp Tyr
1               5                   10                  15

<210> SEQ ID NO 71
<211> LENGTH: 8
<212> TYPE: PRT
<213> ORGANISM: Artificial Sequence
<220> FEATURE:
<223> OTHER INFORMATION: B15 HC CDR1

<400> SEQUENCE: 71

Gly Phe Asn Ile Lys Asp Asp Tyr
1               5

<210> SEQ ID NO 72
<211> LENGTH: 8
<212> TYPE: PRT
<213> ORGANISM: Artificial Sequence
<220> FEATURE:
<223> OTHER INFORMATION: B15 HC CDR2

<400> SEQUENCE: 72

Ile Asp Pro Glu Asn Gly Asp Thr
1               5

<210> SEQ ID NO 73
<211> LENGTH: 5
<212> TYPE: PRT
<213> ORGANISM: Artificial Sequence
<220> FEATURE:
<223> OTHER INFORMATION: B15 HC CDR3

<400> SEQUENCE: 73

Thr Leu Tyr Ala Tyr
1               5

<210> SEQ ID NO 74
<211> LENGTH: 8
<212> TYPE: PRT
<213> ORGANISM: Artificial Sequence
<220> FEATURE:
<223> OTHER INFORMATION: B16 HC CDR1

<400> SEQUENCE: 74

Gly Tyr Thr Phe Thr Asp Tyr Tyr
1               5

<210> SEQ ID NO 75
<211> LENGTH: 8
<212> TYPE: PRT
<213> ORGANISM: Artificial Sequence
<220> FEATURE:
<223> OTHER INFORMATION: B16 HC CDR2

<400> SEQUENCE: 75

Ile Asn Pro Tyr Asn Gly Arg Thr
1               5

<210> SEQ ID NO 76
<211> LENGTH: 6
<212> TYPE: PRT
<213> ORGANISM: Artificial Sequence
<220> FEATURE:
<223> OTHER INFORMATION: B16 HC CDR3

<400> SEQUENCE: 76

Ala Ser Pro Glu Gly Tyr
1               5

<210> SEQ ID NO 77
<211> LENGTH: 8
<212> TYPE: PRT
<213> ORGANISM: Artificial Sequence
<220> FEATURE:
<223> OTHER INFORMATION: BG27 HC CDR1

<400> SEQUENCE: 77

Gly Tyr Thr Phe Thr Ser Tyr Asp
1               5

<210> SEQ ID NO 78
<211> LENGTH: 8
<212> TYPE: PRT
<213> ORGANISM: Artificial Sequence
<220> FEATURE:
<223> OTHER INFORMATION: BG27 HC CDR2

<400> SEQUENCE: 78

Ile Tyr Pro Gly Asn Gly Asp Ala
1               5

<210> SEQ ID NO 79
<211> LENGTH: 13
<212> TYPE: PRT
<213> ORGANISM: Artificial Sequence
<220> FEATURE:
<223> OTHER INFORMATION: BG27 HC CDR3

<400> SEQUENCE: 79

Ala Arg Gly Asp Tyr Gly Asn Tyr Val Trp Phe Ala Tyr

<210> SEQ ID NO 80
<211> LENGTH: 8
<212> TYPE: PRT
<213> ORGANISM: Artificial Sequence
<220> FEATURE:
<223> OTHER INFORMATION: BG29 HC CDR1

<400> SEQUENCE: 80

Gly Tyr Thr Phe Ser Asp Tyr His
1               5

<210> SEQ ID NO 81
<211> LENGTH: 8
<212> TYPE: PRT
<213> ORGANISM: Artificial Sequence
<220> FEATURE:
<223> OTHER INFORMATION: BG29 HC CDR2

<400> SEQUENCE: 81

Ile Tyr Pro Gly Arg Gly Asp Pro
1               5

<210> SEQ ID NO 82
<211> LENGTH: 10
<212> TYPE: PRT
<213> ORGANISM: Artificial Sequence
<220> FEATURE:
<223> OTHER INFORMATION: BG29 HC CDR3

<400> SEQUENCE: 82

Glu Ile Tyr Tyr Gly Asn Tyr Ile Asp Tyr
1               5                   10

<210> SEQ ID NO 83
<211> LENGTH: 8
<212> TYPE: PRT
<213> ORGANISM: Artificial Sequence
<220> FEATURE:
<223> OTHER INFORMATION: BG33 HC CDR1

<400> SEQUENCE: 83

Gly Tyr Thr Phe Ser Asp Tyr His
1               5

<210> SEQ ID NO 84
<211> LENGTH: 8
<212> TYPE: PRT
<213> ORGANISM: Artificial Sequence
<220> FEATURE:
<223> OTHER INFORMATION: BG33 HC CDR2

<400> SEQUENCE: 84

Ile Tyr Pro Gly Arg Gly Asn Pro
1               5

<210> SEQ ID NO 85
<211> LENGTH: 10
<212> TYPE: PRT
<213> ORGANISM: Artificial Sequence
<220> FEATURE:
<223> OTHER INFORMATION: BG33 HC CDR3

<400> SEQUENCE: 85

Glu Ile Tyr Tyr Gly Asn Tyr Leu Asp Tyr
1               5                   10

```
<210> SEQ ID NO 86
<211> LENGTH: 6
<212> TYPE: PRT
<213> ORGANISM: Artificial Sequence
<220> FEATURE:
<223> OTHER INFORMATION: B1 LC CDR1

<400> SEQUENCE: 86

Gln Asp Ile Ser Asn Tyr
1               5

<210> SEQ ID NO 87
<211> LENGTH: 3
<212> TYPE: PRT
<213> ORGANISM: Artificial Sequence
<220> FEATURE:
<223> OTHER INFORMATION: B1 LC CDR2

<400> SEQUENCE: 87

Tyr Thr Ser
1

<210> SEQ ID NO 88
<211> LENGTH: 9
<212> TYPE: PRT
<213> ORGANISM: Artificial Sequence
<220> FEATURE:
<223> OTHER INFORMATION: B1 LC CDR3

<400> SEQUENCE: 88

His Gln Tyr Ser Asn Arg Pro Pro Thr
1               5

<210> SEQ ID NO 89
<211> LENGTH: 11
<212> TYPE: PRT
<213> ORGANISM: Artificial Sequence
<220> FEATURE:
<223> OTHER INFORMATION: B2 LC CDR1

<400> SEQUENCE: 89

Gln Ser Ile Val His Ser Asn Gly Asn Thr Tyr
1               5                   10

<210> SEQ ID NO 90
<211> LENGTH: 3
<212> TYPE: PRT
<213> ORGANISM: Artificial Sequence
<220> FEATURE:
<223> OTHER INFORMATION: B2 LC CDR2

<400> SEQUENCE: 90

Arg Val Ser
1

<210> SEQ ID NO 91
<211> LENGTH: 9
<212> TYPE: PRT
<213> ORGANISM: Artificial Sequence
<220> FEATURE:
<223> OTHER INFORMATION: B2 LC CDR3

<400> SEQUENCE: 91

Phe Gln Gly Thr His Val Pro Tyr Thr
1               5
```

```
<210> SEQ ID NO 92
<211> LENGTH: 11
<212> TYPE: PRT
<213> ORGANISM: Artificial Sequence
<220> FEATURE:
<223> OTHER INFORMATION: B3 LC CDR1

<400> SEQUENCE: 92

Gln Ser Ile Leu Tyr Ser Asn Gly Tyr Thr Tyr
1               5                   10

<210> SEQ ID NO 93
<211> LENGTH: 3
<212> TYPE: PRT
<213> ORGANISM: Artificial Sequence
<220> FEATURE:
<223> OTHER INFORMATION: B3 LC CDR2

<400> SEQUENCE: 93

Gly Val Ser
1

<210> SEQ ID NO 94
<211> LENGTH: 9
<212> TYPE: PRT
<213> ORGANISM: Artificial Sequence
<220> FEATURE:
<223> OTHER INFORMATION: B3 LC CDR3

<400> SEQUENCE: 94

Phe Gln Gly Thr His Val Pro Leu Thr
1               5

<210> SEQ ID NO 95
<211> LENGTH: 11
<212> TYPE: PRT
<213> ORGANISM: Artificial Sequence
<220> FEATURE:
<223> OTHER INFORMATION: B4 LC CDR1

<400> SEQUENCE: 95

Gln Ser Ile Val Tyr Ser Asn Gly Tyr Thr Tyr
1               5                   10

<210> SEQ ID NO 96
<211> LENGTH: 3
<212> TYPE: PRT
<213> ORGANISM: Artificial Sequence
<220> FEATURE:
<223> OTHER INFORMATION: B4 LC CDR2

<400> SEQUENCE: 96

Gly Val Ser
1

<210> SEQ ID NO 97
<211> LENGTH: 9
<212> TYPE: PRT
<213> ORGANISM: Artificial Sequence
<220> FEATURE:
<223> OTHER INFORMATION: B4 LC CDR3

<400> SEQUENCE: 97

Phe Gln Gly Thr His Val Pro Leu Thr
1               5
```

```
<210> SEQ ID NO 98
<211> LENGTH: 6
<212> TYPE: PRT
<213> ORGANISM: Artificial Sequence
<220> FEATURE:
<223> OTHER INFORMATION: B5 LC CDR1

<400> SEQUENCE: 98

Gln Asp Ile Ser Asp Tyr
1               5

<210> SEQ ID NO 99
<211> LENGTH: 3
<212> TYPE: PRT
<213> ORGANISM: Artificial Sequence
<220> FEATURE:
<223> OTHER INFORMATION: B5 LC CDR2

<400> SEQUENCE: 99

Ser Thr Ser
1

<210> SEQ ID NO 100
<211> LENGTH: 9
<212> TYPE: PRT
<213> ORGANISM: Artificial Sequence
<220> FEATURE:
<223> OTHER INFORMATION: B5 LC CDR3

<400> SEQUENCE: 100

Leu Gln Tyr Ala Ser Ser Pro Pro Thr
1               5

<210> SEQ ID NO 101
<211> LENGTH: 6
<212> TYPE: PRT
<213> ORGANISM: Artificial Sequence
<220> FEATURE:
<223> OTHER INFORMATION: B9 LC CDR1

<400> SEQUENCE: 101

Gln Asp Ile Ser Asp Ser
1               5

<210> SEQ ID NO 102
<211> LENGTH: 3
<212> TYPE: PRT
<213> ORGANISM: Artificial Sequence
<220> FEATURE:
<223> OTHER INFORMATION: B9 LC CDR2

<400> SEQUENCE: 102

Ser Thr Ser
1

<210> SEQ ID NO 103
<211> LENGTH: 9
<212> TYPE: PRT
<213> ORGANISM: Artificial Sequence
<220> FEATURE:
<223> OTHER INFORMATION: B9 LC CDR3

<400> SEQUENCE: 103

Leu Gln Tyr Ala Ser Ser Pro Pro Thr
1               5

<210> SEQ ID NO 104
```

```
<211> LENGTH: 6
<212> TYPE: PRT
<213> ORGANISM: Artificial Sequence
<220> FEATURE:
<223> OTHER INFORMATION: B6 LC CDR1

<400> SEQUENCE: 104

Gln Asp Ile Ser Gly Arg
1               5

<210> SEQ ID NO 105
<211> LENGTH: 3
<212> TYPE: PRT
<213> ORGANISM: Artificial Sequence
<220> FEATURE:
<223> OTHER INFORMATION: B6 LC CDR2

<400> SEQUENCE: 105

Ser Thr Ser
1

<210> SEQ ID NO 106
<211> LENGTH: 9
<212> TYPE: PRT
<213> ORGANISM: Artificial Sequence
<220> FEATURE:
<223> OTHER INFORMATION: B6 LC CDR3

<400> SEQUENCE: 106

Leu Gln Cys Val Ser Ser Pro Pro Thr
1               5

<210> SEQ ID NO 107
<211> LENGTH: 6
<212> TYPE: PRT
<213> ORGANISM: Artificial Sequence
<220> FEATURE:
<223> OTHER INFORMATION: B11 LC CDR1

<400> SEQUENCE: 107

Gln Asp Ile Gly Gly Ser
1               5

<210> SEQ ID NO 108
<211> LENGTH: 3
<212> TYPE: PRT
<213> ORGANISM: Artificial Sequence
<220> FEATURE:
<223> OTHER INFORMATION: B11 LC CDR2

<400> SEQUENCE: 108

Ser Thr Ser
1

<210> SEQ ID NO 109
<211> LENGTH: 9
<212> TYPE: PRT
<213> ORGANISM: Artificial Sequence
<220> FEATURE:
<223> OTHER INFORMATION: B11 LC CDR3

<400> SEQUENCE: 109

Leu Gln Asn Ala Asn Ser Pro Pro Thr
1               5

<210> SEQ ID NO 110
<211> LENGTH: 6
```

```
<212> TYPE: PRT
<213> ORGANISM: Artificial Sequence
<220> FEATURE:
<223> OTHER INFORMATION: B7 LC CDR1

<400> SEQUENCE: 110

Gln Asp Ile Ser His Tyr
1               5

<210> SEQ ID NO 111
<211> LENGTH: 3
<212> TYPE: PRT
<213> ORGANISM: Artificial Sequence
<220> FEATURE:
<223> OTHER INFORMATION: B7 LC CDR2

<400> SEQUENCE: 111

Glu Thr Ser
1

<210> SEQ ID NO 112
<211> LENGTH: 9
<212> TYPE: PRT
<213> ORGANISM: Artificial Sequence
<220> FEATURE:
<223> OTHER INFORMATION: B7 LC CDR3

<400> SEQUENCE: 112

Leu Gln Tyr Ala Thr Tyr Pro Leu Thr
1               5

<210> SEQ ID NO 113
<211> LENGTH: 6
<212> TYPE: PRT
<213> ORGANISM: Artificial Sequence
<220> FEATURE:
<223> OTHER INFORMATION: B10 LC CDR1

<400> SEQUENCE: 113

Gln Asp Ile Ser Asn Tyr
1               5

<210> SEQ ID NO 114
<211> LENGTH: 3
<212> TYPE: PRT
<213> ORGANISM: Artificial Sequence
<220> FEATURE:
<223> OTHER INFORMATION: B10 LC CDR2

<400> SEQUENCE: 114

Ala Thr Ser
1

<210> SEQ ID NO 115
<211> LENGTH: 9
<212> TYPE: PRT
<213> ORGANISM: Artificial Sequence
<220> FEATURE:
<223> OTHER INFORMATION: B10 LC CDR3

<400> SEQUENCE: 115

Leu Gln Tyr Ala Ser Tyr Pro Leu Thr
1               5

<210> SEQ ID NO 116
<211> LENGTH: 11
<212> TYPE: PRT
```

<213> ORGANISM: Artificial Sequence
<220> FEATURE:
<223> OTHER INFORMATION: B12 LC CDR1

<400> SEQUENCE: 116

Gln Thr Ile Val Tyr Ser Asn Gly Asn Thr Tyr
1               5                   10

<210> SEQ ID NO 117
<211> LENGTH: 3
<212> TYPE: PRT
<213> ORGANISM: Artificial Sequence
<220> FEATURE:
<223> OTHER INFORMATION: B12 LC CDR2

<400> SEQUENCE: 117

Arg Val Ser
1

<210> SEQ ID NO 118
<211> LENGTH: 9
<212> TYPE: PRT
<213> ORGANISM: Artificial Sequence
<220> FEATURE:
<223> OTHER INFORMATION: B12 LC CDR3

<400> SEQUENCE: 118

Phe Gln Gly Thr His Val Pro Phe Thr
1               5

<210> SEQ ID NO 119
<211> LENGTH: 12
<212> TYPE: PRT
<213> ORGANISM: Artificial Sequence
<220> FEATURE:
<223> OTHER INFORMATION: B13 LC CDR1

<400> SEQUENCE: 119

Gln Ser Leu Leu Asn Ser Gly Asn Gln Lys Asn Tyr
1               5                   10

<210> SEQ ID NO 120
<211> LENGTH: 3
<212> TYPE: PRT
<213> ORGANISM: Artificial Sequence
<220> FEATURE:
<223> OTHER INFORMATION: B13 LC CDR2

<400> SEQUENCE: 120

Trp Ala Ser
1

<210> SEQ ID NO 121
<211> LENGTH: 9
<212> TYPE: PRT
<213> ORGANISM: Artificial Sequence
<220> FEATURE:
<223> OTHER INFORMATION: B13 LC CDR3

<400> SEQUENCE: 121

Gln Asn Asp Tyr Gly Tyr Pro Leu Ala
1               5

<210> SEQ ID NO 122
<211> LENGTH: 11
<212> TYPE: PRT
<213> ORGANISM: Artificial Sequence -continued

```
<220> FEATURE:
<223> OTHER INFORMATION: B15 LC CDR1

<400> SEQUENCE: 122

Gln Ser Leu Leu Tyr Ser Asn Gly Lys Thr Tyr
1               5                   10

<210> SEQ ID NO 123
<211> LENGTH: 3
<212> TYPE: PRT
<213> ORGANISM: Artificial Sequence
<220> FEATURE:
<223> OTHER INFORMATION: B15 LC CDR2

<400> SEQUENCE: 123

Leu Val Ser
1

<210> SEQ ID NO 124
<211> LENGTH: 9
<212> TYPE: PRT
<213> ORGANISM: Artificial Sequence
<220> FEATURE:
<223> OTHER INFORMATION: B15 LC CDR3

<400> SEQUENCE: 124

Val Gln Gly Thr His Phe Pro Gln Thr
1               5

<210> SEQ ID NO 125
<211> LENGTH: 10
<212> TYPE: PRT
<213> ORGANISM: Artificial Sequence
<220> FEATURE:
<223> OTHER INFORMATION: B16 LC CDR1

<400> SEQUENCE: 125

Glu Thr Val Asp Asp Ser Gly Ile Ser Phe
1               5                   10

<210> SEQ ID NO 126
<211> LENGTH: 3
<212> TYPE: PRT
<213> ORGANISM: Artificial Sequence
<220> FEATURE:
<223> OTHER INFORMATION: B16 LC CDR2

<400> SEQUENCE: 126

Arg Ala Ser
1

<210> SEQ ID NO 127
<211> LENGTH: 9
<212> TYPE: PRT
<213> ORGANISM: Artificial Sequence
<220> FEATURE:
<223> OTHER INFORMATION: B16 LC CDR3

<400> SEQUENCE: 127

Gln Gln Asn Asn Lys Asp Pro Leu Thr
1               5

<210> SEQ ID NO 128
<211> LENGTH: 11
<212> TYPE: PRT
<213> ORGANISM: Artificial Sequence
<220> FEATURE:
```

<223> OTHER INFORMATION: BG27 LC CDR1

<400> SEQUENCE: 128

Gln Thr Ile Val His Ser Asn Arg Tyr Thr Tyr
1               5                   10

<210> SEQ ID NO 129
<211> LENGTH: 3
<212> TYPE: PRT
<213> ORGANISM: Artificial Sequence
<220> FEATURE:
<223> OTHER INFORMATION: BG27 HC CDR2

<400> SEQUENCE: 129

Gly Val Ser
1

<210> SEQ ID NO 130
<211> LENGTH: 9
<212> TYPE: PRT
<213> ORGANISM: Artificial Sequence
<220> FEATURE:
<223> OTHER INFORMATION: BG27 LC CDR3

<400> SEQUENCE: 130

Phe Gln Gly Thr His Val Pro Pro Thr
1               5

<210> SEQ ID NO 131
<211> LENGTH: 11
<212> TYPE: PRT
<213> ORGANISM: Artificial Sequence
<220> FEATURE:
<223> OTHER INFORMATION: BG29 LC CDR1

<400> SEQUENCE: 131

Lys Ser Leu Leu His Ser Asp Gly Lys Thr Tyr
1               5                   10

<210> SEQ ID NO 132
<211> LENGTH: 3
<212> TYPE: PRT
<213> ORGANISM: Artificial Sequence
<220> FEATURE:
<223> OTHER INFORMATION: BG29 LC CDR2

<400> SEQUENCE: 132

Tyr Met Ser
1

<210> SEQ ID NO 133
<211> LENGTH: 9
<212> TYPE: PRT
<213> ORGANISM: Artificial Sequence
<220> FEATURE:
<223> OTHER INFORMATION: BG29 LC CDR3

<400> SEQUENCE: 133

Met Gln Ser Leu Glu Tyr Pro Trp Thr
1               5

<210> SEQ ID NO 134
<211> LENGTH: 11
<212> TYPE: PRT
<213> ORGANISM: Artificial Sequence
<220> FEATURE:
<223> OTHER INFORMATION: BG33 LC CDR1

```
<400> SEQUENCE: 134

Lys Ser Leu Leu His Ser Asp Gly Lys Thr Tyr
1               5                   10

<210> SEQ ID NO 135
<211> LENGTH: 3
<212> TYPE: PRT
<213> ORGANISM: Artificial Sequence
<220> FEATURE:
<223> OTHER INFORMATION: BG33 LC CDR2

<400> SEQUENCE: 135

Tyr Met Ser
1

<210> SEQ ID NO 136
<211> LENGTH: 9
<212> TYPE: PRT
<213> ORGANISM: Artificial Sequence
<220> FEATURE:
<223> OTHER INFORMATION: BG33 LC CDR3

<400> SEQUENCE: 136

Met Gln Ser Leu Glu Tyr Pro Trp Thr
1               5

<210> SEQ ID NO 137
<211> LENGTH: 13
<212> TYPE: PRT
<213> ORGANISM: Artificial Sequence
<220> FEATURE:
<223> OTHER INFORMATION: HC CDR3
<220> FEATURE:
<221> NAME/KEY: MISC_FEATURE
<222> LOCATION: (6)..(6)
<223> OTHER INFORMATION: Xaa is Tyr or Phe

<400> SEQUENCE: 137

Ala Arg Gly Gly Tyr Xaa Asp Tyr Val Trp Phe Pro Tyr
1               5                   10

<210> SEQ ID NO 138
<211> LENGTH: 11
<212> TYPE: PRT
<213> ORGANISM: Artificial Sequence
<220> FEATURE:
<223> OTHER INFORMATION: LC CDR1
<220> FEATURE:
<221> NAME/KEY: MISC_FEATURE
<222> LOCATION: (4)..(4)
<223> OTHER INFORMATION: Xaa is Leu or Val

<400> SEQUENCE: 138

Gln Ser Ile Xaa Tyr Ser Asn Gly Tyr Thr Tyr
1               5                   10

<210> SEQ ID NO 139
<211> LENGTH: 8
<212> TYPE: PRT
<213> ORGANISM: Artificial Sequence
<220> FEATURE:
<223> OTHER INFORMATION: HC CDR1
<220> FEATURE:
<221> NAME/KEY: MISC_FEATURE
<222> LOCATION: (4)..(4)
<223> OTHER INFORMATION: Xaa is Phe or Leu
<220> FEATURE:
<221> NAME/KEY: MISC_FEATURE
```

-continued

```
<222> LOCATION: (5)..(5)
<223> OTHER INFORMATION: Xaa is Thr or Ser
<220> FEATURE:
<221> NAME/KEY: MISC_FEATURE
<222> LOCATION: (6)..(6)
<223> OTHER INFORMATION: Xaa is Gly or Asn

<400> SEQUENCE: 139

Gly Tyr Thr Xaa Xaa Xaa Tyr Tyr
1               5

<210> SEQ ID NO 140
<211> LENGTH: 8
<212> TYPE: PRT
<213> ORGANISM: Artificial Sequence
<220> FEATURE:
<223> OTHER INFORMATION: HC CDR2
<220> FEATURE:
<221> NAME/KEY: MISC_FEATURE
<222> LOCATION: (8)..(8)
<223> OTHER INFORMATION: Xaa is Thr or Ile

<400> SEQUENCE: 140

Ile Asn Pro Tyr Asn Gly Asp Xaa
1               5

<210> SEQ ID NO 141
<211> LENGTH: 13
<212> TYPE: PRT
<213> ORGANISM: Artificial Sequence
<220> FEATURE:
<223> OTHER INFORMATION: HC CDR3
<220> FEATURE:
<221> NAME/KEY: MISC_FEATURE
<222> LOCATION: (1)..(1)
<223> OTHER INFORMATION: Xaa is Val or Ala
<220> FEATURE:
<221> NAME/KEY: MISC_FEATURE
<222> LOCATION: (7)..(7)
<223> OTHER INFORMATION: Xaa is His or Tyr
<220> FEATURE:
<221> NAME/KEY: MISC_FEATURE
<222> LOCATION: (9)..(9)
<223> OTHER INFORMATION: Xaa is Arg or Tyr
<220> FEATURE:
<221> NAME/KEY: MISC_FEATURE
<222> LOCATION: (10)..(10)
<223> OTHER INFORMATION: Xaa is Phe or Tyr
<220> FEATURE:
<221> NAME/KEY: MISC_FEATURE
<222> LOCATION: (13)..(13)
<223> OTHER INFORMATION: Xaa is Val, Tyr, or Cys

<400> SEQUENCE: 141

Xaa Arg Asp Asp Gly Tyr Xaa Val Xaa Xaa Phe Asp Xaa
1               5                   10

<210> SEQ ID NO 142
<211> LENGTH: 6
<212> TYPE: PRT
<213> ORGANISM: Artificial Sequence
<220> FEATURE:
<223> OTHER INFORMATION: LC CDR1
<220> FEATURE:
<221> NAME/KEY: MISC_FEATURE
<222> LOCATION: (4)..(4)
<223> OTHER INFORMATION: Xaa is Ser or Gly
<220> FEATURE:
<221> NAME/KEY: MISC_FEATURE
<222> LOCATION: (5)..(5)
<223> OTHER INFORMATION: Xaa is Asp or Gly
<220> FEATURE:
<221> NAME/KEY: MISC_FEATURE
```

```
<222> LOCATION: (6)..(6)
<223> OTHER INFORMATION: Xaa is Tyr, Ser, or Arg

<400> SEQUENCE: 142

Gln Asp Ile Xaa Xaa Xaa
1               5

<210> SEQ ID NO 143
<211> LENGTH: 9
<212> TYPE: PRT
<213> ORGANISM: Artificial Sequence
<220> FEATURE:
<223> OTHER INFORMATION: LC CDR3
<220> FEATURE:
<221> NAME/KEY: MISC_FEATURE
<222> LOCATION: (3)..(3)
<223> OTHER INFORMATION: Xaa is Tyr, Cys, or Asn
<220> FEATURE:
<221> NAME/KEY: MISC_FEATURE
<222> LOCATION: (4)..(4)
<223> OTHER INFORMATION: Xaa is Val or Ala
<220> FEATURE:
<221> NAME/KEY: MISC_FEATURE
<222> LOCATION: (5)..(5)
<223> OTHER INFORMATION: Xaa is Ser or Asn

<400> SEQUENCE: 143

Leu Gln Xaa Xaa Xaa Ser Pro Pro Thr
1               5

<210> SEQ ID NO 144
<211> LENGTH: 8
<212> TYPE: PRT
<213> ORGANISM: Artificial Sequence
<220> FEATURE:
<223> OTHER INFORMATION: HC CDR1
<220> FEATURE:
<221> NAME/KEY: MISC_FEATURE
<222> LOCATION: (5)..(5)
<223> OTHER INFORMATION: Xaa is Ser or Thr

<400> SEQUENCE: 144

Gly Tyr Ser Phe Xaa Asp Tyr Asn
1               5

<210> SEQ ID NO 145
<211> LENGTH: 8
<212> TYPE: PRT
<213> ORGANISM: Artificial Sequence
<220> FEATURE:
<223> OTHER INFORMATION: HC CDR2
<220> FEATURE:
<221> NAME/KEY: MISC_FEATURE
<222> LOCATION: (2)..(2)
<223> OTHER INFORMATION: Xaa is Asn or Thr
<220> FEATURE:
<221> NAME/KEY: MISC_FEATURE
<222> LOCATION: (5)..(5)
<223> OTHER INFORMATION: Xaa is Ser or Tyr
<220> FEATURE:
<221> NAME/KEY: MISC_FEATURE
<222> LOCATION: (6)..(6)
<223> OTHER INFORMATION: Xaa is Ala or Gly
<220> FEATURE:
<221> NAME/KEY: MISC_FEATURE
<222> LOCATION: (7)..(7)
<223> OTHER INFORMATION: Xaa is Ala or Thr

<400> SEQUENCE: 145

Ile Xaa Leu Asp Xaa Xaa Xaa Thr
1               5
```

```
<210> SEQ ID NO 146
<211> LENGTH: 5
<212> TYPE: PRT
<213> ORGANISM: Artificial Sequence
<220> FEATURE:
<223> OTHER INFORMATION: HC CDR3
<220> FEATURE:
<221> NAME/KEY: MISC_FEATURE
<222> LOCATION: (2)..(2)
<223> OTHER INFORMATION: Xaa is Ser or Cys

<400> SEQUENCE: 146

Ala Xaa Tyr Asp Tyr
1               5

<210> SEQ ID NO 147
<211> LENGTH: 6
<212> TYPE: PRT
<213> ORGANISM: Artificial Sequence
<220> FEATURE:
<223> OTHER INFORMATION: LC CDR1
<220> FEATURE:
<221> NAME/KEY: MISC_FEATURE
<222> LOCATION: (5)..(5)
<223> OTHER INFORMATION: Xaa is His or Asn

<400> SEQUENCE: 147

Gln Asp Ile Ser Xaa Tyr
1               5

<210> SEQ ID NO 148
<211> LENGTH: 3
<212> TYPE: PRT
<213> ORGANISM: Artificial Sequence
<220> FEATURE:
<223> OTHER INFORMATION: LC CDR2
<220> FEATURE:
<221> NAME/KEY: MISC_FEATURE
<222> LOCATION: (1)..(1)
<223> OTHER INFORMATION: Xaa is Glu or Ala

<400> SEQUENCE: 148

Xaa Thr Ser
1

<210> SEQ ID NO 149
<211> LENGTH: 9
<212> TYPE: PRT
<213> ORGANISM: Artificial Sequence
<220> FEATURE:
<223> OTHER INFORMATION: LC CDR3
<220> FEATURE:
<221> NAME/KEY: MISC_FEATURE
<222> LOCATION: (5)..(5)
<223> OTHER INFORMATION: Xaa is Thr or Ser

<400> SEQUENCE: 149

Leu Gln Tyr Ala Xaa Tyr Pro Leu Thr
1               5

<210> SEQ ID NO 150
<211> LENGTH: 8
<212> TYPE: PRT
<213> ORGANISM: Artificial Sequence
<220> FEATURE:
<223> OTHER INFORMATION: HC CDR2
<220> FEATURE:
<221> NAME/KEY: MISC_FEATURE
<222> LOCATION: (7)..(7)
<223> OTHER INFORMATION: Xaa is Asp or Asn
```

<400> SEQUENCE: 150

Ile Tyr Pro Gly Arg Gly Xaa Pro
1               5

<210> SEQ ID NO 151
<211> LENGTH: 10
<212> TYPE: PRT
<213> ORGANISM: Artificial Sequence
<220> FEATURE:
<223> OTHER INFORMATION: HC CDR3
<220> FEATURE:
<221> NAME/KEY: MISC_FEATURE
<222> LOCATION: (8)..(8)
<223> OTHER INFORMATION: Xaa is Ile or Leu

<400> SEQUENCE: 151

Glu Ile Tyr Tyr Gly Asn Tyr Xaa Asp Tyr
1               5                   10

<210> SEQ ID NO 152
<211> LENGTH: 525
<212> TYPE: PRT
<213> ORGANISM: Homo sapiens

<400> SEQUENCE: 152

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525

<210> SEQ ID NO 153
<211> LENGTH: 30
<212> TYPE: PRT
<213> ORGANISM: Artificial Sequence
<220> FEATURE:
<223> OTHER INFORMATION: 1-30

<400> SEQUENCE: 153

Gly Pro Pro Ala Ala Pro Gly His Pro Leu Ala Pro Gly Pro His
1               5                   10                  15

Pro Ala Ala Pro Ser Ser Trp Gly Pro Arg Pro Arg Arg Tyr
            20                  25                  30

<210> SEQ ID NO 154
<211> LENGTH: 12
<212> TYPE: PRT
<213> ORGANISM: Artificial Sequence
<220> FEATURE:
<223> OTHER INFORMATION: 3-14

<400> SEQUENCE: 154

Pro Ala Ala Ala Pro Gly His Pro Leu Ala Pro Gly
1               5                   10

```
<210> SEQ ID NO 155
<211> LENGTH: 13
<212> TYPE: PRT
<213> ORGANISM: Artificial Sequence
<220> FEATURE:
<223> OTHER INFORMATION: 2-14

<400> SEQUENCE: 155

Pro Pro Ala Ala Ala Pro Gly His Pro Leu Ala Pro Gly
1               5                   10

<210> SEQ ID NO 156
<211> LENGTH: 14
<212> TYPE: PRT
<213> ORGANISM: Artificial Sequence
<220> FEATURE:
<223> OTHER INFORMATION: 1-14

<400> SEQUENCE: 156

Gly Pro Pro Ala Ala Ala Pro Gly His Pro Leu Ala Pro Gly
1               5                   10

<210> SEQ ID NO 157
<211> LENGTH: 13
<212> TYPE: PRT
<213> ORGANISM: Artificial Sequence
<220> FEATURE:
<223> OTHER INFORMATION: 1-13

<400> SEQUENCE: 157

Gly Pro Pro Ala Ala Ala Pro Gly His Pro Leu Ala Pro
1               5                   10

<210> SEQ ID NO 158
<211> LENGTH: 12
<212> TYPE: PRT
<213> ORGANISM: Artificial Sequence
<220> FEATURE:
<223> OTHER INFORMATION: 1-12; LAG-3 epitope

<400> SEQUENCE: 158

Gly Pro Pro Ala Ala Ala Pro Gly His Pro Leu Ala
1               5                   10

<210> SEQ ID NO 159
<211> LENGTH: 11
<212> TYPE: PRT
<213> ORGANISM: Artificial Sequence
<220> FEATURE:
<223> OTHER INFORMATION: 1-11

<400> SEQUENCE: 159

Gly Pro Pro Ala Ala Ala Pro Gly His Pro Leu
1               5                   10

<210> SEQ ID NO 160
<211> LENGTH: 11
<212> TYPE: PRT
<213> ORGANISM: Artificial Sequence
<220> FEATURE:
<223> OTHER INFORMATION: 2-12

<400> SEQUENCE: 160

Pro Pro Ala Ala Ala Pro Gly His Pro Leu Ala
1               5                   10
```

<210> SEQ ID NO 161
<211> LENGTH: 31
<212> TYPE: PRT
<213> ORGANISM: Artificial Sequence
<220> FEATURE:
<223> OTHER INFORMATION: 31W

<400> SEQUENCE: 161

Trp Gln His Gln Pro Asp Ser Gly Pro Pro Ala Ala Ala Pro Gly His
1               5                   10                  15

Pro Leu Ala Pro Gly Pro His Pro Ala Ala Pro Ser Ser Trp Gly
            20                  25                  30

<210> SEQ ID NO 162
<211> LENGTH: 14
<212> TYPE: PRT
<213> ORGANISM: Artificial Sequence
<220> FEATURE:
<223> OTHER INFORMATION: S14

<400> SEQUENCE: 162

Ser Gly Pro Pro Ala Ala Ala Pro Gly His Pro Leu Ala Pro
1               5                   10

<210> SEQ ID NO 163
<211> LENGTH: 15
<212> TYPE: PRT
<213> ORGANISM: Artificial Sequence
<220> FEATURE:
<223> OTHER INFORMATION: D15

<400> SEQUENCE: 163

Asp Ser Gly Pro Pro Ala Ala Ala Pro Gly His Pro Leu Ala Pro
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: P16

<400> SEQUENCE: 164

Pro Asp Ser Gly Pro Pro Ala Ala Ala Pro Gly His Pro Leu Ala Pro
1               5                   10                  15

<210> SEQ ID NO 165
<211> LENGTH: 17
<212> TYPE: PRT
<213> ORGANISM: Artificial Sequence
<220> FEATURE:
<223> OTHER INFORMATION: Q17

<400> SEQUENCE: 165

Gln Pro Asp Ser Gly Pro Pro Ala Ala Ala Pro Gly His Pro Leu Ala
1               5                   10                  15

Pro

<210> SEQ ID NO 166
<211> LENGTH: 16
<212> TYPE: PRT
<213> ORGANISM: Artificial Sequence
<220> FEATURE:
<223> OTHER INFORMATION: Q16

<400> SEQUENCE: 166

```
Gln Pro Asp Ser Gly Pro Pro Ala Ala Ala Pro Gly His Pro Leu Ala
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Q15

<400> SEQUENCE: 167

Gln Pro Asp Ser Gly Pro Pro Ala Ala Ala Pro Gly His Pro Leu
1               5                   10                  15

<210> SEQ ID NO 168
<211> LENGTH: 14
<212> TYPE: PRT
<213> ORGANISM: Artificial Sequence
<220> FEATURE:
<223> OTHER INFORMATION: Q14

<400> SEQUENCE: 168

Gln Pro Asp Ser Gly Pro Pro Ala Ala Ala Pro Gly His Pro
1               5                   10

<210> SEQ ID NO 169
<211> LENGTH: 16
<212> TYPE: PRT
<213> ORGANISM: Artificial Sequence
<220> FEATURE:
<223> OTHER INFORMATION: 15-30

<400> SEQUENCE: 169

Pro His Pro Ala Ala Pro Ser Ser Trp Gly Pro Arg Pro Arg Arg Tyr
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: 15-29

<400> SEQUENCE: 170

Pro His Pro Ala Ala Pro Ser Ser Trp Gly Pro Arg Pro Arg Arg
1               5                   10                  15

<210> SEQ ID NO 171
<211> LENGTH: 14
<212> TYPE: PRT
<213> ORGANISM: Artificial Sequence
<220> FEATURE:
<223> OTHER INFORMATION: 15-28

<400> SEQUENCE: 171

Pro His Pro Ala Ala Pro Ser Ser Trp Gly Pro Arg Pro Arg
1               5                   10

<210> SEQ ID NO 172
<211> LENGTH: 13
<212> TYPE: PRT
<213> ORGANISM: Artificial Sequence
<220> FEATURE:
<223> OTHER INFORMATION: 15-27

<400> SEQUENCE: 172
```

```
Pro His Pro Ala Ala Pro Ser Ser Trp Gly Pro Arg Pro
1               5                   10
```

<210> SEQ ID NO 173
<211> LENGTH: 12
<212> TYPE: PRT
<213> ORGANISM: Artificial Sequence
<220> FEATURE:
<223> OTHER INFORMATION: 15-26

<400> SEQUENCE: 173

```
Pro His Pro Ala Ala Pro Ser Ser Trp Gly Pro Arg
1               5                   10
```

<210> SEQ ID NO 174
<211> LENGTH: 15
<212> TYPE: PRT
<213> ORGANISM: Artificial Sequence
<220> FEATURE:
<223> OTHER INFORMATION: 16-30

<400> SEQUENCE: 174

```
His Pro Ala Ala Pro Ser Ser Trp Gly Pro Arg Pro Arg Arg Tyr
1               5                   10                  15
```

<210> SEQ ID NO 175
<211> LENGTH: 14
<212> TYPE: PRT
<213> ORGANISM: Artificial Sequence
<220> FEATURE:
<223> OTHER INFORMATION: 17-30

<400> SEQUENCE: 175

```
Pro Ala Ala Pro Ser Ser Trp Gly Pro Arg Pro Arg Arg Tyr
1               5                   10
```

<210> SEQ ID NO 176
<211> LENGTH: 13
<212> TYPE: PRT
<213> ORGANISM: Artificial Sequence
<220> FEATURE:
<223> OTHER INFORMATION: 18-30

<400> SEQUENCE: 176

```
Ala Ala Pro Ser Ser Trp Gly Pro Arg Pro Arg Arg Tyr
1               5                   10
```

<210> SEQ ID NO 177
<211> LENGTH: 12
<212> TYPE: PRT
<213> ORGANISM: Artificial Sequence
<220> FEATURE:
<223> OTHER INFORMATION: 19-30

<400> SEQUENCE: 177

```
Ala Pro Ser Ser Trp Gly Pro Arg Pro Arg Arg Tyr
1               5                   10
```

<210> SEQ ID NO 178
<211> LENGTH: 11
<212> TYPE: PRT
<213> ORGANISM: Artificial Sequence
<220> FEATURE:
<223> OTHER INFORMATION: 20-30

<400> SEQUENCE: 178

```
Pro Ser Ser Trp Gly Pro Arg Pro Arg Arg Tyr
```

```
1               5                   10

<210> SEQ ID NO 179
<211> LENGTH: 10
<212> TYPE: PRT
<213> ORGANISM: Artificial Sequence
<220> FEATURE:
<223> OTHER INFORMATION: 21-30

<400> SEQUENCE: 179

Ser Ser Trp Gly Pro Arg Pro Arg Arg Tyr
1               5                   10

<210> SEQ ID NO 180
<211> LENGTH: 11
<212> TYPE: PRT
<213> ORGANISM: Artificial Sequence
<220> FEATURE:
<223> OTHER INFORMATION: 4-14, LAG-3 epitope

<400> SEQUENCE: 180

Ala Ala Ala Pro Gly His Pro Leu Ala Pro Gly
1               5                   10

<210> SEQ ID NO 181
<211> LENGTH: 10
<212> TYPE: PRT
<213> ORGANISM: Artificial Sequence
<220> FEATURE:
<223> OTHER INFORMATION: 5-14

<400> SEQUENCE: 181

Ala Ala Pro Gly His Pro Leu Ala Pro Gly
1               5                   10

<210> SEQ ID NO 182
<211> LENGTH: 9
<212> TYPE: PRT
<213> ORGANISM: Artificial Sequence
<220> FEATURE:
<223> OTHER INFORMATION: 6-14

<400> SEQUENCE: 182

Ala Pro Gly His Pro Leu Ala Pro Gly
1               5

<210> SEQ ID NO 183
<211> LENGTH: 19
<212> TYPE: PRT
<213> ORGANISM: Artificial Sequence
<220> FEATURE:
<223> OTHER INFORMATION: 1-19

<400> SEQUENCE: 183

Gly Pro Pro Ala Ala Ala Pro Gly His Pro Leu Ala Pro Gly Pro His
1               5                   10                  15

Pro Ala Ala

<210> SEQ ID NO 184
<211> LENGTH: 8
<212> TYPE: PRT
<213> ORGANISM: Artificial Sequence
<220> FEATURE:
<223> OTHER INFORMATION: 7-14

<400> SEQUENCE: 184
```

```
Pro Gly His Pro Leu Ala Pro Gly
1               5
```

<210> SEQ ID NO 185
<211> LENGTH: 8
<212> TYPE: PRT
<213> ORGANISM: Artificial Sequence
<220> FEATURE:
<223> OTHER INFORMATION: 6-13

<400> SEQUENCE: 185

```
Ala Pro Gly His Pro Leu Ala Pro
1               5
```

<210> SEQ ID NO 186
<211> LENGTH: 11
<212> TYPE: PRT
<213> ORGANISM: Artificial Sequence
<220> FEATURE:
<223> OTHER INFORMATION: 14-24

<400> SEQUENCE: 186

```
Gly Pro His Pro Ala Ala Pro Ser Ser Trp Gly
1               5                   10
```

<210> SEQ ID NO 187
<211> LENGTH: 12
<212> TYPE: PRT
<213> ORGANISM: Artificial Sequence
<220> FEATURE:
<223> OTHER INFORMATION: 13-24

<400> SEQUENCE: 187

```
Pro Gly Pro His Pro Ala Ala Pro Ser Ser Trp Gly
1               5                   10
```

<210> SEQ ID NO 188
<211> LENGTH: 13
<212> TYPE: PRT
<213> ORGANISM: Artificial Sequence
<220> FEATURE:
<223> OTHER INFORMATION: 12-24

<400> SEQUENCE: 188

```
Ala Pro Gly Pro His Pro Ala Ala Pro Ser Ser Trp Gly
1               5                   10
```

<210> SEQ ID NO 189
<211> LENGTH: 14
<212> TYPE: PRT
<213> ORGANISM: Artificial Sequence
<220> FEATURE:
<223> OTHER INFORMATION: 11-24

<400> SEQUENCE: 189

```
Leu Ala Pro Gly Pro His Pro Ala Ala Pro Ser Ser Trp Gly
1               5                   10
```

<210> SEQ ID NO 190
<211> LENGTH: 16
<212> TYPE: PRT
<213> ORGANISM: Artificial Sequence
<220> FEATURE:
<223> OTHER INFORMATION: 7-22

<400> SEQUENCE: 190

```
Pro Gly His Pro Leu Ala Pro Gly Pro His Pro Ala Ala Pro Ser Ser
```

<210> SEQ ID NO 191
<211> LENGTH: 17
<212> TYPE: PRT
<213> ORGANISM: Artificial Sequence
<220> FEATURE:
<223> OTHER INFORMATION: 7-23

<400> SEQUENCE: 191

```
Pro Gly His Pro Leu Ala Pro Gly Pro His Pro Ala Ala Pro Ser Ser
1               5                   10                  15

Trp
```

<210> SEQ ID NO 192
<211> LENGTH: 13
<212> TYPE: PRT
<213> ORGANISM: Artificial Sequence
<220> FEATURE:
<223> OTHER INFORMATION: LAG-3 epitope

<400> SEQUENCE: 192

```
Ser Gly Pro Pro Ala Ala Ala Pro Gly His Pro Leu Ala
1               5                   10
```

<210> SEQ ID NO 193
<211> LENGTH: 11
<212> TYPE: PRT
<213> ORGANISM: Artificial Sequence
<220> FEATURE:
<223> OTHER INFORMATION: LAG-3 epitope

<400> SEQUENCE: 193

```
Pro Ala Ala Pro Ser Ser Trp Gly Pro Arg Pro
1               5                   10
```

<210> SEQ ID NO 194
<211> LENGTH: 12
<212> TYPE: PRT
<213> ORGANISM: Artificial Sequence
<220> FEATURE:
<223> OTHER INFORMATION: LAG-3 epitope

<400> SEQUENCE: 194

```
Ala Pro Gly Pro His Pro Ala Ala Pro Ser Ser Trp
1               5                   10
```

<210> SEQ ID NO 195
<211> LENGTH: 120
<212> TYPE: PRT
<213> ORGANISM: Artificial Sequence
<220> FEATURE:
<223> OTHER INFORMATION: B5/H1 VH

<400> SEQUENCE: 195

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Gly Tyr
            20                  25                  30

Tyr Met Asn Trp Val Arg Gln Ala Pro Gly Gln Ser Leu Glu Trp Leu
        35                  40                  45

Gly Val Ile Asn Pro Tyr Asn Gly Asp Thr Ala Tyr Asn Arg Lys Phe
    50                  55                  60

Lys Gly Arg Val Thr Leu Thr Val Asp Lys Ser Thr Ser Thr Val Tyr
```

```
                65                  70                  75                  80
Met Glu Leu Ser Ser Leu Arg Ser Glu Asp Thr Ala Val Tyr Tyr Cys
                    85                  90                  95

Ala Arg Asp Asp Gly Tyr His Val Arg Phe Phe Asp Val Trp Gly Gln
                100                 105                 110

Gly Thr Thr Val Thr Val Ser Ser
            115                 120
```

<210> SEQ ID NO 196
<211> LENGTH: 120
<212> TYPE: PRT
<213> ORGANISM: Artificial Sequence
<220> FEATURE:
<223> OTHER INFORMATION: B5/H2 VH

<400> SEQUENCE: 196

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Gly Tyr
                20                  25                  30

Tyr Met Asn Trp Met Arg Gln Ala Pro Gly Gln Ser Leu Glu Trp Leu
            35                  40                  45

Gly Val Ile Asn Pro Tyr Asn Gly Asp Thr Ala Tyr Asn Arg Lys Phe
        50                  55                  60

Lys Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asp Asp Gly Tyr His Val Arg Phe Phe Asp Val Trp Gly Gln
                100                 105                 110

Gly Thr Thr Val Thr Val Ser Ser
            115                 120
```

<210> SEQ ID NO 197
<211> LENGTH: 120
<212> TYPE: PRT
<213> ORGANISM: Artificial Sequence
<220> FEATURE:
<223> OTHER INFORMATION: B5/H3 VH

<400> SEQUENCE: 197

```
Gln Val Gln Leu Val Gln Ser Gly Ala Val Val Lys Lys Pro Gly Ala
1               5                   10                  15

Ser Val Lys Met Ser Cys Lys Ala Ser Gly Tyr Thr Phe Thr Gly Tyr
                20                  25                  30

Tyr Met Asn Trp Met Arg Gln Ala Pro Gly Gln Ser Leu Glu Trp Leu
            35                  40                  45

Ala Val Ile Asn Pro Tyr Asn Gly Asp Thr Ala Tyr Asn Arg Lys Phe
        50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Asp Asp Gly Tyr His Val Arg Phe Phe Asp Val Trp Gly Gln
                100                 105                 110

Gly Thr Thr Val Thr Val Ser Ser
            115                 120
```

```
<210> SEQ ID NO 198
<211> LENGTH: 120
<212> TYPE: PRT
<213> ORGANISM: Artificial Sequence
<220> FEATURE:
<223> OTHER INFORMATION: B5/H4 VH

<400> SEQUENCE: 198

Gln Val Gln Leu Arg Gln Ser Gly Ala Val Val Lys Lys Pro Gly Ala
1               5                   10                  15

Ser Val Lys Met Ser Cys Lys Ala Ser Gly Tyr Thr Phe Thr Gly Tyr
                20                  25                  30

Tyr Met Asn Trp Met Arg Gln Ala His Gly Gln Ser Leu Glu Trp Leu
            35                  40                  45

Ala Val Ile Asn Pro Tyr Asn Gly Asp Thr Ala Tyr Asn Arg Lys Phe
        50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Val Arg Asp Asp Gly Tyr His Val Arg Phe Phe Asp Val Trp Gly Gln
            100                 105                 110

Gly Thr Thr Val Thr Val Ser Ser
        115                 120

<210> SEQ ID NO 199
<211> LENGTH: 112
<212> TYPE: PRT
<213> ORGANISM: Artificial Sequence
<220> FEATURE:
<223> OTHER INFORMATION: B7/H1 VH

<400> SEQUENCE: 199

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Asn Leu Asn Trp Val Arg Gln Ala Pro Gly Gln Gly Leu Glu Trp Met
            35                  40                  45

Gly Leu Ile Asn Leu Asp Ser Ala Ala Thr Val Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Tyr Asp Tyr Trp Gly Gln Gly Thr Leu Val Thr Val Ser Ser
            100                 105                 110

<210> SEQ ID NO 200
<211> LENGTH: 112
<212> TYPE: PRT
<213> ORGANISM: Artificial Sequence
<220> FEATURE:
<223> OTHER INFORMATION: B7/H2 VH

<400> SEQUENCE: 200

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
```

```
                    20                  25                  30

Asn Leu Asn Trp Val Arg Gln Ala Pro Gly Gln Thr Leu Glu Trp Met
                35                  40                  45

Gly Leu Ile Asn Leu Asp Ser Ala Ala Thr Val Tyr Asn Gln Lys Phe
            50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Tyr Asp Tyr Trp Gly Gln Gly Thr Leu Val Thr Val Ser Ser
            100                 105                 110

<210> SEQ ID NO 201
<211> LENGTH: 112
<212> TYPE: PRT
<213> ORGANISM: Artificial Sequence
<220> FEATURE:
<223> OTHER INFORMATION: B7/H3 VH

<400> SEQUENCE: 201

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Asn Leu Asn Trp Val Arg Gln Ala Pro Gly Gln Gly Leu Glu Trp Met
                35                  40                  45

Gly Leu Ile Asn Leu Asp Ser Ala Ala Thr Val Tyr Asn Gln Lys Phe
            50                  55                  60

Lys Gly Lys Ala Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Tyr Asp Tyr Trp Gly Gln Gly Thr Leu Val Thr Val Ser Ser
            100                 105                 110

<210> SEQ ID NO 202
<211> LENGTH: 112
<212> TYPE: PRT
<213> ORGANISM: Artificial Sequence
<220> FEATURE:
<223> OTHER INFORMATION: B7/H4 VH

<400> SEQUENCE: 202

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Asn Leu Asn Trp Val Arg Gln Ala Pro Gly Gln Thr Leu Glu Trp Met
                35                  40                  45

Gly Leu Ile Asn Leu Asp Ser Ala Ala Thr Val Tyr Asn Gln Lys Phe
            50                  55                  60

Lys Gly Lys Ala Thr Met Thr Arg Asp Gln Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Asp Tyr Trp Gly Gln Gly Thr Leu Val Thr Val Ser Ser
            100                 105                 110
```

<210> SEQ ID NO 203
<211> LENGTH: 112
<212> TYPE: PRT
<213> ORGANISM: Artificial Sequence
<220> FEATURE:
<223> OTHER INFORMATION: B7/H5 VH

<400> SEQUENCE: 203

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Asp Tyr
                20                  25                  30

Asn Leu Asn Trp Val Arg Gln Ala Pro Gly Gln Thr Leu Glu Trp Met
            35                  40                  45

Gly Leu Ile Asn Leu Asp Ser Ala Ala Thr Val Tyr Asn Gln Lys Phe
    50                  55                  60

Lys Gly Lys Ala Thr Met Thr Ile Asp Gln Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Asp Tyr Trp Gly Gln Gly Thr Leu Val Thr Val Ser Ser
            100                 105                 110
```

<210> SEQ ID NO 204
<211> LENGTH: 112
<212> TYPE: PRT
<213> ORGANISM: Artificial Sequence
<220> FEATURE:
<223> OTHER INFORMATION: B7/H6 VH

<400> SEQUENCE: 204

```
Glu Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Asp Tyr
                20                  25                  30

Asn Leu Asn Trp Val Arg Gln Ala Pro Gly Gln Thr Leu Glu Trp Met
            35                  40                  45

Gly Leu Ile Asn Leu Asp Ser Ala Ala Thr Val Tyr Asn Gln Lys Phe
    50                  55                  60

Lys Gly Lys Ala Thr Met Thr Ile Asp Gln Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Tyr Asp Tyr Trp Gly Gln Gly Thr Leu Val Thr Val Ser Ser
            100                 105                 110
```

<210> SEQ ID NO 205
<211> LENGTH: 107
<212> TYPE: PRT
<213> ORGANISM: Artificial Sequence
<220> FEATURE:
<223> OTHER INFORMATION: B5/L1 VL

<400> SEQUENCE: 205

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asp Ile Ser Asp Tyr
                20                  25                  30

Leu Ser Trp Leu Gln Gln Lys Pro Gly Gly Ala Pro Lys Ser Leu Ile
```

```
            35                  40                  45
Tyr Ser Thr Ser Thr Leu Asp Ser Gly Val Pro Ser Arg Phe Ser Gly
         50                  55                  60
Ser Arg Ser Gly Thr Asp Phe Thr Leu Thr Ile Ser Ser Leu Gln Pro
 65                  70                  75                  80
Glu Asp Phe Ala Thr Tyr Tyr Cys Leu Gln Tyr Ala Ser Ser Pro Pro
                 85                  90                  95
Thr Phe Gly Gly Gly Thr Lys Val Glu Ile Lys
            100                 105

<210> SEQ ID NO 206
<211> LENGTH: 107
<212> TYPE: PRT
<213> ORGANISM: Artificial Sequence
<220> FEATURE:
<223> OTHER INFORMATION: B5/L2 VL

<400> SEQUENCE: 206

Asp Ile Gln Met Thr Gln Ser Pro Ser Ser Leu Ser Ala Ser Val Gly
  1               5                  10                  15
Asp Arg Val Thr Ile Thr Cys Arg Ser Ser Gln Asp Ile Ser Asp Tyr
             20                  25                  30
Leu Ser Trp Leu Gln Gln Lys Pro Gly Gly Ala Ile Lys Ser Leu Ile
         35                  40                  45
Tyr Ser Thr Ser Thr Leu Asp Ser Gly Val Pro Ser Arg Phe Ser Gly
     50                  55                  60
Ser Arg Ser Gly Thr Asp Phe Thr Leu Thr Ile Ser Ser Leu Gln Pro
 65                  70                  75                  80
Glu Asp Phe Ala Thr Tyr Tyr Cys Leu Gln Tyr Ala Ser Ser Pro Pro
                 85                  90                  95
Thr Phe Gly Gly Gly Thr Lys Val Glu Ile Lys
            100                 105

<210> SEQ ID NO 207
<211> LENGTH: 107
<212> TYPE: PRT
<213> ORGANISM: Artificial Sequence
<220> FEATURE:
<223> OTHER INFORMATION: B5/L3 VL

<400> SEQUENCE: 207

Asp Ile Gln Met Thr Gln Ser Pro Ser Ser Leu Ser Ala Ser Val Gly
  1               5                  10                  15
Asp Arg Val Thr Ile Thr Cys Arg Ser Ser Gln Asp Ile Ser Asp Tyr
             20                  25                  30
Leu Ser Trp Leu Gln Gln Lys Pro Gly Gly Ala Ile Lys Ser Leu Ile
         35                  40                  45
Tyr Ser Thr Ser Thr Leu Asp Ser Gly Val Pro Ser Arg Phe Ser Gly
     50                  55                  60
Ser Arg Ser Gly Thr Asp Tyr Thr Leu Thr Ile Ser Ser Leu Gln Pro
 65                  70                  75                  80
Glu Asp Phe Ala Thr Tyr Tyr Cys Leu Gln Tyr Ala Ser Ser Pro Pro
                 85                  90                  95
Thr Phe Gly Gly Gly Thr Lys Val Glu Ile Lys
            100                 105

<210> SEQ ID NO 208
<211> LENGTH: 107
```

```
<212> TYPE: PRT
<213> ORGANISM: Artificial Sequence
<220> FEATURE:
<223> OTHER INFORMATION: B5/L4 VL

<400> SEQUENCE: 208

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asp Ile Ser Asp Tyr
            20                  25                  30

Leu Ser Trp Leu Gln Gln Lys Pro Gly Gly Ala Ile Lys Arg Leu Ile
        35                  40                  45

Tyr Ser Thr Ser Thr Leu Asp Ser Gly Val Pro Lys Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Ser Pro Pro
                85                  90                  95

Thr Phe Gly Gly Gly Thr Lys Val Glu Ile Lys
            100                 105

<210> SEQ ID NO 209
<211> LENGTH: 107
<212> TYPE: PRT
<213> ORGANISM: Artificial Sequence
<220> FEATURE:
<223> OTHER INFORMATION: B7/L5 VL

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser His Tyr
            20                  25                  30

Leu Asn Trp Phe Gln Gln Lys Pro Gly Lys Ala Pro Lys Leu Leu Ile
        35                  40                  45

Tyr Glu Thr Ser Thr Leu Asp Phe Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Ala Thr Tyr Pro Leu
                85                  90                  95

Thr Phe Gly Gly Gly Thr Lys Val Glu Ile Lys
            100                 105

<210> SEQ ID NO 210
<211> LENGTH: 107
<212> TYPE: PRT
<213> ORGANISM: Artificial Sequence
<220> FEATURE:
<223> OTHER INFORMATION: B7/L8 VL

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser His Tyr
            20                  25                  30

Leu Asn Trp Phe Gln Gln Lys Pro Gly Lys Ala Pro Lys Arg Leu Ile
        35                  40                  45

Tyr Glu Thr Ser Thr Leu Asp Phe Gly Val Pro Ser Arg Phe Ser Gly
```

```
                50                  55                  60
Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln Tyr Ala Thr Tyr Pro Leu
                 85                  90                  95

Thr Phe Gly Gly Gly Thr Lys Val Glu Ile Lys
                100                 105
```

ANTI-LAG-3 ANTIBODIES AND USES THEREOF

CROSS REFERENCE TO RELATED APPLICATIONS

This application is a Section 371 of International Application No. PCT/US2018/048221, filed Aug. 28, 2018, which published in the English language on Mar. 7, 2019 under International Publication No. WO 2019/046225 A1, which claims priority to U.S. Provisional Application No. 62/551,927, filed on Aug. 30, 2017; U.S. Provisional Application No. 62/588,475, filed on Nov. 20, 2017; and U.S. Provisional Application No. 62/626,310, filed Feb. 5, 2018. Each disclosure is incorporated herein by reference in its entirety.

FIELD OF THE INVENTION

This invention relates to monoclonal anti-LAG-3 antibodies, nucleic acids and expression vectors encoding the antibodies, recombinant cells containing the vectors, and compositions comprising the antibodies. Methods of making the antibodies, and methods of using the antibodies to treat diseases including cancer, inflammatory diseases, autoimmune diseases, infectious diseases, type 1 diabetes, and/or associated complications are also provided.

REFERENCE TO SEQUENCE LISTING SUBMITTED ELECTRONICALLY

This application contains a sequence listing, which is submitted electronically via EFS-Web as an ASCII formatted sequence listing with a file name 689204.4U1 Sequence Listing" and a creation date of Feb. 13, 2020, and having a size of 89 kb. The sequence listing submitted via EFS-Web is part of the specification and is herein incorporated by reference in its entirety.

BACKGROUND OF THE INVENTION

Immune suppression has long been recognized as one of the critical causes for cancer. Recently, stimulation of the immune responses to cancer cells has exhibited durable efficacy in cancer treatment. This is highlighted by the tremendous success of therapeutics that target immune checkpoint proteins such as PD-1, PD-L1 and CTLA-4. However, only a small fraction of patients responds to these immune checkpoint therapies. It raises the question whether the immune response to cancer cells is suppressed by additional mechanisms, and whether the blockage of these suppression mechanisms can treat more patients (for review, see Hahn et al., Immunotherapy 2017; 9:681-692).

In addition to PD-1, PD-L1 and CTLA-4, T effector cells are negatively modulated by multiple co-inhibitory checkpoint proteins, such as B7-H3, BTLA, LAG-3 (lymphocyte activation gene 3; CD223), TIM-3 and TIGIT. Among them, LAG-3 is expressed on the surface of activated T cells (Triebel, et al., J. Exp. Med. 1990; 171:1393-1405) and exhibits a unique co-inhibitory activity. Both LAG-3 and CD4 T cell co-receptor bind to the major histocompatibility complex (MHC) class II molecules at the same site, but the LAG-3 binding is of much higher affinity than that of CD4 (Huard, et al., Immunogenetics 1994; 39:213-217). Therefore, the expression of LAG-3 on T cells prevents the binding of CD4 to the MEW class II molecules on antigen presenting cells (APCs), inhibits the co-stimulatory activity of the MHC class II molecules, and negatively modulates the maintenance of T cell activities.

In addition to the inhibiting signal into pre-activated LAG-3+ cells triggered by the binding of MHC class II molecules to LAG-3, it has been reported that LAG-3 on the surface of T regulatory (Treg) cells also suppresses the activity of dendritic cells (DCs) through binding to MEW class II molecules (Huang, et al., Immunity 2004; 21:503-513; Liang, et al., J Immunol 2008; 180:5916-5926). Such backward signaling has the potential to further suppress immune response by downregulating the activity of DCs, and consequently downregulating the activation of naïve T cells and other LAG-3 negative immune cells whose activation and/or activity depend on DCs.

LAG-3 is also expressed on the surface of natural killer cells (Baixeras, et al., J. Exp. Med 1992; 176:327-337), B cells (Kisielow, et al., Eur. J. Immunol. 2005; 35:2081-2088) and plasmacytoid dendritic cells (Workman, et al., J Immunol 2009; 182:1885-1891). Compared with the inhibitory activity on T cells, its function in other immune cells is poorly understood. In addition to binding to MEW class II molecules, LAG-3 is also reported to bind to LSECtin (Xu, et al., Cancer Res 2014; 74:3418-3428), a dendritic cell-specific intercellular adhesion molecule-3-grabbing non-integrin (DC-SIGN) family lectin on the surface of dendritic cells, and the binding is suggested to negatively regulate T cell proliferation. A therapeutic monoclonal antibody (mAb) that blocks these functions of LAG-3 may provide additional therapeutic values.

The binding of MHC class II molecules to T cell receptor (TCR) and the subsequent T cell activation require an antigen. Therefore, LAG-3 specifically inhibits antigen-activated T cells, which is unique from other inhibitory checkpoint mechanisms. Taken together, the LAG-3/MHC class II axis plays an important role in bridging the innate and adaptive immunities. A therapeutic monoclonal antibody that blocks the LAG-3/MHC class II binding has the potential to reactivate an immune response to cancer by itself as a monotherapy or in combination with other immuno-oncology therapeutics such as anti-PD1, anti-PD-L1, anti-CTLA-4, anti-TIM-3, and anti-CD47 antibodies.

LAG-3 limits Treg proliferation and function and may contribute to Treg insufficiency in autoimmune diseases such as type 1 diabetes (Zhang et al., Sci Immunol. 2017; 31:2(9).) An anti-LAG-3 mAb that improves Treg activity has the therapeutic potential to treat type 1 diabetes.

BRIEF SUMMARY OF THE INVENTION

In one general aspect, the invention relates to isolated monoclonal antibodies or antigen-binding fragments thereof that bind LAG-3.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:
  a. SEQ ID NOs:35, 36, 37, 86, 87, and 88, respectively;
  b. SEQ ID NOs:38, 39, 40, 89, 90, and 91, respectively;
  c. SEQ ID NOs:41, 42, 137, 138, 93, and 94, respectively;
  d. SEQ ID NOs:139, 140, 141, 142, 99, and 143, respectively;
  e. SEQ ID NOs:144, 145, 146, 147, 148, and 149, respectively;
  f. SEQ ID NOs:65, 66, 67, 116, 117, and 118, respectively;

g. SEQ ID NOs:68, 69, 70, 119, 120, and 121, respectively;
h. SEQ ID NOs:71, 72, 73, 122, 123, and 124, respectively;
i. SEQ ID NOs:74, 75, 76, 125, 126, and 127, respectively;
j. SEQ ID NOs:77, 78, 79, 128, 129, and 130, respectively; or
k. SEQ ID NOs:80, 150, 151, 131, 132, and 133, respectively;

wherein the antibody or antigen-binding fragment thereof specifically binds LAG-3, preferably human LAG-3.

SEQ ID NO:137 is represented by the amino acid sequence ARGGYX$_1$DYVWFPY, wherein X$_1$ is an amino acid selected from the group consisting of Y and F.

SEQ ID NO:138 is represented by the amino acid sequence QSIX$_1$YSNGYTY, wherein X$_1$ is an amino acid selected from the group consisting of L and V.

SEQ ID NO:139 is represented by the amino acid sequence GYTX$_1$X$_2$X$_3$YY, wherein X$_1$ is an amino acid selected from the group consisting of F and L; X$_2$ is an amino acid selected from the group consisting of T and S; X$_3$ is an amino acid selected from the group consisting of G and N.

SEQ ID NO:140 is represented by the amino acid sequence INPYNGDX$_1$, wherein X$_1$ is an amino acid selected from the group consisting of T and I.

SEQ ID NO:141 is represented by the amino acid sequence X$_1$RDDGYX$_2$VX$_3$X$_4$FDX$_5$, wherein X$_1$ is an amino acid selected from the group consisting of V and A; X$_2$ is an amino acid selected from the group consisting of H and Y; X$_3$ is an amino acid selected from the group consisting of R and Y; X$_4$ is an amino acid selected from the group consisting of F and Y; and X$_5$ is an amino acid selected from the group consisting of V, Y, and C.

SEQ ID NO:142 is represented by the amino acid sequence QDIX$_1$X$_2$X$_3$, wherein X$_1$ is an amino acid selected from the group consisting of S and G; X$_2$ is an amino acid selected from the group consisting of D and G; and X$_3$ is an amino acid selected from the group consisting of Y, S, and R.

SEQ ID NO:143 is represented by the amino acid sequence LQX$_1$X$_2$X$_3$SPPT, wherein X$_1$ is an amino acid selected from the group consisting of Y, C, and N; X$_2$ is an amino acid selected from the group consisting of V and A; and X$_3$ is an amino acid selected from the group consisting of S and N.

SEQ ID NO:144 is represented by the amino acid sequence GYSFX$_1$DYN, wherein X$_1$ is an amino acid selected from the group consisting of S and T.

SEQ ID NO:145 is represented by the amino acid sequence IX$_1$LDX$_2$X$_3$X$_4$T, wherein X$_1$ is an amino acid selected from the group consisting of N and T; X$_2$ is an amino acid selected from the group consisting of S and Y; X$_3$ is an amino acid selected from the group consisting of A and G; and X$_4$ is an amino acid selected from the group consisting of A and T.

SEQ ID NO:146 is represented by the amino acid sequence AX$_1$YDY, wherein X$_1$ is an amino acid selected from the group consisting of S and C.

SEQ ID NO:147 is represented by the amino acid sequence QDISX$_1$Y, wherein X$_1$ is an amino acid selected from the group consisting of H and N.

SEQ ID NO:148 is represented by the amino acid sequence X$_1$TS, wherein X$_1$ is an amino acid selected from the group consisting of E and A.

SEQ ID NO:149 is represented by the amino acid sequence LQYAX$_1$YPLT, wherein X$_1$ is an amino acid selected from the group consisting of T and S.

SEQ ID NO:150 is represented by the amino acid sequence of IYPGRGX$_1$P, wherein X$_1$ is an amino acid selected from the group consisting of D and N.

SEQ ID NO:151 is represented by the amino acid sequence of EIYYGNYX$_1$DY, wherein X$_1$ is an amino acid selected from the group consisting of I and L.

In certain embodiments, the isolated monoclonal antibody or antigen-binding fragment thereof comprises a heavy chain variable region having a polypeptide sequence at least 95% identical to SEQ ID NO:1, 3, 5, 7, 9, 11, 13, 15, 17, 19, 21, 23, 25, 27, 29, 31, or 33, or a light chain variable region having a polypeptide sequence at least 95% identical to SEQ ID NO:2, 4, 6, 8, 10, 12, 14, 16, 18, 20, 22, 24, 26, 28, 30, 32, or 34.

In certain embodiments, the isolated monoclonal antibody or antigen-binding fragment thereof comprises:
(a) a heavy chain variable region having the polypeptide sequence of SEQ ID NO:1, and a light chain variable region having the polypeptide sequence of SEQ ID NO:2;
(b) a heavy chain variable region having the polypeptide sequence of SEQ ID NO:3, and a light chain variable region having the polypeptide sequence of SEQ ID NO:4;
(c) a heavy chain variable region having the polypeptide sequence of SEQ ID NO:5, and a light chain variable region having the polypeptide sequence of SEQ ID NO:6;
(d) a heavy chain variable region having the polypeptide sequence of SEQ ID NO:7, and a light chain variable region having the polypeptide sequence of SEQ ID NO:8;
(e) a heavy chain variable region having the polypeptide sequence of SEQ ID NO:9, and a light chain variable region having the polypeptide sequence of SEQ ID NO:10;
(f) a heavy chain variable region having the polypeptide sequence of SEQ ID NO:11, and a light chain variable region having the polypeptide sequence of SEQ ID NO:12;
(g) a heavy chain variable region having the polypeptide sequence of SEQ ID NO:13, and a light chain variable region having the polypeptide sequence of SEQ ID NO:14;
(h) a heavy chain variable region having the polypeptide sequence of SEQ ID NO:15, and a light chain variable region having the polypeptide sequence of SEQ ID NO:16;
(i) a heavy chain variable region having the polypeptide sequence of SEQ ID NO:17, and a light chain variable region having the polypeptide sequence of SEQ ID NO:18;
(j) a heavy chain variable region having the polypeptide sequence of SEQ ID NO:19, and a light chain variable region having the polypeptide sequence of SEQ ID NO:20;
(k) a heavy chain variable region having the polypeptide sequence of SEQ ID NO:21, and a light chain variable region having the polypeptide sequence of SEQ ID NO:22;
(l) a heavy chain variable region having the polypeptide sequence of SEQ ID NO:23, and a light chain variable region having the polypeptide sequence of SEQ ID NO:24;

(m) a heavy chain variable region having the polypeptide sequence of SEQ ID NO:25, and a light chain variable region having the polypeptide sequence of SEQ ID NO:26;
(n) a heavy chain variable region having the polypeptide sequence of SEQ ID NO:27, and a light chain variable region having the polypeptide sequence of SEQ ID NO:28;
(o) a heavy chain variable region having the polypeptide sequence of SEQ ID NO:29, and a light chain variable region having the polypeptide sequence of SEQ ID NO:30;
(p) a heavy chain variable region having the polypeptide sequence of SEQ ID NO:31, and a light chain variable region having the polypeptide sequence of SEQ ID NO:32; or
(q) a heavy chain variable region having the polypeptide sequence of SEQ ID NO:33, and a light chain variable region having the polypeptide sequence of SEQ ID NO:34.

Also provided are isolated monoclonal antibodies or antigen-binding fragments thereof to LAG-3 that specifically bind to an epitope comprising the amino acid sequence of SEQ ID NO:192. Also provided are isolated monoclonal antibodies or antigen-binding fragments thereof to LAG-3 that specifically bind to an epitope comprising the amino acid sequence of SEQ ID NO:193. Also provided are isolated monoclonal antibodies or antigen-binding fragments thereof to LAG-3 that specifically bind to an epitope comprising the amino acid sequence of SEQ ID NO:158. Also provided are isolated monoclonal antibodies or antigen-binding fragments thereof to LAG-3 that specifically bind to an epitope comprising the amino acid sequence of SEQ ID NO:180. Also provided are isolated monoclonal antibodies or antigen-binding fragments thereof to LAG-3 that specifically bind to an epitope comprising the amino acid sequence of SEQ ID NO:194. The isolated monoclonal antibodies or antigen-binding fragments thereof can, for example, inhibit LAG-3 activity.

In certain embodiments, the isolated monoclonal antibody or antigen-binding fragment thereof is capable of blocking binding of LAG-3 to WIC class II molecules.

In certain embodiments, the isolated monoclonal antibody or antigen-binding fragment thereof is capable of blocking binding of LAG-3 to LSECtin.

In certain embodiments, the isolated monoclonal antibody or antigen-binding fragment thereof is chimeric.

In certain embodiments, the isolated monoclonal antibody or antigen-binding fragment thereof is human or humanized. In certain embodiments, the humanized monoclonal antibody or antigen-binding fragment thereof comprises:
a. a heavy chain variable region having the polypeptide sequence of SEQ ID NO:195, and a light chain variable region having the polypeptide sequence of SEQ ID NO:208
b. a heavy chain variable region having the polypeptide sequence of SEQ ID NO:196, and a light chain variable region having the polypeptide sequence of SEQ ID NO:206;
c. a heavy chain variable region having the polypeptide sequence of SEQ ID NO:197, and a light chain variable region having the polypeptide sequence of SEQ ID NO:205;
d. a heavy chain variable region having the polypeptide sequence of SEQ ID NO:197, and a light chain variable region having the polypeptide sequence of SEQ ID NO:206;
e. a heavy chain variable region having the polypeptide sequence of SEQ ID NO:197, and a light chain variable region having the polypeptide sequence of SEQ ID NO:207;
f. a heavy chain variable region having the polypeptide sequence of SEQ ID NO:198, and a light chain variable region having the polypeptide sequence of SEQ ID NO:205;
g. a heavy chain variable region having the polypeptide sequence of SEQ ID NO:199, and a light chain variable region having the polypeptide sequence of SEQ ID NO:209;
h. a heavy chain variable region having the polypeptide sequence of SEQ ID NO:200, and a light chain variable region having the polypeptide sequence of SEQ ID NO:209;
i. a heavy chain variable region having the polypeptide sequence of SEQ ID NO:201, and a light chain variable region having the polypeptide sequence of SEQ ID NO:209;
j. a heavy chain variable region having the polypeptide sequence of SEQ ID NO:202, and a light chain variable region having the polypeptide sequence of SEQ ID NO:209;
k. a heavy chain variable region having the polypeptide sequence of SEQ ID NO:203, and a light chain variable region having the polypeptide sequence of SEQ ID NO:209;
l. a heavy chain variable region having the polypeptide sequence of SEQ ID NO:204, and a light chain variable region having the polypeptide sequence of SEQ ID NO:209;
m. a heavy chain variable region having the polypeptide sequence of SEQ ID NO:199, and a light chain variable region having the polypeptide sequence of SEQ ID NO:210;
n. a heavy chain variable region having the polypeptide sequence of SEQ ID NO:200, and a light chain variable region having the polypeptide sequence of SEQ ID NO:210;
o. a heavy chain variable region having the polypeptide sequence of SEQ ID NO:201, and a light chain variable region having the polypeptide sequence of SEQ ID NO:210;
p. a heavy chain variable region having the polypeptide sequence of SEQ ID NO:202, and a light chain variable region having the polypeptide sequence of SEQ ID NO:210;
q. a heavy chain variable region having the polypeptide sequence of SEQ ID NO:203, and a light chain variable region having the polypeptide sequence of SEQ ID NO:210; or
r. a heavy chain variable region having the polypeptide sequence of SEQ ID NO:204, and a light chain variable region having the polypeptide sequence of SEQ ID NO:210.

Also provided are isolated nucleic acids encoding the monoclonal antibodies or antigen-binding fragments thereof of the invention disclosed herein.

Also provided are vectors comprising the isolated nucleic acids encoding the monoclonal antibodies or antigen-binding fragments thereof of the invention.

Also provided are host cells comprising the vectors comprising the isolated nucleic acids encoding the monoclonal antibodies or antigen-binding fragments thereof of the invention.

In certain embodiments, provided is a pharmaceutical composition comprising the isolated monoclonal antibody or antigen-binding fragment thereof of the invention and a pharmaceutically acceptable carrier.

Also provided are methods of blocking binding of LAG-3 to MHC class II molecules in a subject in need thereof, comprising administering to the subject the pharmaceutical compositions of the invention.

Also provided are methods of blocking binding of LAG-3 to LSECtin in a subject in need thereof, comprising administering to the subject the pharmaceutical compositions of the invention.

Also provided are methods of treating cancer in a subject in need thereof, comprising administering to the subject the pharmaceutical compositions of the invention. The cancer can be any liquid or solid cancer, for example, it can be selected from, but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Also provided are methods of treating an infectious disease in a subject in need thereof, comprising administering to the subject the pharmaceutical compositions of the invention.

Also provided are methods of treating an inflammatory disease in a subject in need thereof, comprising administering to the subject the pharmaceutical compositions of the invention.

Also provided are methods of treating an autoimmune disease in a subject in need thereof, comprising administering to the subject the pharmaceutical compositions of the invention.

Also provided are methods of treating a type 1 diabetes in a subject in need thereof, comprising administering to the subject the pharmaceutical compositions of the invention.

Also provided are methods of producing the monoclonal antibody or antigen-binding fragment thereof of the invention, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

Also provided are methods of producing a pharmaceutical composition comprising the monoclonal antibody or antigen-binding fragment thereof of the invention, comprising combining the monoclonal antibody or antigen-binding fragment with a pharmaceutically acceptable carrier to obtain the pharmaceutical composition.

Also provided are methods of determining a level of LAG-3 in a subject. The methods comprise (a) obtaining a sample from the subject; (b) contacting the sample with an antibody or antigen-binding fragment thereof of the invention; and (c) determining the level of LAG-3 in the subject. In certain embodiments, the sample is a tissue sample. The tissue sample can, for example, be a cancer tissue sample. In certain embodiments, the sample is a blood sample.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 4A shows a graph of the inhibition of human LAG-3 binding to Daudi cells by anti-LAG-3 chimeric antibodies B2C, B7C, and B10C. FIG. 4B shows a graph of the inhibition of human LAG-3 binding to Daudi cells by anti-LAG-3 chimeric antibodies B1C, B3C, B4C, B5C, B9C, and B11C. FIG. 4C shows a graph of the inhibition of human LAG-3 binding to Daudi cells by anti-LAG-3 mouse antibodies B6, B12, and B15. FIG. 4D shows a graph of the inhibition of human LAG-3 binding to Daudi cells by anti-LAG-3 mAb BG29 (human IgG4 heavy chain and kappa light chain chimeric).

FIG. 5A shows the effect of competition peptides (see Table 6) on human LAG-3 binding to anti-LAG-3 mAb B5 (human IgG4 heavy chain and kappa light chain chimeric; B5/IgG4) measured by ELISA. B5/IgG4 was preincubated with a competition peptide for 30 minutes. Then human LAG-3 extracellular domain (ECD) fused to mouse Fc (hLAG3-mFc) was added (the final peptide concentration was 600-fold that of hLAG3-mFc) and the mixture was incubated for 60 minutes before being added to an ELISA plate coated with anti-human IgG. The incubation was carried out at 4° C. overnight. After washing, the hLAG3-mFc bound to the immobilized B5/IgG4 on the ELISA plate was detected by adding anti-mouse IgG conjugated to horseradish peroxidase (HRP) and incubating for 60 minutes. Then, after washing, the ELISA was developed using One-step Detection Solution and measured as the absorbance at 450 nm. FIG. 5B shows a peptide dose-response graph of B5/IgG4 under the same condition in FIG. 5A. FIG. 5C shows the effect of competition peptides on human LAG-3 binding to B6 (human IgG4 heavy chain and kappa light chain chimeric; B6/IgG4) under the condition described in FIG. 5A. FIG. 5D shows a peptide dose-response graph for B6/IgG4 under the same condition described in FIG. 5A.

FIG. 9A shows the effect of competition peptides on human LAG-3 binding to anti-LAG-3 mAb B3 (human IgG1 heavy chain and kappa light chain chimeric) measured by ELISA as described in FIG. 5A except that the final peptide concentrations are as shown in the graph. FIG. 9B shows the effect of competition peptides on human LAG-3 binding to anti-LAG-3 mAb B4 (human IgG1 heavy chain and kappa light chain chimeric) under the condition in FIG. 9A.

FIG. 10A shows the $IC_{50}$ curve for B5(H1L4) in inhibiting LAG-3 binding to MHC class II molecules on Daudi cells. FIG. 10B shows the $IC_{50}$ curve for B7(H1L5) in inhibiting LAG-3 binding to MHC class II molecules on Daudi cells. FIG. 10C shows the $IC_{50}$ curve for B7(H1L8) in inhibiting LAG-3 binding to MHC class II molecules on Daudi cells.

DETAILED DESCRIPTION OF THE INVENTION

Figure 1A:
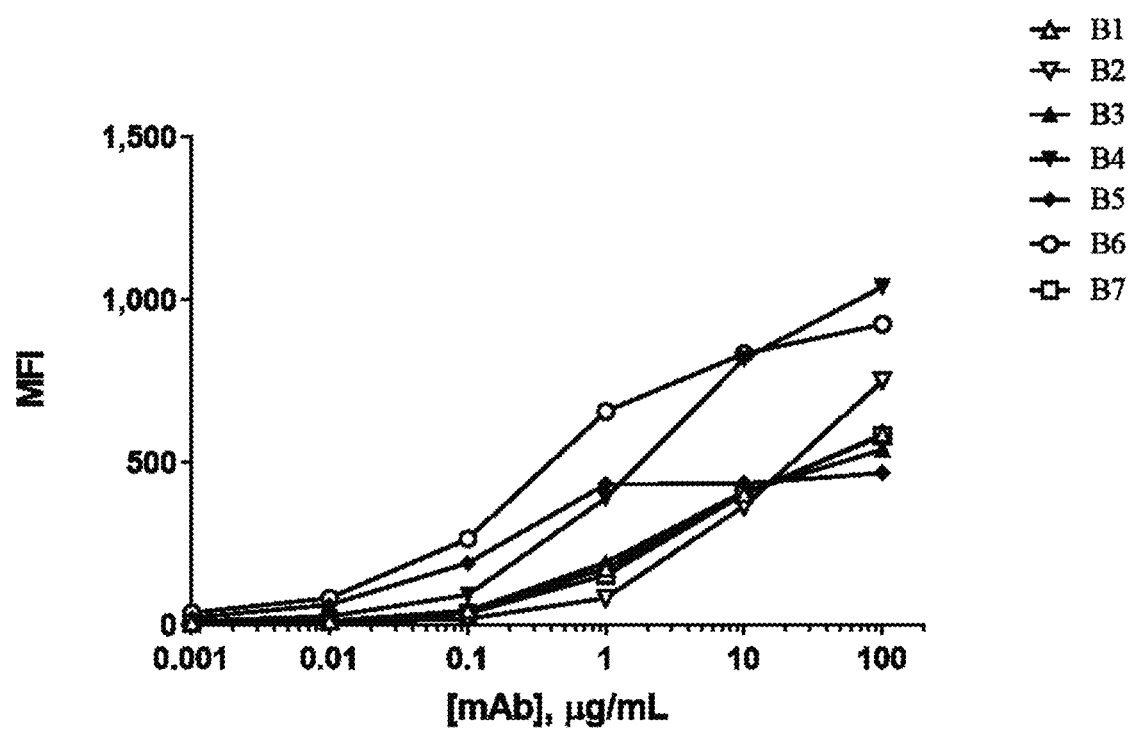
FIGS. 1A-1B show the binding of purified mouse anti-LAG-3 mAbs to CHO-S cells stably transfected with full-length human LAG-3 by FACS analysis.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially" of or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right," "left," "lower," and "upper" designate directions in the drawings to which reference is made.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-LAG-3 antibodies, LAG-3 polypeptides, and LAG-3 polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the terms "inhibit," "inhibiting," and "inhibition," mean to decrease an activity, response, condition, disease or other biological parameter. This can include, but is not limited to complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between, as compared to native or control levels. By way of a non-limiting example, an antibody of the invention can inhibit the activity of a LAG-3 protein. The activity of the LAG-3 protein can be reduced or ablated relative to the native LAG-3 protein activity. By way of another non-limiting example, an antibody of the invention can inhibit the binding of a LAG-3 protein to a MHC class II molecule and/or a LSECtin. The binding of LAG-3 to a MHC class II molecule and/or a LSECtin can be reduced or ablated relative to the native LAG-3 binding to the MHC class II molecule and/or LSECtin.

Antibodies

The invention generally relates to isolated anti-LAG-3 antibodies, nucleic acids and expression vectors encoding the antibodies, recombinant cells containing the vectors, and compositions comprising the antibodies. Methods of making the antibodies, and methods of using the antibodies to treat diseases including cancer, inflammatory diseases, autoimmune diseases, type 1 diabetes, and/or infectious diseases are also provided. The antibodies of the invention possess one or more desirable functional properties, including but not limited to high-affinity binding to LAG-3, high specificity to LAG-3, the ability to block the binding of LAG-3 to MHC class II molecules and/or LSECtin, the ability to stimulate the production of cytokines such as, but not limited to, IL-2 and IFN-γ, and the ability to inhibit tumor growth in animal models and subjects when administered alone or in combination with other anti-cancer therapies.

In a general aspect, the invention relates to isolated monoclonal antibodies or antigen-binding fragments thereof that bind LAG-3.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to LAG-3 is substantially free of antibodies that do not bind to LAG-3). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on LAG-3 and the second epitope is located on PD-1, PD-L1, TIM-3, CTLA-4, EGFR, HER-2, CD19, CD20, CD33, DLL-3, CD73, apelin, CD3, CD47, TIP-1, CLDN18.2, FOLR1 and/or other tumor associated immune suppressors or surface antigens.

As used herein, the term "LAG-3" refers to lymphocyte activation gene 3 (also known as CD223), which belongs to the Ig superfamily and contains 4 extracellular Ig-like domains. LAG-3 is expressed on the surface of activated T cells (Triebel, et al., J. Exp. Med. 1990; 171:1393-1405) and exhibits a unique inhibitory activity on T cells. LAG-3 is capable of binding to MHC class II molecules. Both LAG-3 and CD4 T cell co-receptor bind to MHC class II molecules at the same site, but the LAG-3 binding is of much higher affinity than that of CD4 (Huard, et al., Immunogenetics 1994; 39:213-217). Therefore, the expression of LAG-3 on T cells prevents the binding of CD4 to the MHC class II molecules on antigen presenting cells (APCs), inhibits the co-stimulatory activity of the MHC class II molecules, and negatively modulates the maintenance of T cell activities. When the binding of MHC class II molecules and LAG-3 is blocked with specific antibodies, more MHC class II molecules are available to bind CD4 which leads to T cell activation (Sierro et al., Expert Opin Ther Targets. 2011;15 (1):91-101). LAG-3 on the surface of T regulatory (Treg) cells also suppresses the activity of dendritic cells (DCs) through binding to MHC class II molecules (Huang, et al., Immunity 2004; 21:503-513; Liang, et al., J Immunol 2008; 180:5916-5926). Such backward signaling has the potential to further suppress immune response by downregulating the activity of DCs, and consequently downregulating the activation of naïve T cells and other LAG-3 negative immune cells whose activation and/or activity depend on DCs. LAG-3 is also expressed on the surface of natural killer cells (Baixeras, et al., J. Exp. Med 1992; 176:327-337), B cells (Kisielow, et al., Eur. J. Immunol. 2005; 35:2081-2088) and plasmacytoid dendritic cells (Workman, et al., J Immunol 2009; 182:1885-1891). The term "human LAG-3" refers to a LAG-3 originated from a human. An exemplary amino acid sequence of a human LAG-3 is represented in GenBank Accession No. NP 002277.4 (SEQ ID NO:152).

As used herein, an antibody that "specifically binds to LAG-3" refers to an antibody that binds to a LAG-3, preferably a human LAG-3, with a KD of $1 \times 10^{-7}$ M or less, preferably $1 \times 10^{-8}$ M or less, more preferably $5 \times 10^{-9}$ M or less, $1 \times 10^{-9}$ M or less, $5 \times 10^{-10}$ M or less, or $1 \times 10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a BIA-CORE® system, or by using bio-layer interferometry technology, such as an OCTET® RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

a. SEQ ID NOs:35, 36, 37, 86, 87, and 88, respectively;
  b. SEQ ID NOs:38, 39, 40, 89, 90, and 91, respectively;
  c. SEQ ID NOs:41, 42, 137, 138, 93, and 94, respectively;
  d. SEQ ID NOs:139, 140, 141, 142, 99, and 143, respectively;
  e. SEQ ID NOs:144, 145, 146, 147, 148, and 149, respectively;
  f. SEQ ID NOs:65, 66, 67, 116, 117, and 118, respectively;
  g. SEQ ID NOs:68, 69, 70, 119, 120, and 121, respectively;
  h. SEQ ID NOs:71, 72, 73, 122, 123, and 124, respectively;
  i. SEQ ID NOs:74, 75, 76, 125, 126, and 127, respectively;
  j. SEQ ID NOs:77, 78, 79, 128, 129, and 130, respectively; or
  k. SEQ ID NOs:80, 150, 151, 131, 132, and 133, respectively;

wherein the antibody or antigen-binding fragment thereof specifically binds LAG-3, preferably human LAG-3.

SEQ ID NO:137 is represented by the amino acid sequence ARGGYX$_1$DYVWFPY, wherein X$_1$ is an amino acid selected from the group consisting of Y and F.

SEQ ID NO:138 is represented by the amino acid sequence QSIX$_1$YSNGYTY, wherein X$_1$ is an amino acid selected from the group consisting of L and V.

SEQ ID NO:139 is represented by the amino acid sequence GYTX$_1$X$_2$X$_3$YY, wherein X$_1$ is an amino acid selected from the group consisting of F and L; X$_2$ is an amino acid selected from the group consisting of T and S; and X$_3$ is an amino acid selected from the group consisting of G and N.

SEQ ID NO:140 is represented by the amino acid sequence INPYNGDX$_1$, wherein X$_1$ is an amino acid selected from the group consisting of T and I.

SEQ ID NO:141 is represented by the amino acid sequence X$_1$RDDGYX$_2$VX$_3$X$_4$FDX$_5$, wherein X$_1$ is an amino acid selected from the group consisting of V and A; X$_2$ is an amino acid selected from the group consisting of H and Y; $X_3$ is an amino acid selected from the group consisting of R and Y; $X_4$ is an amino acid selected from the group consisting of F and Y; and $X_5$ is an amino acid selected from the group consisting of V, Y, and C.

SEQ ID NO:142 is represented by the amino acid sequence QDIX$_1$X$_2$X$_3$, wherein $X_1$ is an amino acid selected from the group consisting of S and G; $X_2$ is an amino acid selected from the group consisting of D and G; $X_3$ is an amino acid selected from the group consisting of Y, S, and R.

SEQ ID NO:143 is represented by the amino acid sequence LQX$_1$X$_2$X$_3$SPPT, wherein $X_1$ is an amino acid selected from the group consisting of Y, C, and N; $X_2$ is an amino acid selected from the group consisting of V and A; and $X_3$ is an amino acid selected from the group consisting of S and N.

SEQ ID NO:144 is represented by the amino acid sequence GYSFX$_1$DYN, wherein $X_1$ is an amino acid selected from the group consisting of S and T.

SEQ ID NO:145 is represented by the amino acid sequence IX$_1$LDX$_2$X$_3$X$_4$T, wherein $X_1$ is an amino acid selected from the group consisting of N and T; $X_2$ is an amino acid selected from the group consisting of S and Y; $X_3$ is an amino acid selected from the group consisting of A and G; and $X_4$ is an amino acid selected from the group consisting of A and T.

SEQ ID NO:146 is represented by the amino acid sequence AX$_1$YDY, wherein $X_1$ is an amino acid selected from the group consisting of S and C.

SEQ ID NO:147 is represented by the amino acid sequence QDISX$_1$Y, wherein $X_1$ is an amino acid selected from the group consisting of H and N.

SEQ ID NO:148 is represented by the amino acid sequence X$_1$TS, wherein $X_1$ is an amino acid selected from the group consisting of E and A.

SEQ ID NO:149 is represented by the amino acid sequence LQYAX$_1$YPLT, wherein $X_1$ is an amino acid selected from the group consisting of T and S.

SEQ ID NO:150 is represented by the amino acid sequence IYPGRGX$_1$P, wherein $X_1$ is an amino acid selected from the group consisting of D and N.

SEQ ID NO:151 is represented by the amino acid sequence EIYYGNYX$_1$DY, wherein $X_1$ is an amino acid selected from the group consisting of I and L.

According to another particular aspect, the invention relates to an isolated monoclonal antibody or antigen-binding fragment thereof comprising a heavy chain variable region having a polypeptide sequence at least 85%, preferably 90%, more preferably 95% or more, such as 95%, 96%, 97%, 98%, or 99% identical to one of SEQ ID NOs:1, 3, 5, 7, 9, 11, 13, 15, 17, 19, 21, 23, 25, 27, 29, 31, or 33, or a light chain variable region having a polypeptide sequence at least 85%, preferably 90%, more preferably 95% or more, such as 95%, 96%, 97%, 98%, or 99% identical to one of SEQ ID NOs:2, 4, 6, 8, 10, 12, 14, 16, 18, 20, 22, 24, 26, 28, 30, 32, or 34. According to one preferred embodiment, the isolated monoclonal antibody or antigen-binding fragment thereof of the invention comprises a heavy chain variable region having the polypeptide sequence at least 85%, preferably 90%, more preferably 95% or more, such as 95%, 96%, 97%, 98%, or 99% identical to SEQ ID NO:1, 3, 5, 7, 9, 11, 13, 15, 17, 19, 21, 23, 25, 27, 29, 31, or 33, and a light chain variable region having a polypeptide sequence at least 85%, preferably 90%, more preferably 95% or more, such as 95%, 96%, 97%, 98%, or 99% identical to SEQ ID NO:2, 4, 6, 8, 10, 12, 14, 16, 18, 20, 22, 24, 26, 28, 30, 32, or 34, respectively.

According to another particular aspect, the invention relates to an isolated monoclonal antibody or antigen-binding fragment thereof of the invention, comprising:

a. a heavy chain variable region having the polypeptide sequence of SEQ ID NO:1, and a light chain variable region having the polypeptide sequence of SEQ ID NO:2;

b. a heavy chain variable region having the polypeptide sequence of SEQ ID NO:3, and a light chain variable region having the polypeptide sequence of SEQ ID NO:4;

c. a heavy chain variable region having the polypeptide sequence of SEQ ID NO:5, and a light chain variable region having the polypeptide sequence of SEQ ID NO:6;

d. a heavy chain variable region having the polypeptide sequence of SEQ ID NO:7, and a light chain variable region having the polypeptide sequence of SEQ ID NO:8;

e. a heavy chain variable region having the polypeptide sequence of SEQ ID NO:9, and a light chain variable region having the polypeptide sequence of SEQ ID NO:10;

f. a heavy chain variable region having the polypeptide sequence of SEQ ID NO:11, and a light chain variable region having the polypeptide sequence of SEQ ID NO:12;

g. a heavy chain variable region having the polypeptide sequence of SEQ ID NO:13, and a light chain variable region having the polypeptide sequence of SEQ ID NO:14;

h. a heavy chain variable region having the polypeptide sequence of SEQ ID NO:15, and a light chain variable region having the polypeptide sequence of SEQ ID NO:16;

i. a heavy chain variable region having the polypeptide sequence of SEQ ID NO:17, and a light chain variable region having the polypeptide sequence of SEQ ID NO:18;

j. a heavy chain variable region having the polypeptide sequence of SEQ ID NO:19, and a light chain variable region having the polypeptide sequence of SEQ ID NO:20;

k. a heavy chain variable region having the polypeptide sequence of SEQ ID NO:21, and a light chain variable region having the polypeptide sequence of SEQ ID NO:22;

l. a heavy chain variable region having the polypeptide sequence of SEQ ID NO:23, and a light chain variable region having the polypeptide sequence of SEQ ID NO:24;

m. a heavy chain variable region having the polypeptide sequence of SEQ ID NO:25, and a light chain variable region having the polypeptide sequence of SEQ ID NO:26;

n. a heavy chain variable region having the polypeptide sequence of SEQ ID NO:27, and a light chain variable region having the polypeptide sequence of SEQ ID NO:28;

o. a heavy chain variable region having the polypeptide sequence of SEQ ID NO:29, and a light chain variable region having the polypeptide sequence of SEQ ID NO:30;

p. a heavy chain variable region having the polypeptide sequence of SEQ ID NO:31, and a light chain variable region having the polypeptide sequence of SEQ ID NO:32; or q. a heavy chain variable region having the polypeptide sequence of SEQ ID NO:33, and a light chain variable region having the polypeptide sequence of SEQ ID NO:34.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:35, 36, 37, 86, 87, and 88, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:38, 39, 40, 89, 90, and 91, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:41, 42, 43, 92, 93, and 94, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:44, 45, 46, 95, 96, and 97, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:47, 48, 49, 98, 99, and 100, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:50, 51, 52, 101, 102, and 103, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:53, 54, 55, 104, 105, and 106, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:56, 57, 58, 107, 108, and 109, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:59, 60, 61, 110, 111, and 112, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:62, 63, 64, 113, 114, and 115, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:19, and a light chain variable region having a polypeptide sequence at least 85%, preferably 90%, more preferably 95% or more, such as 95%, 96%, 97%, 98%, or 99% identical to SEQ ID NO:20. Preferably, the isolated monoclonal antibody or antigen-binding fragment thereof comprises a heavy chain variable region having the polypeptide sequence of SEQ ID NO:19; and a light chain variable region having the polypeptide sequence of SEQ ID NO:20.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:65, 66, 67, 116, 117, and 118, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:21, and a light chain variable region having a polypeptide sequence at least 85%, preferably 90%, more preferably 95% or more, such as 95%, 96%, 97%, 98%, or 99% identical to SEQ ID NO:22. Preferably, the isolated monoclonal antibody or antigen-binding fragment thereof comprises a heavy chain variable region having the polypeptide sequence of SEQ ID NO:21; and a light chain variable region having the polypeptide sequence of SEQ ID NO:22.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:68, 69, 70, 119, 120, and 121, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:23, and a light chain variable region having a polypeptide sequence at least 85%, preferably 90%, more preferably 95% or more, such as 95%, 96%, 97%, 98%, or 99% identical to SEQ ID NO:24. Preferably, the isolated monoclonal antibody or antigen-binding fragment thereof comprises a heavy chain variable region having the polypeptide sequence of SEQ ID NO:23; and a light chain variable region having the polypeptide sequence of SEQ ID NO:24.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:71, 72, 73, 122, 123, and 124, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:25, and a light chain variable region having a polypeptide sequence at least 85%, preferably 90%, more preferably 95% or more, such as 95%, 96%, 97%, 98%, or 99% identical to SEQ ID NO:26. Preferably, the isolated monoclonal antibody or antigen-binding fragment thereof comprises a heavy chain variable region having the polypeptide sequence of SEQ ID NO:25; and a light chain variable region having the polypeptide sequence of SEQ ID NO:26.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:74, 75, 76, 125, 126, and 127, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:27, and a light chain variable region having a polypeptide sequence at least 85%, preferably 90%, more preferably 95% or more, such as 95%, 96%, 97%, 98%, or 99% identical to SEQ ID NO:28. Preferably, the isolated monoclonal antibody or antigen-binding fragment thereof comprises a heavy chain variable region having the polypeptide sequence of SEQ ID NO:27; and a light chain variable region having the polypeptide sequence of SEQ ID NO:28.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:77, 78, 79, 128, 129, and 130, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:29, and a light chain variable region having a polypeptide sequence at least 85%, preferably 90%, more preferably 95% or more, such as 95%, 96%, 97%, 98%, or 99% identical to SEQ ID NO:30. Preferably, the isolated monoclonal antibody or antigen-binding fragment thereof comprises a heavy chain variable region having the polypeptide sequence of SEQ ID NO:29; and a light chain variable region having the polypeptide sequence of SEQ ID NO:30.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:80, 81, 82, 131, 132, and 133, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:31, and a light chain variable region having a polypeptide sequence at least 85%, preferably 90%, more preferably 95% or more, such as 95%, 96%, 97%, 98%, or 99% identical to SEQ ID NO:32. Preferably, the isolated monoclonal antibody or antigen-binding fragment thereof comprises a heavy chain variable region having the polypeptide sequence of SEQ ID NO:31; and a light chain variable region having the polypeptide sequence of SEQ ID NO:32.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs:83, 84, 85, 134, 135, and 136, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:33, and a light chain variable region having a polypeptide sequence at least 85%, preferably 90%, more preferably 95% or more, such as 95%, 96%, 97%, 98%, or 99% identical to SEQ ID NO:34. Preferably, the isolated monoclonal antibody or antigen-binding fragment thereof comprises a heavy chain variable region having the polypeptide sequence of SEQ ID NO:33; and a light chain variable region having the polypeptide sequence of SEQ ID NO:34.

According to another particular aspect, the invention relates to an isolated monoclonal antibody or antigen-binding fragment thereof to LAG-3 that specifically binds to an epitope comprising the amino acid sequence of SEQ ID NO:192. According to another particular aspect, the invention relates to an isolated monoclonal antibody or antigen-binding fragment thereof to LAG-3 that specifically binds to an epitope comprising the amino acid sequence of SEQ ID NO:193. According to another particular aspect, the invention relates to an isolated monoclonal antibody or antigen-binding fragment thereof to LAG-3 that specifically binds to an epitope comprising the amino acid sequence of SEQ ID NO:158. According to another particular aspect, the invention relates to an isolated monoclonal antibody or antigen-binding fragment thereof to LAG-3 that specifically binds to an epitope comprising the amino acid sequence of SEQ ID NO:180. According to another particular aspect, the invention relates to an isolated monoclonal antibody or antigen-binding fragment thereof to LAG-3 that specifically binds to an epitope comprising the amino acid sequence of SEQ ID NO:194. The isolated monoclonal antibodies or antigen-binding fragments thereof can, for example, inhibit LAG-3 activity.

According to another particular aspect, the invention relates to an isolated monoclonal antibody or antigen-binding fragment thereof, wherein the antibody or antigen-binding fragment thereof is capable of blocking binding of LAG-3 to WIC class II molecules.

According to another particular aspect, the invention relates to an isolated monoclonal antibody or antigen-binding fragment thereof, wherein the antibody or antigen-binding fragment thereof is capable of blocking binding of LAG-3 to LSECtin.

According to another particular aspect, the invention relates to an isolated monoclonal antibody or antigen-binding fragment thereof, wherein the antibody or antigen-binding fragment thereof is chimeric.

According to another particular aspect, the invention relates to an isolated monoclonal antibody or antigen-binding fragment thereof, wherein the antibody or antigen-binding fragment thereof is human or humanized.

According to another particular aspect, the invention relates to an isolated humanized monoclonal antibody or antigen-binding fragment thereof, wherein the antibody or antigen-binding fragment thereof comprises:

a. a heavy chain variable region having the polypeptide sequence of SEQ ID NO:195, and a light chain variable region having the polypeptide sequence of SEQ ID NO:208 b. a heavy chain variable region having the polypeptide sequence of SEQ ID NO:196, and a light chain variable region having the polypeptide sequence of SEQ ID NO:206;

c. a heavy chain variable region having the polypeptide sequence of SEQ ID NO:197, and a light chain variable region having the polypeptide sequence of SEQ ID NO:205;

d. a heavy chain variable region having the polypeptide sequence of SEQ ID NO:197, and a light chain variable region having the polypeptide sequence of SEQ ID NO:206;

e. a heavy chain variable region having the polypeptide sequence of SEQ ID NO:197, and a light chain variable region having the polypeptide sequence of SEQ ID NO:207;

f. a heavy chain variable region having the polypeptide sequence of SEQ ID NO:198, and a light chain variable region having the polypeptide sequence of SEQ ID NO:205;

g. a heavy chain variable region having the polypeptide sequence of SEQ ID NO:199, and a light chain variable region having the polypeptide sequence of SEQ ID NO:209;

h. a heavy chain variable region having the polypeptide sequence of SEQ ID NO:200, and a light chain variable region having the polypeptide sequence of SEQ ID NO:209;

i. a heavy chain variable region having the polypeptide sequence of SEQ ID NO:201, and a light chain variable region having the polypeptide sequence of SEQ ID NO:209;

j. a heavy chain variable region having the polypeptide sequence of SEQ ID NO:202, and a light chain variable region having the polypeptide sequence of SEQ ID NO:209;

k. a heavy chain variable region having the polypeptide sequence of SEQ ID NO:203, and a light chain variable region having the polypeptide sequence of SEQ ID NO:209;

l. a heavy chain variable region having the polypeptide sequence of SEQ ID NO:204, and a light chain variable region having the polypeptide sequence of SEQ ID NO:209;

m. a heavy chain variable region having the polypeptide sequence of SEQ ID NO:199, and a light chain variable region having the polypeptide sequence of SEQ ID NO:210;

n. a heavy chain variable region having the polypeptide sequence of SEQ ID NO:200, and a light chain variable region having the polypeptide sequence of SEQ ID NO:210;

o. a heavy chain variable region having the polypeptide sequence of SEQ ID NO:201, and a light chain variable region having the polypeptide sequence of SEQ ID NO:210;

p. a heavy chain variable region having the polypeptide sequence of SEQ ID NO:202, and a light chain variable region having the polypeptide sequence of SEQ ID NO:210;

q. a heavy chain variable region having the polypeptide sequence of SEQ ID NO:203, and a light chain variable region having the polypeptide sequence of SEQ ID NO:210; or r. a heavy chain variable region having the polypeptide sequence of SEQ ID NO:204, and a light chain variable region having the polypeptide sequence of SEQ ID NO:210.

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier may be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation may comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition may be formulated as an injectable which can be injected, for example, via an injection device (e.g., a syringe or an infusion pump). The injection may be delivered subcutaneously, intramuscularly, intraperitoneally, intravitreally, or intravenously, for example.

In another embodiment, the pharmaceutical composition is a solid formulation, e.g., a freeze-dried or spray-dried composition, which may be used as is, or whereto the physician or the patient adds solvents, and/or diluents prior to use. Solid dosage forms may include tablets, such as compressed tablets, and/or coated tablets, and capsules (e.g., hard or soft gelatin capsules). The pharmaceutical composition may also be in the form of sachets, dragees, powders, granules, lozenges, or powders for reconstitution, for example.

The dosage forms may be immediate release, in which case they may comprise a water-soluble or dispersible carrier, or they may be delayed release, sustained release, or modified release, in which case they may comprise water-insoluble polymers that regulate the rate of dissolution of the dosage form in the gastrointestinal tract or under the skin.

In other embodiments, the pharmaceutical composition may be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer may be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative may be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent may be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent may be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer may be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant may, for example, be selected from the group consisting of anionic surfactants, cationic surfactants, nonionic surfactants, and/or zwitterionic surfactants. The surfactant may be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor may be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of blocking the binding of LAG-3 to MHC class II molecules in a subject, the method comprising administering to the subject an isolated monoclonal antibody or antigen binding fragment thereof that specifically binds LAG-3 or a pharmaceutical composition of the invention.

In another general aspect, the invention relates to a method of blocking the binding of LAG-3 to LSECtin in a subject, the method comprising administering to the subject an isolated monoclonal antibody or antigen binding fragment thereof that specifically binds LAG-3 or a pharmaceutical composition of the invention.

The functional activity of antibodies and antigen-binding fragments thereof that bind LAG-3 can be characterized by methods known in the art and as described herein. Methods for characterizing antibodies and antigen-binding fragments thereof that bind LAG-3 include, but are not limited to, affinity and specificity assays including BIACORE®, ELISA, and OCTETRED® analysis; receptor ligand binding assays to detect blocking of the binding of LAG-3 to MEW class II molecules on Daudi cells by FACS; surface plasmon resonance (SPR) assay to determine the interaction between LSECtin and LAG-3 (Xu, et al., Cancer Res 2014; 74:3418-3428), and the blocking effect by an anti-LAG-3 mAb; the functional activity of an anti-LAG-3 mAb can also be assessed in a Mixed Lymphocyte Reaction (MLR) assay, wherein dendritic cells and peripheral blood mononuclear cells (PBMCs) from different donors are mixed in the presence of the mAb and stimulation of cytokine secretion is measured. According to particular embodiments, the methods for characterizing antibodies and antigen-binding fragments thereof that bind LAG-3 include those described below.

In another general aspect, the invention relates to a method of treating a cancer in a subject in need thereof, comprising administering to the subject an isolated monoclonal antibody or antigen binding fragment thereof that specifically binds LAG-3 or a pharmaceutical composition of the invention. The cancer can, for example, be selected from but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

In another general aspect, the invention relates to a method of treating an infectious disease in a subject in need thereof, comprising administering to the subject an isolated monoclonal antibody or antigen binding fragment thereof that specifically binds LAG-3 or a pharmaceutical composition of the invention.

In another general aspect, the invention relates to a method of treating an inflammatory disease in a subject in need thereof, comprising administering to the subject an isolated monoclonal antibody or antigen binding fragment thereof that specifically binds LAG-3 or a pharmaceutical composition of the invention.

In another general aspect, the invention relates to a method of treating an autoimmune disease in a subject in need thereof, comprising administering to the subject an isolated monoclonal antibody or antigen binding fragment thereof that specifically binds LAG-3 or a pharmaceutical composition of the invention.

In another general aspect, the invention relates to a method of treating a type 1 diabetes in a subject in need thereof, comprising administering to the subject an isolated monoclonal antibody or antigen binding fragment thereof that specifically binds LAG-3 or a pharmaceutical composition of the invention.

According to embodiments of the invention, the pharmaceutical composition comprises a therapeutically effective amount of an anti-LAG-3 antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-LAG-3 antibodies or antigen-binding fragments thereof, a therapeutically effective amount means an amount of the anti-LAG-3 antibody or antigen-binding fragment thereof that modulates an immune response in a subject in need thereof. Also as used herein with reference to anti-LAG-3 antibodies or antigen-binding fragments thereof, a therapeutically effective amount means an amount of the anti-LAG-3 antibody or antigen-binding fragment thereof that results in treatment of a disease, disorder, or condition; prevents or slows the progression of the disease, disorder, or condition; or reduces or completely alleviates symptoms associated with the disease, disorder, or condition.

According to particular embodiments, the disease, disorder or condition to be treated is cancer, preferably a cancer selected from the group consisting of a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors. According to other particular embodiments, the disease, disorder or condition to be treated is an infectious disease, an inflammatory disease, an immune disease, an autoimmune disease, and/or a type 1 diabetes.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer, an infectious disease, disorder or condition, an immune disease, disorder or condition, an autoimmune disease, disorder or condition, an inflammatory disease, disorder or condition, and/or a type 1 diabetes, disorder or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, a composition used in the treatment of a cancer, an infectious disease, disorder or condition, an immune disease, disorder or condition, an autoimmune disease, disorder or condition, a type 1 diabetes, disorder or condition, and/or an inflammatory disease, disorder or condition. For cancer therapy, it can be used in combination with another treatment including, but not limited to, a chemotherapy, an anti-CD20 mAb, an anti-TIM-3 mAb, an anti-CTLA-4 antibody, an anti-EGFR mAb, an anti-HER-2 mAb, an anti-CD19 mAb, an anti-CD33 mAb, an anti-CD73 mAb, an anti-CD47 mAb, an anti-DLL-3 mAb, an anti-apelin mAb, an anti-TIP-1 mAb, an anti-CLDN18.2 mAb, an anti-FOLR1 mAb, an anti-PD-L1 antibody, an anti-PD-1 antibody, a PD-1/PD-L1 therapy, other immuno-oncology drugs, an antiangiogenic agent, a radiation therapy, an antibody-drug conjugate (ADC), a targeted therapy, or other anticancer drugs. Anti-LAG-3 antibodies can be used to construct bispecific antibodies with partner mAbs against PD-1, PD-L1, CD47, TIM-3, CTLA-4, EGFR, HER-2, CD19, CD20, CD33, CD73, apelin, DLL-3, claudin18.2, TIP-1, CD3, folate receptor alpha (FOLR1) and/or other tumor surface antigens to treat cancers/tumors that express both LAG-3 and the specific tumor associated antigen.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of LAG-3 in a subject. The methods comprise (a) obtaining a sample from the subject; (b) contacting the sample with a monoclonal antibody or antigen-binding fragment thereof of the invention; and (c) determining a level of LAG-3 in the subject.

As used herein, "sample" refers to a biological sample isolated from a subject and can include, but is not limited to, whole blood, serum, plasma, blood cells, endothelial cells, tissue biopsies (e.g., a cancer tissue), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma. A "blood sample" can, for example, comprise cancer cells.

In certain embodiments, the level of LAG-3 in the subject can be determined utilizing assays selected from, but not limited to, a Western blot assay, an ELISA assay, a FACS assay, and/or a radioimmunoassay (RIA). Relative protein levels can be determined by utilizing Western blot analysis, FACS assay, and immunohistochemistry (IHC), and absolute protein levels can be determined by utilizing an ELISA assay. When determining the relative levels of LAG-3, the levels of LAG-3 can be determined between at least two samples, e.g., between samples from the same subject at different time points, between samples from different tissues in the same subject, and/or between samples from different subjects. Alternatively, when determining absolute levels of LAG-3, such as by an ELISA assay, the absolute level of LAG-3 in the sample can be determined by creating a standard for the ELISA assay prior to testing the sample. A person skilled in the art would understand which analytical techniques to utilize to determine the level of LAG-3 in a sample from the subject utilizing the antibodies or antigen-binding fragments thereof of the invention.

Utilizing methods of determining a level of LAG-3 in a sample from a subject can lead to the diagnosis of abnormal (elevated, reduced, or insufficient) LAG-3 levels in a disease and making appropriate therapeutic decisions. Such a disease can be selected from, but not limited to, a cancer, an infectious disease, an inflammatory disease, an autoimmune disease, and/or type 1 diabetes. Additionally, by monitoring the levels of LAG-3 in a subject, the risk of developing a disease as indicated above can be determined based on the knowledge of the level of LAG-3 in a particular disease and/or during the progression of the particular disease.

EMBODIMENTS

The invention provides also the following non-limiting embodiments.

Embodiment 1 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of
- a. SEQ ID NOs:35, 36, 37, 86, 87, and 88, respectively;
- b. SEQ ID NOs:38, 39, 40, 89, 90, and 91, respectively;
- c. SEQ ID NOs:41, 42, 137, 138, 93, and 94, respectively;
- d. SEQ ID NOs:139, 140, 141, 142, 99, and 143, respectively;
- e. SEQ ID NOs:144, 145, 146, 147, 148, and 149, respectively;
- f. SEQ ID NOs:65, 66, 67, 116, 117, and 118, respectively;
- g. SEQ ID NOs:68, 69, 70, 119, 120, and 121, respectively;
- h. SEQ ID NOs:71, 72, 73, 122, 123, and 124, respectively;
- i. SEQ ID NOs:74, 75, 76, 125, 126, and 127, respectively;
- j. SEQ ID NOs:77, 78, 79, 128, 129, and 130, respectively; or
- k. SEQ ID NOs:80, 150, 151, 131, 132, and 133, respectively;

wherein the antibody or antigen-binding fragment thereof specifically binds LAG-3, preferably specifically binds human LAG-3.

Embodiment 2 is the isolated monoclonal antibody or antigen-binding fragment of embodiment 1, comprising a heavy chain variable region having a polypeptide sequence at least 95% identical to SEQ ID NO:1, 3, 5, 7, 9, 11, 13, 15, 17, 19, 21, 23, 25, 27, 29, 31, or 33, or a light chain variable region having a polypeptide sequence at least 95% identical to SEQ ID NO:2, 4, 6, 8, 10, 12, 14, 16, 18, 20, 22, 24, 26, 28, 30, 32, or 34.

Embodiment 3 is the isolated monoclonal antibody or antigen-binding fragment of embodiment 1 or 2, comprising
- (a) a heavy chain variable region having the polypeptide sequence of SEQ ID NO:1, and a light chain variable region having the polypeptide sequence of SEQ ID NO:2;
- (b) a heavy chain variable region having the polypeptide sequence of SEQ ID NO:3, and a light chain variable region having the polypeptide sequence of SEQ ID NO:4;
- (c) a heavy chain variable region having the polypeptide sequence of SEQ ID NO:5, and a light chain variable region having the polypeptide sequence of SEQ ID NO:6;
- (d) a heavy chain variable region having the polypeptide sequence of SEQ ID NO:7, and a light chain variable region having the polypeptide sequence of SEQ ID NO:8;
- (e) a heavy chain variable region having the polypeptide sequence of SEQ ID NO:9, and a light chain variable region having the polypeptide sequence of SEQ ID NO:10;
- (f) a heavy chain variable region having the polypeptide sequence of SEQ ID NO:11, and a light chain variable region having the polypeptide sequence of SEQ ID NO:12;
- (g) a heavy chain variable region having the polypeptide sequence of SEQ ID NO:13, and a light chain variable region having the polypeptide sequence of SEQ ID NO:14;
- (h) a heavy chain variable region having the polypeptide sequence of SEQ ID NO:15, and a light chain variable region having the polypeptide sequence of SEQ ID NO:16;
- (i) a heavy chain variable region having the polypeptide sequence of SEQ ID NO:17, and a light chain variable region having the polypeptide sequence of SEQ ID NO:18;
- (j) a heavy chain variable region having the polypeptide sequence of SEQ ID NO:19, and a light chain variable region having the polypeptide sequence of SEQ ID NO:20;
- (k) a heavy chain variable region having the polypeptide sequence of SEQ ID NO:21, and a light chain variable region having the polypeptide sequence of SEQ ID NO:22;
- (l) a heavy chain variable region having the polypeptide sequence of SEQ ID NO:23, and a light chain variable region having the polypeptide sequence of SEQ ID NO:24;
- (m) a heavy chain variable region having the polypeptide sequence of SEQ ID NO:25, and a light chain variable region having the polypeptide sequence of SEQ ID NO:26;
- (n) a heavy chain variable region having the polypeptide sequence of SEQ ID NO:27, and a light chain variable region having the polypeptide sequence of SEQ ID NO:28;
- (o) a heavy chain variable region having the polypeptide sequence of SEQ ID NO:29, and a light chain variable region having the polypeptide sequence of SEQ ID NO:30;
- (p) a heavy chain variable region having the polypeptide sequence of SEQ ID NO:31, and a light chain variable region having the polypeptide sequence of SEQ ID NO:32; or
- (q) a heavy chain variable region having the polypeptide sequence of SEQ ID NO:33, and a light chain variable region having the polypeptide sequence of SEQ ID NO:34.

Embodiment 4 is an isolated monoclonal antibody or antigen-binding fragment thereof to LAG-3 that specifically binds to an epitope comprising the amino acid sequence of SEQ ID NO:192.

Embodiment 5 is an isolated monoclonal antibody or antigen-binding fragment thereof of LAG-3 that specifically binds to an epitope comprising the amino acid sequence of SEQ ID NO:193.

Embodiment 6 is an isolated monoclonal antibody or antigen-binding fragment thereof of LAG-3 that specifically binds to an epitope comprising the amino acid sequence of SEQ ID NO:158.

Embodiment 7 is an isolated monoclonal antibody or antigen-binding fragment thereof of LAG-3 that specifically binds to an epitope comprising the amino acid sequence of SEQ ID NO:180.

Embodiment 8 is an isolated monoclonal antibody or antigen-binding fragment thereof of LAG-3 that specifically binds to an epitope comprising the amino acid sequence of SEQ ID NO:194.

Embodiment 9 is the isolated monoclonal antibody or antigen-binding fragment thereof of any one of embodiments 1-8, wherein the monoclonal antibody or antigen-binding fragment thereof inhibits LAG-3 activity.

Embodiment 10 is the isolated monoclonal antibody or antigen-binding fragment thereof of any one of embodiments 1-8, wherein the monoclonal antibody or antigen-binding fragment thereof is capable of blocking binding of LAG-3 to MEW class II molecules.

Embodiment 11 is the isolated monoclonal antibody or antigen-binding fragment thereof of any one of embodiments 1-8, wherein the monoclonal antibody or antigen-binding fragment thereof is capable of blocking binding of LAG-3 to LSECtin.

Embodiment 12 is the isolated monoclonal antibody or antigen-binding fragment of any one of embodiments 1-11, wherein the antibody or antigen-binding fragment thereof is chimeric.

Embodiment 13 is the isolated monoclonal antibody or antigen-binding fragment of any one of embodiments 1-11, wherein the antibody or antigen-binding fragment thereof is human or humanized.

Embodiment 14 is the isolated monoclonal antibody or antigen-binding fragment thereof of embodiment 13, wherein the antibody or antigen-binding fragment thereof comprises:
  a. a heavy chain variable region having the polypeptide sequence of SEQ ID NO:195, and a light chain variable region having the polypeptide sequence of SEQ ID NO:208;
  b. a heavy chain variable region having the polypeptide sequence of SEQ ID NO:196, and a light chain variable region having the polypeptide sequence of SEQ ID NO:206;
  c. a heavy chain variable region having the polypeptide sequence of SEQ ID NO:197 and a light chain variable region having the polypeptide sequence of SEQ ID NO:205;
  d. a heavy chain variable region having the polypeptide sequence of SEQ ID NO:197, and a light chain variable region having the polypeptide sequence of SEQ ID NO:206;
  e. a heavy chain variable region having the polypeptide sequence of SEQ ID NO:197, and a light chain variable region having the polypeptide sequence of SEQ ID NO:207;
  f. a heavy chain variable region having the polypeptide sequence of SEQ ID NO:198, and a light chain variable region having the polypeptide sequence of SEQ ID NO:205;
  g. a heavy chain variable region having the polypeptide sequence of SEQ ID NO:199, and a light chain variable region having the polypeptide sequence of SEQ ID NO:209;
  h. a heavy chain variable region having the polypeptide sequence of SEQ ID NO:200, and a light chain variable region having the polypeptide sequence of SEQ ID NO:209;
  i. a heavy chain variable region having the polypeptide sequence of SEQ ID NO:201, and a light chain variable region having the polypeptide sequence of SEQ ID NO:209;
  j. a heavy chain variable region having the polypeptide sequence of SEQ ID NO:202, and a light chain variable region having the polypeptide sequence of SEQ ID NO:209;
  k. a heavy chain variable region having the polypeptide sequence of SEQ ID NO:203, and a light chain variable region having the polypeptide sequence of SEQ ID NO:209;
  l. a heavy chain variable region having the polypeptide sequence of SEQ ID NO:204, and a light chain variable region having the polypeptide sequence of SEQ ID NO:209;
  m. a heavy chain variable region having the polypeptide sequence of SEQ ID NO:199, and a light chain variable region having the polypeptide sequence of SEQ ID NO:210;
  n. a heavy chain variable region having the polypeptide sequence of SEQ ID NO:200, and a light chain variable region having the polypeptide sequence of SEQ ID NO:210;
  o. a heavy chain variable region having the polypeptide sequence of SEQ ID NO:201, and a light chain variable region having the polypeptide sequence of SEQ ID NO:210;
  p. a heavy chain variable region having the polypeptide sequence of SEQ ID NO:202, and a light chain variable region having the polypeptide sequence of SEQ ID NO:210;
  q. a heavy chain variable region having the polypeptide sequence of SEQ ID NO:203, and a light chain variable region having the polypeptide sequence of SEQ ID NO:210; or
  r. a heavy chain variable region having the polypeptide sequence of SEQ ID NO:204, and a light chain variable region having the polypeptide sequence of SEQ ID NO:210.

Embodiment 15 is an isolated nucleic acid encoding the monoclonal antibody or antigen-binding fragment of any one of embodiments 1-14.

Embodiment 16 is a vector comprising the isolated nucleic acid of embodiment 15.

Embodiment 17 is a host cell comprising the vector of embodiment 16.

Embodiment 18 is a pharmaceutical composition, comprising the isolated monoclonal antibody or antigen-binding fragment of any one of embodiments 1-14 and a pharmaceutically acceptable carrier.

Embodiment 19 is a method of blocking binding of LAG-3 to MHC class II molecules in a subject in need thereof, comprising administering to the subject the pharmaceutical composition of embodiment 18.

Embodiment 20 is a method of blocking binding of LAG-3 to LSECtin in a subject in need thereof, comprising administering to the subject the pharmaceutical composition of claim 18.

Embodiment 21 is a method of treating cancer in a subject in need thereof, comprising administering to the subject the pharmaceutical composition of embodiment 18.

Embodiment 22 is a method of treating an infectious disease in a subject in need thereof, comprising administering to the subject the pharmaceutical composition of embodiment 18.

Embodiment 23 is a method of treating an inflammatory disease in a subject in need thereof, comprising administering to the subject the pharmaceutical composition of embodiment 18.

Embodiment 24 is a method of treating an autoimmune disease in a subject in need thereof, comprising administering to the subject the pharmaceutical composition of embodiment 18.

Embodiment 25 is a method of treating type 1 diabetes in a subject in need thereof, comprising administering to the subject the pharmaceutical composition of embodiment 18.

Embodiment 26 is a method of producing the monoclonal antibody or antigen-binding fragment of any one of embodiments 1-14, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

Embodiment 27 is a method of producing a pharmaceutical composition comprising the monoclonal antibody or antigen-binding fragment of any one of embodiments 1-14, comprising combining the monoclonal antibody or antigen-binding fragment with a pharmaceutically acceptable carrier to obtain the pharmaceutical composition.

Embodiment 28 is a method of determining a level of LAG-3 in a subject, the method comprising:
a. obtaining a sample from the subject;
b. contacting the sample with the isolated monoclonal antibody or antigen-binding fragment thereof of any one of embodiments 1-14; and
c. determining a level of LAG-3 in the subject.

Embodiment 29 is the method of embodiment 28, wherein the sample is a tissue sample.

Embodiment 30 is the method of embodiment 29, wherein the tissue sample is a cancer tissue sample.

Embodiment 31 is the method of embodiment 28, wherein the sample is a blood sample.

EXAMPLES

Example 1: Identification of Anti-LAG-3 Monoclonal Antibodies

Mice were immunized with Fc-tagged human LAG-3 (ECD)-huFc, a fusion protein containing the extracellular domain (ECD) of human LAG-3 and human Fc (huFc) at the C-terminus. Plasma titer was determined by ELISA and confirmed by fluorescence-activated cell sorting (FACS). After euthanization, spleens and lymph nodes were collected to produce hybridomas. Hybridomas were grown in 96-well tissue culture plates and supernatants from individual wells were screened by ELISA using LAG-3(ECD)-huFc. Positive clones were further analyzed by FACS using CHO cells expressing human LAG-3. Top positive clones were isolated and sequenced.

Sequences of heavy and light chain variable regions for anti-LAG-3 monoclonal antibodies are provided in Tables 1 and 2, and the CDR regions for the anti-LAG-3 monoclonal antibodies are provided in Tables 3 and 4.

TABLE 1

Sequences of heavy chain variable regions for anti-LAG-3 mAbs

| mAb clones | VH |
|---|---|
| B1 | DVQLQESGPGLVKPSQSLSLTCTVTGYSITSDYAWNWIRQFPGNKLEWMGYIDY SGITSYNPSLKSRISITRDTSKNQFFLQLNSVTTEDTATYYCAREDHYDLAWFAY WGQGTLVTVSA (SEQ ID NO: 1) |
| B2 | QVHLQQSGPQLVKPGASVKISCKASGYTFTDYYINWVKQRPGQGLEWIGWIFPG SGSTYYNEKFKGKATLTVDKSSSTAYMLLSSLTSEDSAVYFCVRIHFDYDWFFD VWGTGTTVTVSS (SEQ ID NO: 3) |
| B3 | QVQLQQPGAELLKPGASVKMSCKASGYTFTSYDIHWLKQTPGQGLEWIGAIYPE NGDSSYSQKFKDKATLTADKSSNTAYIHLSSLTSEDSAVYYCARGGYYDYVWF PYWGQGTLVTVSA (SEQ ID NO: 5) |
| B4 | QVQLQQPGAELLKPGASVKMSCKASGYTFTSYDIHWLKQTPGQGLEWIGAIYPE NGDSSYSQKFKGKATLTADKSSNTAYIHLSSLTSEDSAVYYCARGGYFDYVWFP YWGQGTLVTVSA (SEQ ID NO: 7) |
| B5 | EVQLRQSGPVLVKPGASVKMSCKASGYTFTGYYMNWMKQSHGKSLEWLAVIN PYNGDTAYNRKFKGRAILTVDKSSSTAYMELNSLTSEDSAVYYCVRDDGYHVR FFDVWGTGTTVTVSS (SEQ ID NO: 9) |
| B9 | EVQLRQSGPVLVKPGASVKMSCKASGYTFTGYYMNWVKQSHGKSLEWLAVIN PYNGDTAYNRKFKGRATLTVDKSSSTAYMELNRLTSEDSAVYYCVRDDGYHV RYFDVWGTGTTVTVSS (SEQ ID NO: 11) |
| B6 | EVQLQQSGPVLVKPGASVKMSCKASGYTLSNYYMNWVKQSHGKSLEWIGVINP YNGDTAYNLKFKGKATLTADLSSNTAYMDFNSLTSEDSAVYYCARDDGYHVY YFDYWGQGTTLTVSS (SEQ ID NO: 13) |
| B11 | EVQLQQSGPVLVRPGASVKMSCKASGYTFTNYYMNWVKQSHGKSLEWIGVINP YNGDIAYSQKFKGKATLTVDKSSSTAYMELKSLTSEDSAVYYCARDDGYYVYY FDCWGQGTTLTVSS (SEQ ID NO: 15) |
| B7 | EFQLQQSGPELVKPGASVKISCKASGYSFSDYNLNWVKQSNGKTLEWIGLINLD SAATVYNQKFKGKATLTIDQSSTTAYMQLNSLTSDDSAVYYCASYDYWGQGTT LTVSS (SEQ ID NO: 17) |
| B10 | EFQLQQSGPELVKPGASVKISCKASGYSFTDYNLNWVKESNGKSLEWIGLITLDY GTTIYNQKFKGKATLTVDQSSSIAYMQLNSLTSDDSAVYYCACYDYWGQGTTL TVSS (SEQ ID NO: 19) |

TABLE 1-continued

Sequences of heavy chain variable regions for anti-LAG-3 mAbs

| mAb clones | VH |
|---|---|
| B12 | EVKLLESGGSLVQPGGSLKLSCAASGFDFSRYWMSWVRQAPGKGLEWIGEINPD SSTINYTPSLRDEFIISRDNAKNTLFLQMSKVISEDTALYYCARITSGYYFDYWGQ GTTLTVSS (SEQ ID NO: 21) |
| B13 | EVMLVESGGGLVKPGGSLKVSCAASGFTFSIYAMCWVRQTPEKRLEWVATISSG GSNTYYPDSVKGRFTISRDNAKNTLYLQMSSLRSEDTAVYYCARGDVYYDYDG RGFDYWGQGTTLTVSS (SEQ ID NO: 23) |
| B15 | EVQLQQSGAELVRPGASVKLSCTASGFNIKDDYMFWVKQRPEQGLEWIGWIDP ENGDTEYASKFQGKATITADTSSNTAYLQLSSLTSEDTAVYYCTLYAYWGQGTL VTVSA (SEQ ID NO: 25) |
| B16 | EVQLHQSGPVLVKPGASVKMSCKASGYTFTDYYMNWVKQSHGKSLEWIGVINP YNGRTSYNLKFKGKATLTVDKSSSTAYMDLNSLTSEDSAVYYCASPEGYWGQG TTLTVSS (SEQ ID NO: 27) |
| BG27 | QAYLQQSGADLVRPGASVKMSCKASGYTFTSYDMHWVKQTPRQGLEWIGAIY PGNGDASYNQKFKGKATLTVDKASSTAFMQLSSLTSEDSAVYFCARGDYGNYV WFAYWGQGTLVTVSA (SEQ ID NO: 29) |
| BG29 | QIQLQQSGPEVVKPGASVRISCKASGYTFSDYHINWVKQKPGQGLEWIGWIYPG RGDPEYNEKFKGKATLTVDRSASTAYMQLSSLTSEDTSVYFCEIYYGNYIDYWG QGTTLTVSS (SEQ ID NO: 31) |
| BG33 | QIQLQQSGPEVVKPGASVKISCKASGYTFSDYHINWVKQKPGQGLEWIGWIYPG RGNPEYNEKFKGKATLTVDRSANTAYMQLSSLTSEDSSVYFCEIYYGNYLDYW GQGTTLTVSS (SEQ ID NO: 33) |

VH: heavy chain variable region

TABLE 2

Sequences of light chain variable regions for anti-LAG-3 mAbs

| mAb clones | VL |
|---|---|
| B1 | DIQMTQTTSSLSASLGDRVTISCRASQDISNYLNWYQQKPDGTVKLLIYYTSRLH SGVPSRFSGSGSGTDYSLTISNLEPEDIATYYCHQYSNRPPTFGGGTKLEIK (SEQ ID NO: 2) |
| B2 | DVVMTQTPLSLPVSLGDQASISCRSSQSIVHSNGNTYFYWYLQKPGQSPNLLIYR VSNRFSGVPDRFSGSGSGTDFTLKISRVEAEDMGVYYCFQGTHVPYTFGGGTKL EIK (SEQ ID NO: 4) |
| B3 | DVVMTQTPLSLPVSLGDQASISCRSSQSILYSNGYTYLEWYLQKPGQSPKLLIYG VSNRFSGVPDRFSGSGSGTDFTLKISRVESEDMGVYYCFQGTHVPLTFGAGTKLE LK (SEQ ID NO: 6) |
| B4 | DVVMTQTPLSLPVSLGDQASISCRSSQSIVYSNGYTYLEWYLQKPGQSPKLLIYG VSNRFSGVPDRFSGSGSGTDFTLKISRVEAEDMGVYYCFQGTHVPLTFGAGTKL ELK (SEQ ID NO: 8) |
| B5 | DIQMTQSPSSLSASLGERVSLTCRSSQDISDYLSWLQQKPDGTIKRLIYSTSTLDS GVPKRFSGSRSGSDYSLTISSLESEDFADYYCLQYASSPPTFGGGTKLEIK (SEQ ID NO: 10) |
| B9 | DIQMTQSPSSLSASLGERVSLTCRASQDISDSLCWLQQKPDGTIKRLIYSTSTLDS GVPKRFSGSRSGSDYSLTISSLESEDFADYYCLQYASSPPTFGGGTKLEIK (SEQ ID NO: 12) |
| B6 | DIQLTQSPSSLSASLGQRVSLTCRASQDISGRLSCLQQKPDGTIKRLIYSTSTLDSG VPKRFSGSRSGSDFSLTISSLESEDFADYYCLQCVSSPPTFGGGTKLEIK (SEQ ID NO: 14) |
| B11 | DIQMTQSPSSLSASLGERVSLTCRASQDIGGSLNWLQQKPDGTIKRLIYSTSTLDS GVPKRFSGSRSGSDYSLTISSLESEDFADYYCLQNANSPPTFGGGTKLEIK (SEQ ID NO: 16) |
| B7 | DIQMTQSPSSLSASLGERVSLSCRASQDISHYLNWFQQKPDGTFKRLIYETSTLDF GVPKRFSGSRSGSDYSLTIGSLESEDFADYYCLQYATYPLTFGAGTKLELK (SEQ ID NO: 18) |

TABLE 2-continued

Sequences of light chain variable regions for anti-LAG-3 mAbs

| mAb clones | VL |
|---|---|
| B10 | DIQMTQSPSSLSASLGERVSLTCRASQDISNYLNWFQQKPDGTFKRLIYATSTLDF GVPKRFSGSRSGSDYSLTISSLESEDFADYYCLQYASYPLTFGAGTKLELK (SEQ ID NO: 20) |
| B12 | DVVMTQTPLSLPVSLGDQASISCRSSQTIVYSNGNTYLYWYLQKPGQSPKLLIYR VSNRFPGVPDRFSGSGSGTDFTLKISGVEAEDMGVYYCFQGTHVPPTFGSGTKLE MK (SEQ ID NO: 22) |
| B13 | DIVMTQSPSSLTVTAGEKVTMSCKSSQSLLNSGNQKNYLTWYQQKPGQPPKMLI YWASTRESGVPERFTGSGSGTDFTLTINSVQAEDMAIYYCQNDYGYPLAFGAGT RLELK (SEQ ID NO: 24) |
| B15 | DVVMTQTPLTLSVTIGQPASISCKSSQSLLYSNGKTYLSWLLQRPGQSPKRLIYLV SKLDSGVPDRFTGSGSGTDFTLKISRVEAEDLGVYYCVQGTHFPQTFGGGTKLEI K (SEQ ID NO: 26) |
| B16 | DIVLTQSPASLAVSLGQRATISCRASETVDDSGISFMHWYQQKPGQPPRLLIYRA SKLESGIPARFSGSGSRTDFTLTINPVETDDVATYYCQQNNKDPLTFGAGTKLEL R (SEQ ID NO: 28) |
| BG27 | DVVMTQTPLSLPVSLGDQASISCRSSQTIVHSNRYTYLEWYLQKPGQSLKLLIYG VSNRFSGVPDRFSGSGSGTDFTLKISRVEAEDMGVYYCFQGTHVPPTFGAGTKL ELK (SEQ ID NO: 30) |
| BG29 | DIVMTQAAPSVPVTPGESVSISCRSSKSLLHSDGKTYLYWFLQRPGQSPQRLIYY MSNLASGVPDRFSGRGSGTDFTLRISRVEAEDVGVYYCMQSLEYPWTFGGGTK LEIK (SEQ ID NO: 32) |
| BG33 | DIVMTQAAPSVPVTPGESVSISCRSSKSLLHSDGKTYLYWFLQRPGQSPQRLIYY MSNLASGVPDRFSGRGSGTDFTLRISRVEAEDVGVYYCMQSLEYPWTFGGGTK LEIK (SEQ ID NO: 34) |

VL: light chain variable region

TABLE 3

CDR regions 1-3 of heavy chain for anti-LAG-3 mAbs

| mAb clones | HC CDR1 (SEQ ID NO:) | CDR2 (SEQ ID NO:) | CDR3 (SEQ ID NO:) |
|---|---|---|---|
| B1 | GYSITSDYA (35) | IDYSGIT (36) | AREDHYDLAWFAY (37) |
| B2 | GYTFTDYY (38) | IFPGSGST (39) | VRIHFDYDWFFDV (40) |
| B3 | GYTFTSYD (41) | IYPENGDS (42) | ARGGYYDYVWFPY (43) |
| B4 | GYTFTSYD (44) | IYPENGDS (45) | ARGGYFDYVWFPY (46) |
| B5 | GYTFTGYY (47) | INPYNGDT (48) | VRDDGYHVRFFDV (49) |
| B9 | GYTFTGYY (50) | INPYNGDT (51) | VRDDGYHVRYFDV (52) |
| B6 | GYTLSNYY (53) | INPYNGDT (54) | ARDDGYHVYYFDY (55) |
| B11 | GYTFTNYY (56) | INPYNGDI (57) | ARDDGYYVYYFDC (58) |
| B7 | GYSFSDYN (59) | INLDSAAT (60) | ASYDY (61) |
| B10 | GYSFTDYN (62) | ITLDYGTT (63) | ACYDY (64) |
| B12 | GFDFSRYW (65) | INPDSSTI (66) | ARITSGYYFDY (67) |
| B13 | GFTFSIYA (68) | ISSGGSNT (69) | ARGDVYYDYDGRGFDY (70) |
| B15 | GFNIKDDY (71) | IDPENGDT (72) | TLYAY (73) |
| B16 | GYTFTDYY (74) | INPYNGRT (75) | ASPEGY (76) |
| BG27 | GYTFTSYD (77) | IYPGNGDA (78) | ARGDYGNYVWFAY (79) |

TABLE 3-continued

CDR regions 1-3 of heavy chain for anti-LAG-3 mAbs

| mAb clones | CDR1 (SEQ ID NO:) | CDR2 (SEQ ID NO:) | CDR3 (SEQ ID NO:) |
|---|---|---|---|
| BG29 | GYTFSDYH (80) | IYPGRGDP (81) | EIYYGNYIDY (82) |
| BG33 | GYTFSDYH (83) | IYPGRGNP (84) | EIYYGNYLDY (85) |

HC: heavy chain; CDR: complementarity determining region
The HC CDRs for the anti-LAG-3 mAbs were determined utilizing the IMGT method (Lefranc, M.-P. et al., Nucleic Acids Res. 1999; 27:209-212).

TABLE 4

CDR regions 1-3 of light chain for anti-LAG-3 mAbs

| mAb clones | CDR1 (SEQ ID NO:) | CDR2 (SEQ ID NO:) | CDR3 (SEQ ID NO:) |
|---|---|---|---|
| B1 | QDISNY (86) | YTS (87) | HQYSNRPPT (88) |
| B2 | QSIVHSNGNTY (89) | RVS (90) | FQGTHVPYT (91) |
| B3 | QSILYSNGYTY (92) | GVS (93) | FQGTHVPLT (94) |
| B4 | QSIVYSNGYTY (95) | GVS (96) | FQGTHVPLT (97) |
| B5 | QDISDY (98) | STS (99) | LQYASSPPT (100) |
| B9 | QDISDS (101) | STS (102) | LQYASSPPT (103) |
| B6 | QDISGR (104) | STS (105) | LQCVSSPPT (106) |
| B11 | QDIGGS (107) | STS (108) | LQNANSPPT (109) |
| B7 | QDISHY (110) | ETS (111) | LQYATYPLT (112) |
| B10 | QDISNY (113) | ATS (114) | LQYASYPLT (115) |
| B12 | QTIVYSNGNTY (116) | RVS (117) | FQGTHVPFT (118) |
| B13 | QSLLNSGNQKNY (119) | WAS (120) | QNDYGYPLA (121) |
| B15 | QSLLYSNGKTY (122) | LVS (123) | VQGTHFPQT (124) |
| B16 | ETVDDSGISF (125) | RAS (126) | QQNNKDPLT (127) |
| BG27 | QTIVHSNRYTY (128) | GVS (129) | FQGTHVPPT (130) |
| BG29 | KSLLHSDGKTY (131) | YMS (132) | MQSLEYPWT (133) |
| BG33 | KSLLHSDGKTY (134) | YMS (135) | MQSLEYPWT (136) |

LC: light chain; CDR: complementarity determining region
The LC CDRs for the anti-LAG-3 mAbs were determined utilizing the IMGT method (Lefranc, M.-P. et al., Nucleic Acids Res. 1999; 27:209-212).

Example 2: Production and Purification of mAbs from Hybridoma Supernatants and Culture Media from Transfected HEK293 Cells Mouse anti-LAG-3 mAbs were purified from hybridoma media/supernatants using Protein A affinity chromatography. To obtain the recombinant anti-LAG-3 chimeric mAbs, the expression vectors containing the mouse variable regions (VH and VL) fused to the constant regions of human IgG1 heavy chain and kappa light chain, respectively, were transiently transfected into HEK293 cells. The recombinant antibodies produced in the suspension of the HEK293 cells were purified using Protein A affinity chromatography. For production of certain mAbs, the expression vectors containing the mouse variable regions (VH and VL) fused to the constant regions of human IgG4 heavy chain and kappa light chain, respectively, or the expression vectors for humanized mAbs were transiently transfected into 293E cells and the mAbs were purified using Protein A affinity chromatography.

Example 3: FACS Binding Analysis of Purified Antibodies

Figure 1B:
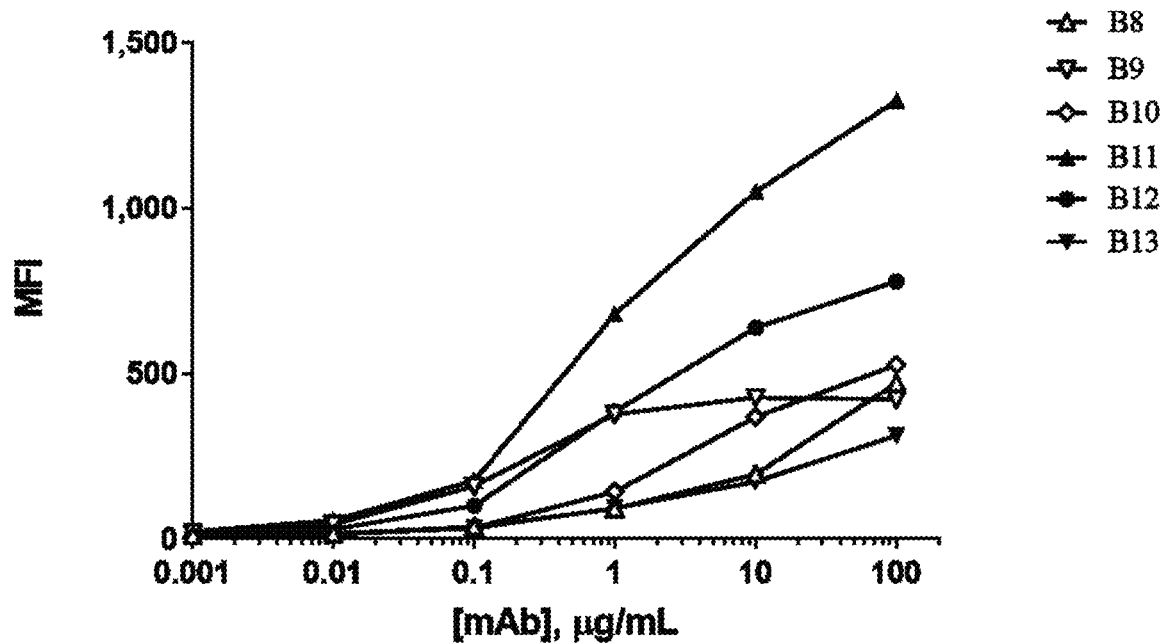
Figure 2:
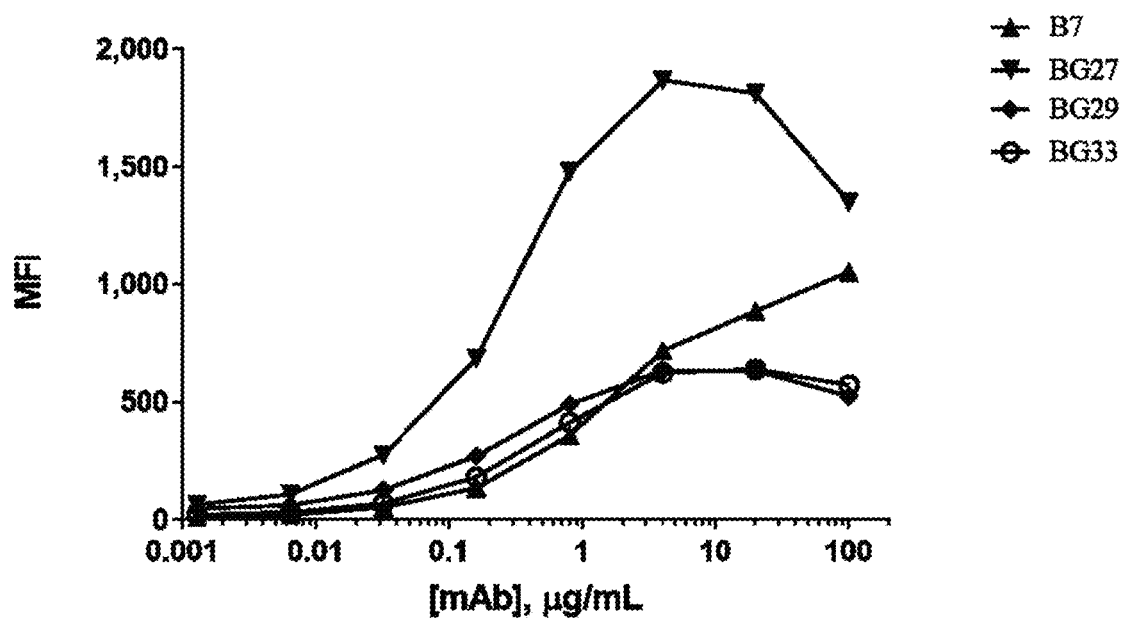
FIG. 2 shows the binding of purified mouse anti-LAG-3 mAbs (BG27, BG29, and BG33) to CHO-S cells stably transfected with full-length human LAG-3 by FACS analysis (B7 was used as a control).
Figure 3A:
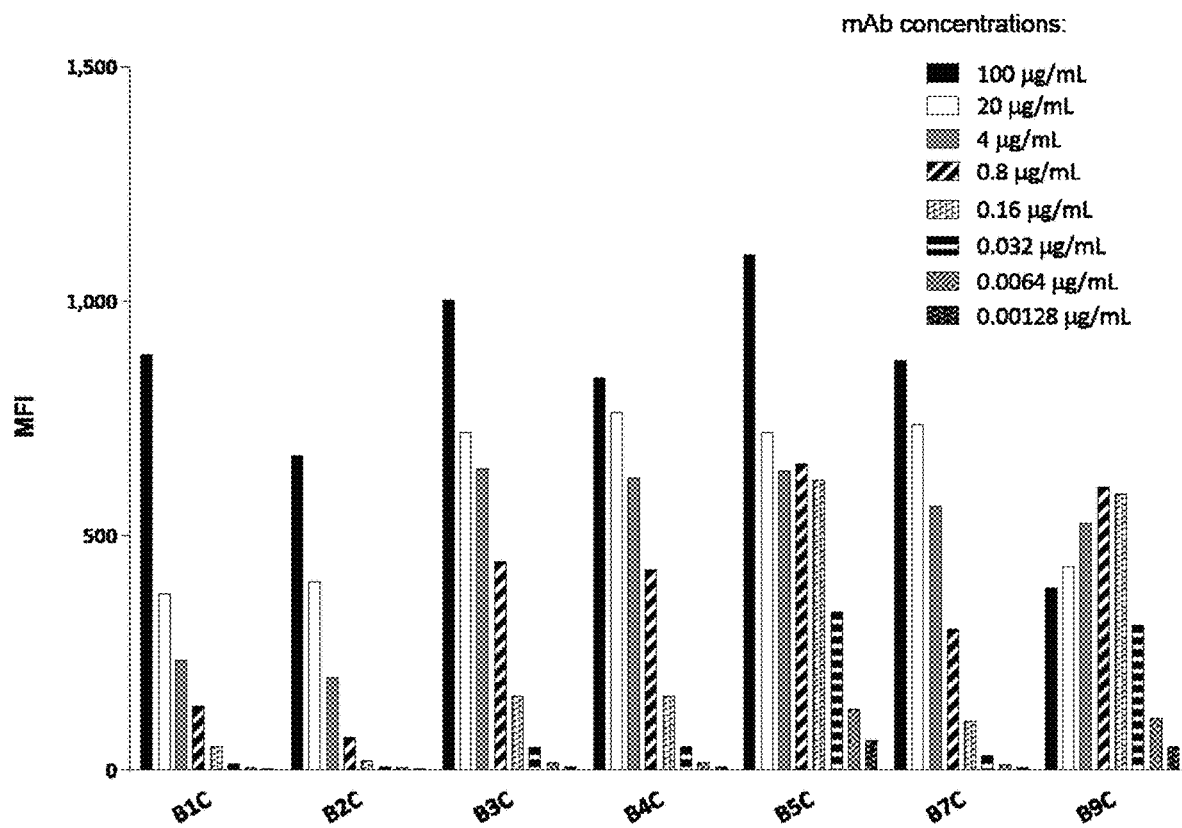
FIGS. 3A-3B show the binding of anti-LAG-3 chimeric mAbs (VH and VL regions of mouse mAbs fused to the constant regions of human IgG1 heavy chain and kappa light chain, respectively) to CHO-S cells stably transfected with full-length human LAG-3 by FACS analysis. The mAbs and controls were tested in the same experiment and shown in two separate figures (FIGS. 3A and 3B) for clarity. B1C, the chimeric version of mouse mAb B1; B2C, the chimeric version of mouse mAb B2; B3C, the chimeric version of mouse mAb B3; B4C, the chimeric version of mouse mAb B4; B5C, the chimeric version of mouse mAb B5; B7C, the chimeric version of mouse mAb B7; B9C, the chimeric version of mouse mAb B9; B10C, the chimeric version of mouse mAb B10; B11C, the chimeric version of mouse mAb B11. Neg, not treated with primary mAbs, PI (propidium iodide) or PE-conjugated anti-human IgG; PI, treated with PI but not with primary mAbs or PE-conjugated anti-human IgG; "Anti-Hu" and "Anti-Mu" groups were not treated with primary antibodies, but were treated with PE-conjugated anti-human IgG and anti-mouse IgG secondary Abs, respectively.
Figure 3B:
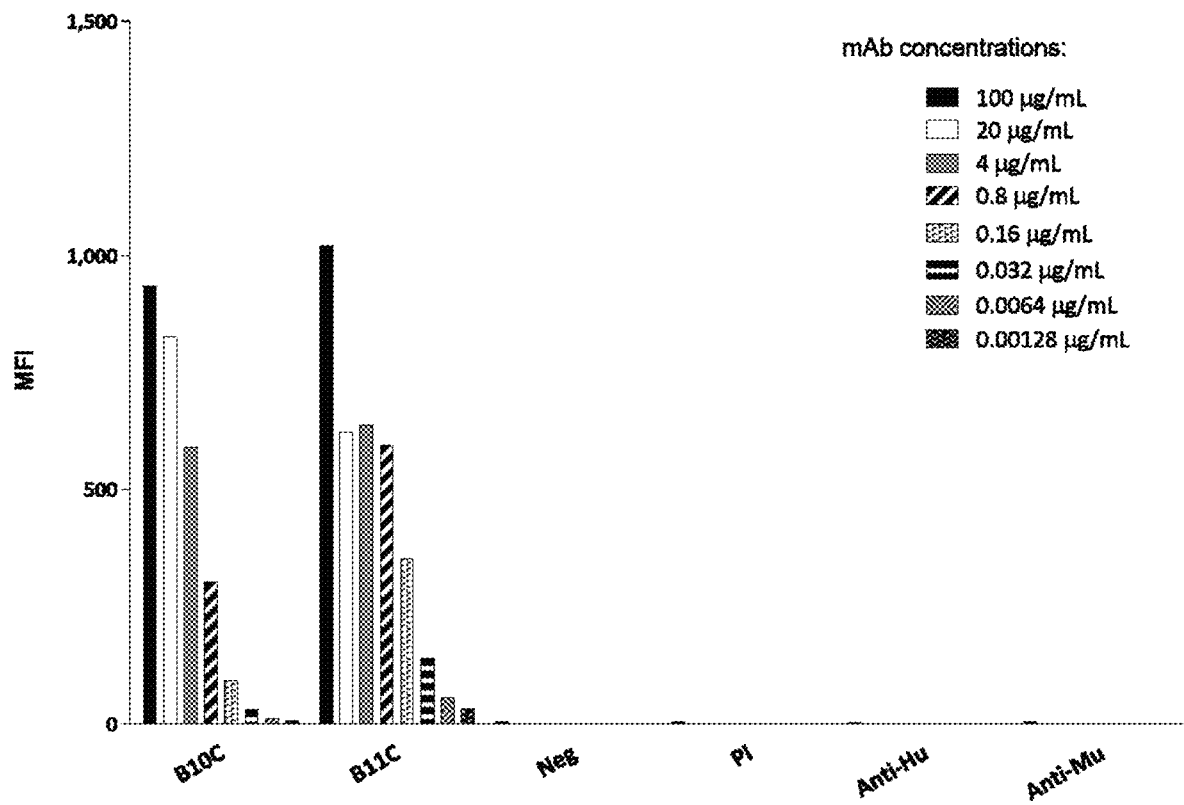

CHO-S cells stably transfected with full-length human LAG-3 were transferred to a 96-well plate. Around 200,000 cells were incubated with either purified chimeric anti-LAG-3 mAbs (variable regions of mouse mAbs fused to the constant regions of human IgG1 heavy chain and kappa light chain, respectively) or purified mouse anti-LAG-3 mAbs from hybridoma supernatants at various concentrations for 15 minutes at 4° C. Cells were then centrifuged at 1,000 rpm for 5 minutes and washed with FACS buffer (PBS supplemented with 5% BSA) three times. For the cells treated with the chimeric antibodies, the cells were then incubated with PE-conjugated goat anti-human IgG polyclonal antibodies and incubated on ice for another 15 minutes; for the cells treated with mouse mAbs, the cells were incubated with PE-conjugated goat anti-mouse IgG polyclonal antibodies and incubated on ice for another 15 minutes. Cells were then washed with FACS buffer three times and then resuspended in FACS buffer containing 0.1 µg/ml PI (propidium iodide) for live/dead cell gating. Cells were then run through the FACS Caliber instrument and the data were analyzed by the FLOWJO™ software. Results of the FACS binding analysis of the mouse anti-LAG-3 mAbs (B1, B2, B3, B4, B5, B6, B7, B8, B9, B10, B11, B12, and B13) are provided in FIGS. 1A-1B. Results of the FACS binding analysis of the mouse anti-LAG-3 mAbs (BG27, BG29, and BG33) are provided in FIG. 2. Results of the FACS binding analysis of the chimeric anti-LAG-3 mAbs are provided in FIGS. 3A-3B.

Example 4: Affinity Analysis of Anti-LAG-3 mAbs Using Biacore

Anti-mouse IgG antibodies were immobilized via amine coupling on CM5 chip surface. Anti-LAG-3 mAbs in hybridoma supernatants were captured on the chip surface and a series of concentrations (50-400 nM) of human LAG-3(ECD)-huFc protein were injected and passed through the captured surface. The on and off rates for antibody-antigen binding were measured, curve fitted and calculated. The KD values of select anti-LAG-3 mAbs are shown in Table 5.

TABLE 5

KD values for anti-LAG-3 mAbs from a BIACORE® assay.

| mAb clones | KD (nM) Human LAG-3 |
|---|---|
| B1 | 1.21 |
| B2 | 4.09 |
| B3 | 1.53 |
| B4 | 0.217 |
| B5 | 1.34 |
| B9 | 1.53 |
| B11 | 1.18 |
| B7 | 0.758 |
| B10 | 1.1 |
| B13 | 8.17 |

Figure 4A:
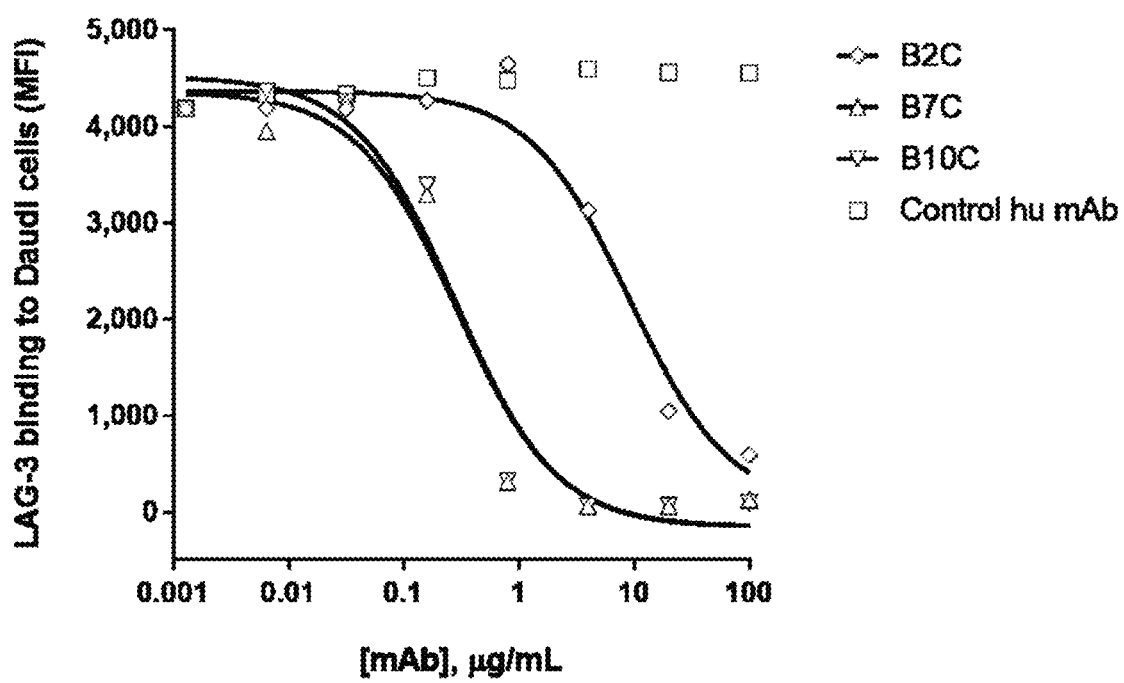
FIGS. 4A-4D show inhibition of human LAG-3 binding to MHC class II molecules by select anti-LAG-3 mAbs. An in vitro binding assay was performed using recombinant LAG-3(ECD)-mFc and Daudi cells which express human MHC class II molecules. LAG-3 did not bind to a different cell line that does not express MHC class II molecules in a separate experiment. The binding of LAG-3(ECD)-mFc to Daudi cells in the presence of anti-LAG-3 mAbs or a control mAb was analyzed by FACS.
Figure 4B:
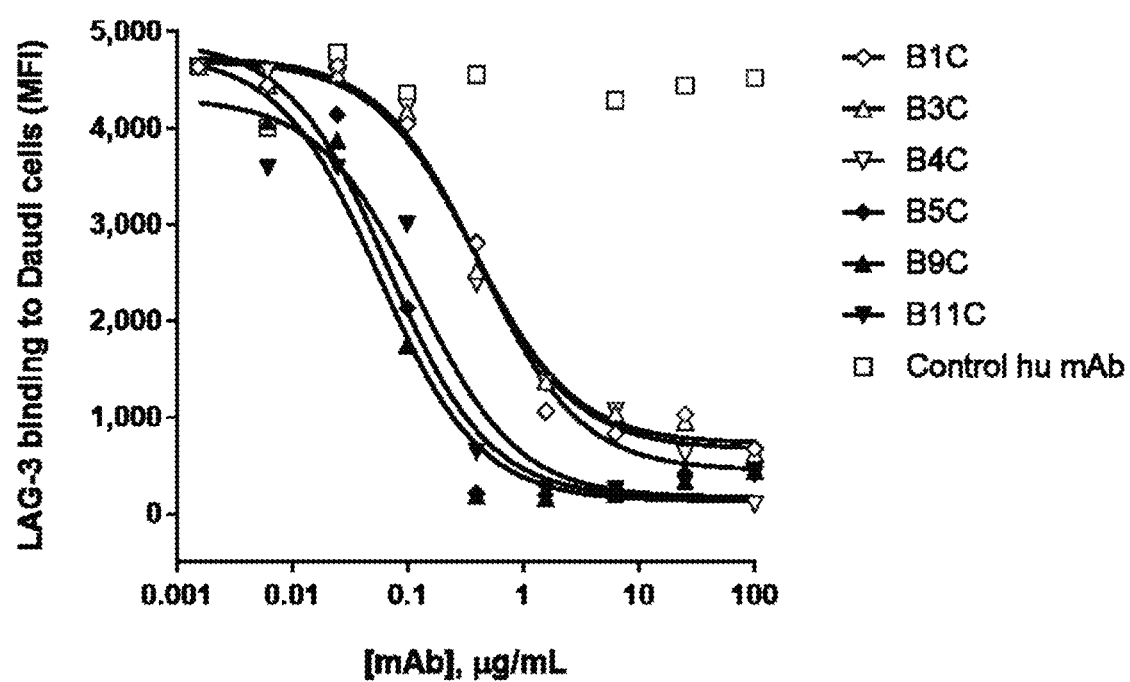
Figure 4C:
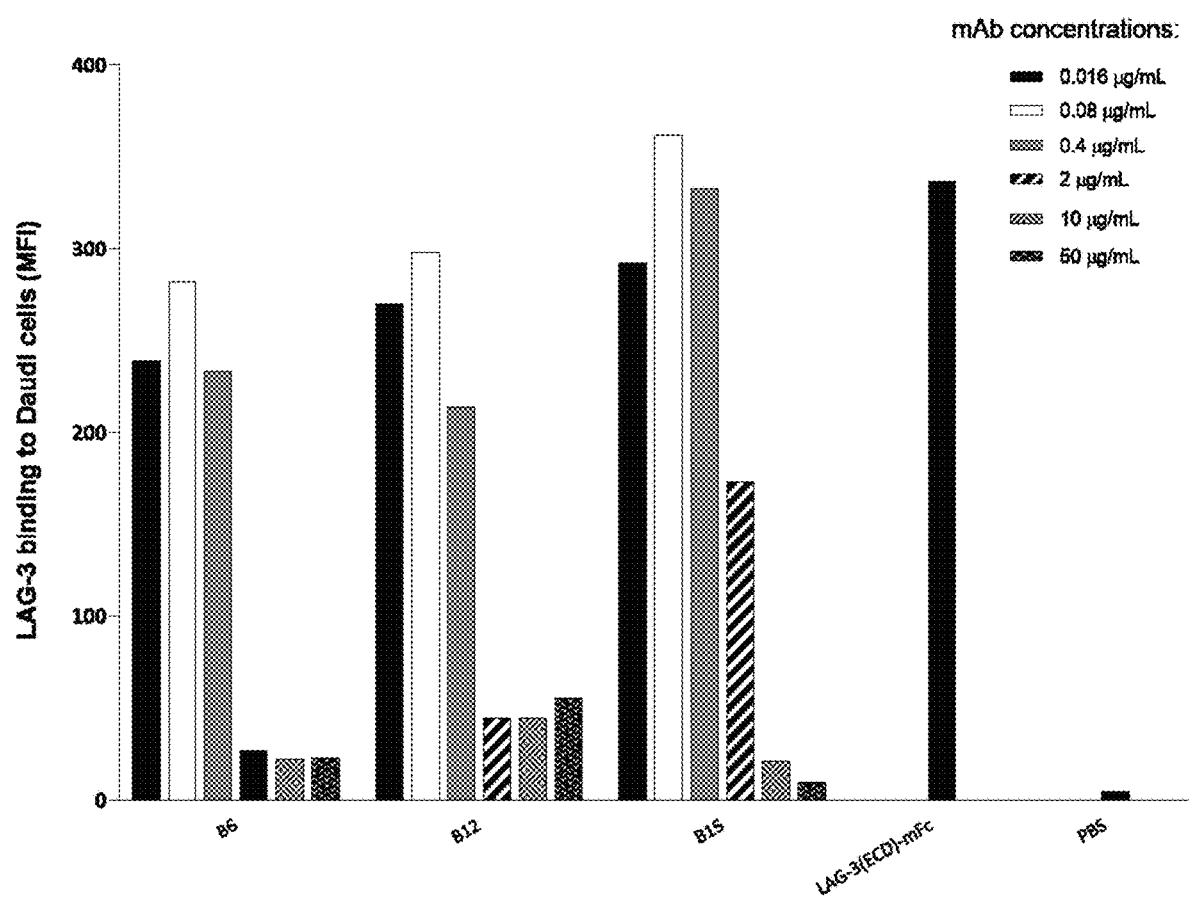
Figure 4D:
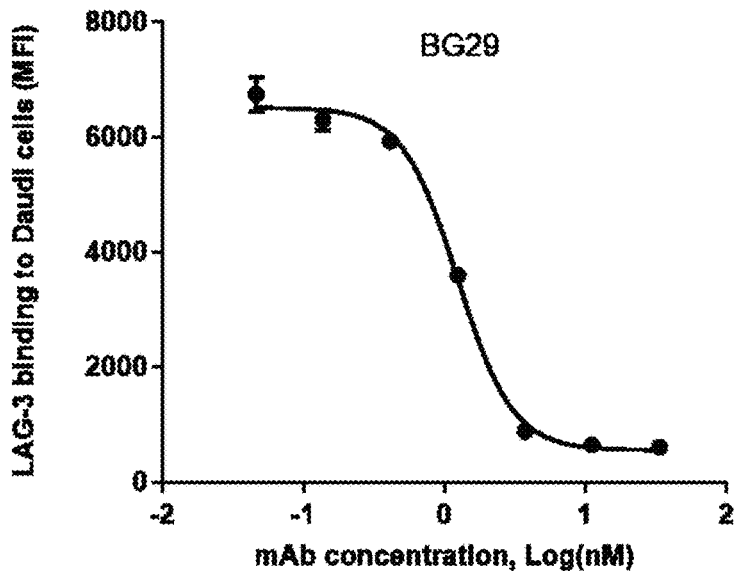

Example 5: Cell-Based Assay to Evaluate the Blocking Effect of Anti-LAG-3 mAbs on LAG-3/MHC Class II Binding Human Daudi cells were cultured in RPMI+10% FBS. Human LAG-3(ECD)-mFc protein (human LAG-3 ECD fused to mouse Fc) at 1 µg/ml final concentration was incubated with purified mouse, humanized, or chimeric anti-LAG-3 mAbs at various concentrations for 15 minutes at 4° C. The mixture was then added to 100,000 human Daudi cells in a 96-well round bottom plate, mixed and incubated for 15 minutes on ice. Cells were then centrifuged at 1,000 rpm for 5 minutes and washed with FACS buffer (PBS supplemented with 5% BSA) three times. The cells were then incubated with PE-conjugated goat anti-mouse Fc polyclonal antibodies on ice for 15 minutes, washed with FACS buffer three times and then resuspended in FACS buffer containing 0.1 µg/ml PI (propidine iodine) for live/dead cell gating. Cells were then run through the FACS Caliber instrument and the data were analyzed by the FLOWJO™ software. Results of the inhibition of LAG-3 binding to Daudi cells by chimeric mAbs B2C, B7C, and B10C are shown in FIG. 4A. Results of the inhibition of LAG-3 binding to Daudi cells by chimeric mAbs B1C, B3C, B4C, B5C, B9C, and B11C are shown in FIG. 4B. Results of the inhibition of LAG-3 binding to Daudi cells by mouse mAbs B6, B12, and B15 are shown in FIG. 4C. Results of the inhibition of LAG-3 binding to Daudi cells by chimeric BG29 is shown in FIG. 4D.

Example 6: Epitope Mapping for Anti-LAG-3 mAbs

The binding regions within human LAG-3 (hLAG3) by anti-LAG-3 mAbs were mapped using an ELISA-based peptide competition assay. The extracellular domain (ECD) of LAG-3 is composed of four immunoglobulin (Ig)-like domains (D1-D4) (Huard et al., Proc Natl Acad Sci USA. 94:5744-9 (1997)). The first Ig-like domain (D1) contains an exposed extra loop region that contains the following 30-amino acid sequence: GPPAAAPGHPLAPGPH-PAAPSSWGPRPRRY (peptide 1-30 in Table 6; SEQ ID NO:153). Anti-LAG-3 mAbs were examined to determine if each mAb was capable of binding to this region and/or adjacent sequences. Additionally, the epitope for binding by each mAb was mapped. Competition peptides based on the sequence of this region were designed for epitope mapping (Tables 6, 7, 8, 9, and 10). In addition, the amino acid sequence immediately upstream of this region was also included in the peptide design (Table 6).

TABLE 6

Peptides used in the competition assay with B5 and B6

| Peptide | Sequence | SEQ ID NO: |
|---|---|---|
| 1-30 | GPPAAAPGHPLAPGPHPAAPSSWGPRPRRY | 153 |
| 3-14 | PAAAPGHPLAPG | 154 |
| 2-14 | PPAAAPGHPLAPG | 155 |
| 1-14 | GPPAAAPGHPLAPG | 156 |
| 1-13 | GPPAAAPGHPLAP | 157 |
| 1-12 | GPPAAAPGHPLA | 158 |
| 1-11 | GPPAAAPGHPL | 159 |
| 2-12 | PPAAAPGHPLA | 160 |
| 31W | WQHQPDSGPPAAAPGHPLAPGPHPAAPSSWG | 161 |
| S14 | SGPPAAAPGHPLAP | 162 |
| D15 | DSGPPAAAPGHPLAP | 163 |
| P16 | PDSGPPAAAPGHPLAP | 164 |
| Q17 | QPDSGPPAAAPGHPLAP | 165 |
| Q16 | QPDSGPPAAAPGHPLA | 166 |

TABLE 6-continued

Peptides used in the competition assay with B5 and B6

| Peptide | Sequence | SEQ ID NO: |
|---|---|---|
| Q15 | QPDSGPPAAAPGHPL | 167 |
| Q14 | QPDSGPPAAAPGHP | 168 |

TABLE 7

Peptides used in the competition assay with B7

| Peptide | Sequence | SEQ ID NO: |
|---|---|---|
| 1-30 | GPPAAAPGHPLAPGPHPAAPSSWGPRPRRY | 153 |
| 15-30 | PHPAAPSSWGPRPRRY | 169 |
| 15-29 | PHPAAPSSWGPRPRR | 170 |
| 15-28 | PHPAAPSSWGPRPR | 171 |
| 15-27 | PHPAAPSSWGPRP | 172 |
| 15-26 | PHPAAPSSWGPR | 173 |
| 16-30 | HPAAPSSWGPRPRRY | 174 |
| 17-30 | PAAPSSWGPRPRRY | 175 |
| 18-30 | AAPSSWGPRPRRY | 176 |
| 19-30 | APSSWGPRPRRY | 177 |
| 20-30 | PSSWGPRPRRY | 178 |
| 21-30 | SSWGPRPRRY | 179 |

TABLE 8

Peptides used in the competition assay with B12

| Peptide | Sequence | SEQ ID NO: |
|---|---|---|
| 1-14 | GPPAAAPGHPLAPG | 156 |
| 2-14 | PPAAAPGHPLAPG | 155 |
| 3-14 | PAAAPGHPLAPG | 154 |
| 4-14 | AAAPGHPLAPG | 180 |
| 5-14 | AAPGHPLAPG | 181 |
| 6-14 | APGHPLAPG | 182 |
| 1-19 | GPPAAAPGHPLAPGPHPAA | 183 |
| S14 | SGPPAAAPGHPLAP | 162 |
| D15 | DSGPPAAAPGHPLAP | 163 |
| P16 | PDSGPPAAAPGHPLAP | 164 |
| Q17 | QPDSGPPAAAPGHPLAP | 165 |
| Q16 | QPDSGPPAAAPGHPLA | 166 |
| Q15 | QPDSGPPAAAPGHPL | 167 |
| Q14 | QPDSGPPAAAPGHP | 168 |

TABLE 9

Peptides used in the competition assay with BG29

| Peptide | Sequence | SEQ ID NO: |
|---|---|---|
| 1-30 | GPPAAAPGHPLAPGPHPAAPSSWGPRPRRY | 153 |
| 1-12 | GPPAAAPGHPLA | 158 |
| 1-13 | GPPAAAPGHPLAP | 157 |
| 1-14 | GPPAAAPGHPLAPG | 156 |
| 2-14 | PPAAAPGHPLAPG | 155 |
| 3-14 | PAAAPGHPLAPG | 154 |
| 4-14 | AAAPGHPLAPG | 180 |
| 5-14 | AAPGHPLAPG | 181 |
| 6-14 | APGHPLAPG | 182 |
| 7-14 | PGHPLAPG | 184 |
| 6-13 | APGHPLAP | 185 |

TABLE 10

Peptides used in the competition assay with B3 and B4

| Peptide | Sequence | SEQ ID NO: |
|---|---|---|
| 16-30 | HPAAPSSWGPRPRRY | 174 |
| 15-30 | PHPAAPSSWGPRPRRY | 169 |
| 14-24 | GPHPAAPSSWG | 186 |
| 13-24 | PGPHPAAPSSWG | 187 |
| 12-24 | APGPHPAAPSSWG | 188 |
| 11-24 | LAPGPHPAAPSSWG | 189 |
| 7-22 | PGHPLAPGPHPAAPSS | 190 |
| 7-23 | PGHPLAPGPHPAAPSSW | 191 |

Anti-human IgG in carbonate coating buffer was coated on an ELISA plate at 4° C. (50 μL/well at 1 μg/mL) overnight. In each well of a separate plate, a chimeric version of a given anti-LAG-3 mAb (50 μL/well at 1.4 nM) and a competition peptide (50 μL/well at various concentrations as indicated in the figures) were mixed and incubated for 30 minutes at room temperature. Then human LAG-3 extracellular domain (ECD) fused to mouse Fc (hLAG3-mFc) was added to each well (50 μL/well at 2 nM) and the final mixture was incubated at room temperature for 60 minutes before added to the ELISA plate (50 μL/well) for another 60-minute incubation. The final incubation after adding the mixture to the ELISA plate was also performed at 4° C. overnight in some assays. The plate was washed and the binding of hLAG3-mFc to the immobilized anti-LAG-3 mAb was detected by adding anti-mouse IgG conjugated to horseradish peroxidase (hIgG-HRP) (ThermoFisher Scientific, Cat #: A16084; Waltham, Mass.) and incubating for 60 minutes. Then after washing, the ELISA was developed using One-step Detection Solution (ThermoFisher Scientific, Cat #: 34028) and measured as the absorbance at 450 nm. An inhibition signal reflects the ability of the competition peptide to bind to the mAb in solution and inhibit the binding of hLAG3-mFc to the mAb in solution.

Figure 5A:
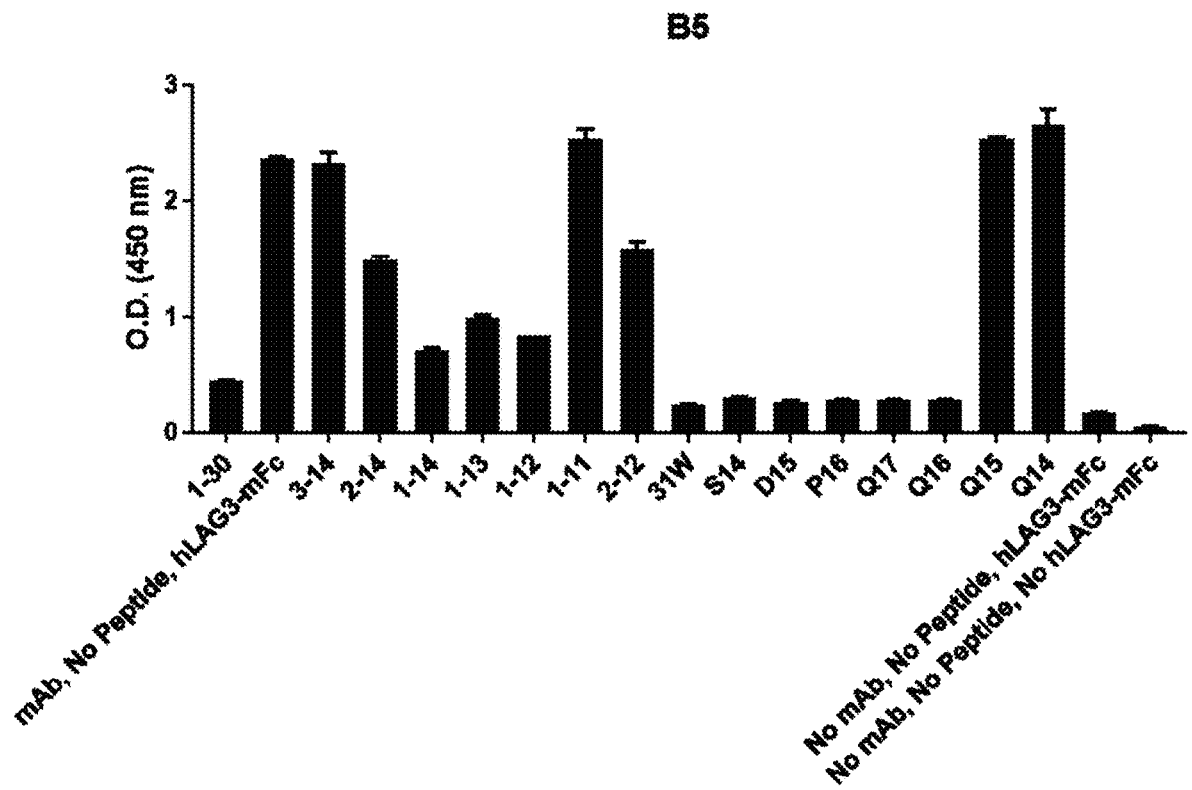
FIGS. 5A-5D show the effect of competition peptides on LAG-3 binding to anti-LAG-3 mAbs.
Figure 5B:
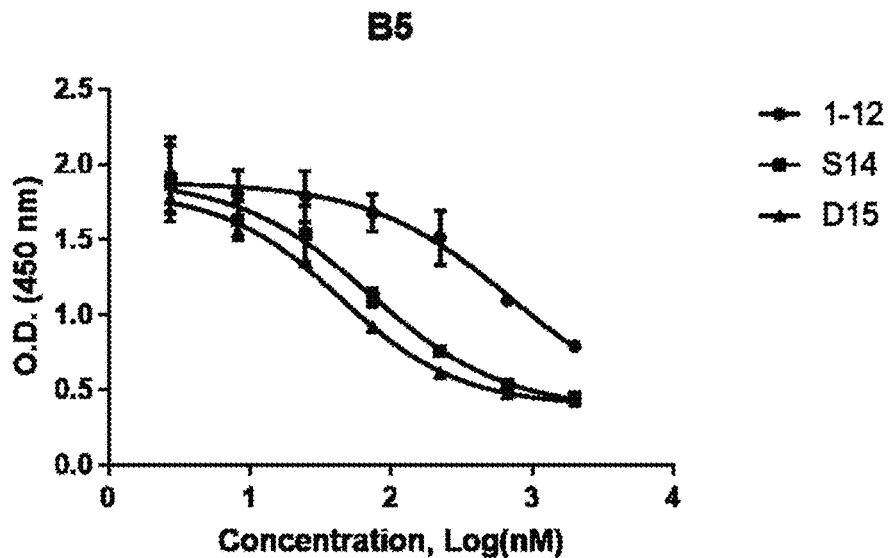
Figure 5C:
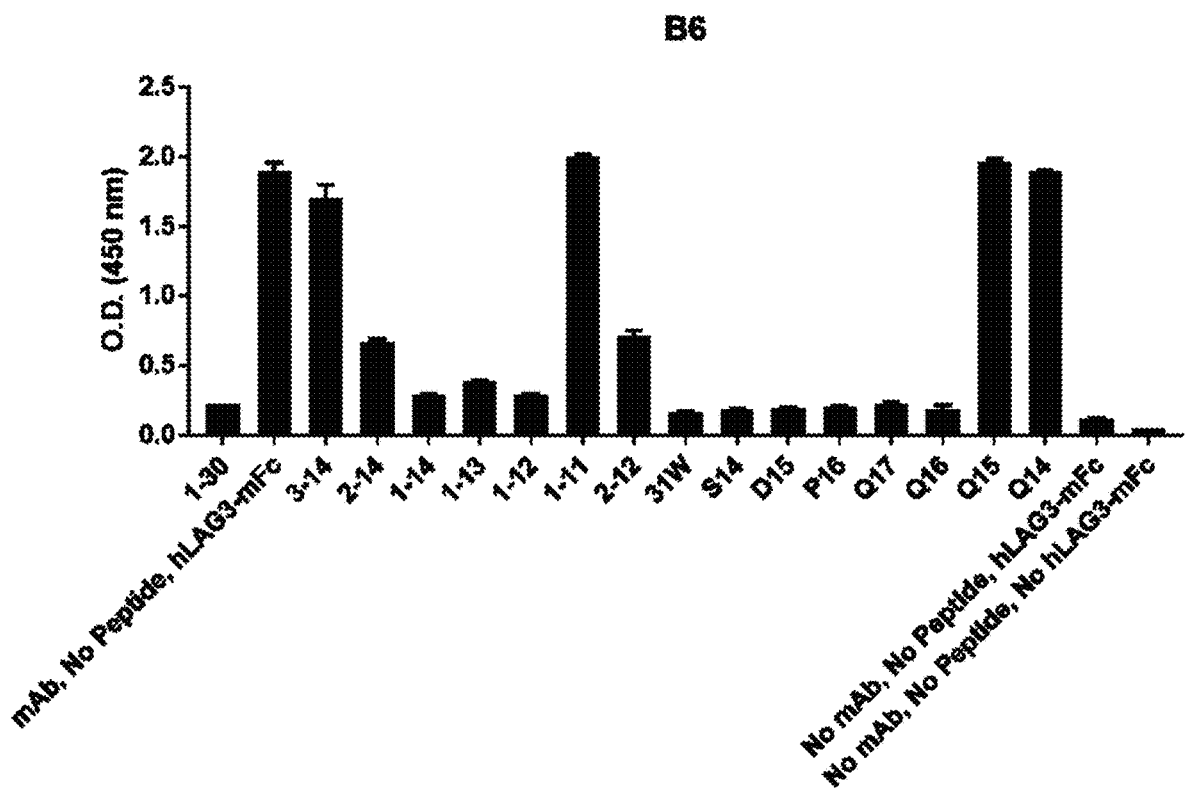
Figure 5D:
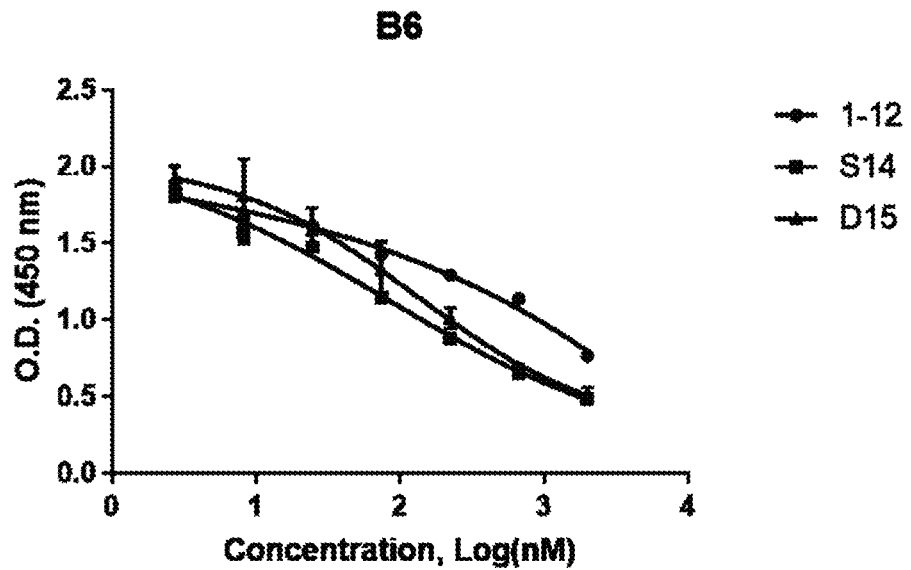
Figure 6:
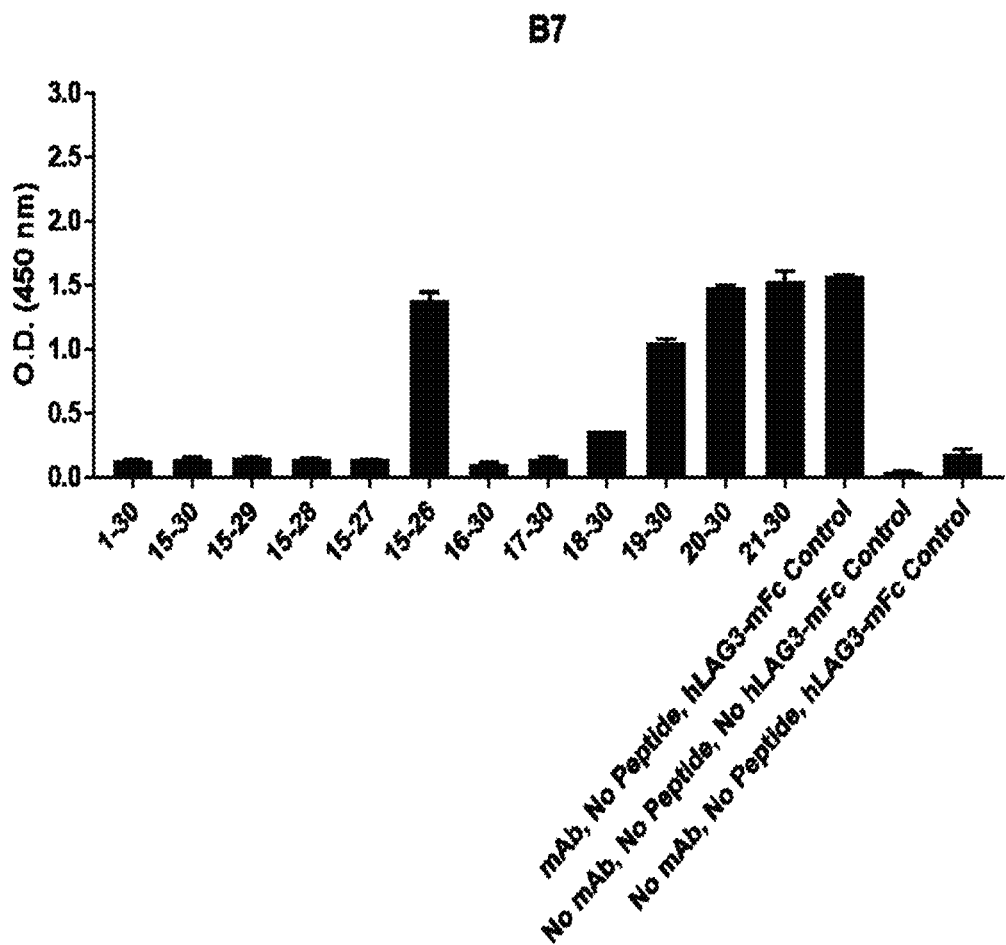
FIG. 6 shows the effect of competition peptides on human LAG-3 binding to anti-LAG-3 mAb B7 (human IgG4 heavy chain and kappa light chain chimeric; B7/IgG4) measured by ELISA as described in FIG. 5A. The assay condition is the same as in FIG. 5A except that the final incubation of the mAb, the competition peptide, and hLAG3-mFc on the ELISA plate was performed at room temperature for 60 minutes instead of incubation at 4° C. overnight.
Figure 7:
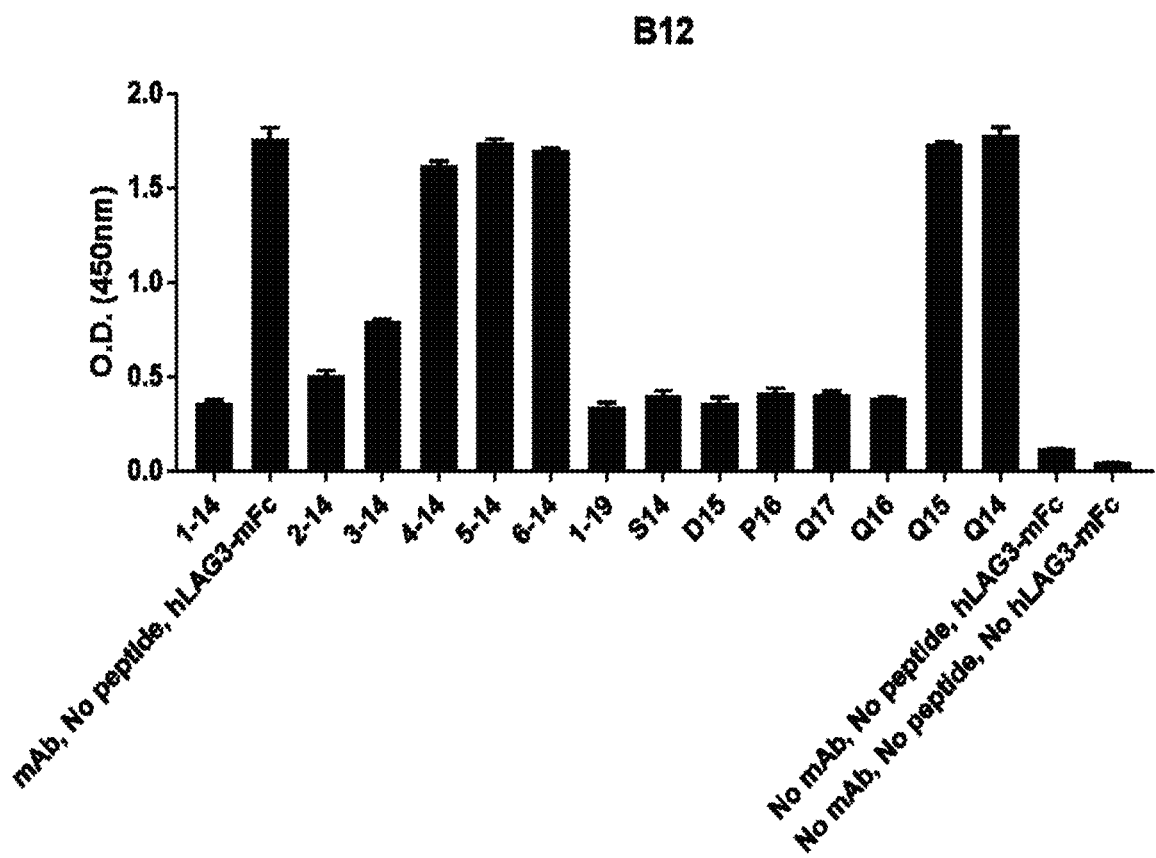
FIG. 7 shows the effect of competition peptides on human LAG-3 binding to anti-LAG-3 mAb B12 (human IgG1 heavy chain and kappa light chain chimeric) measured by ELISA as described in FIG. 5A.
Figure 8:
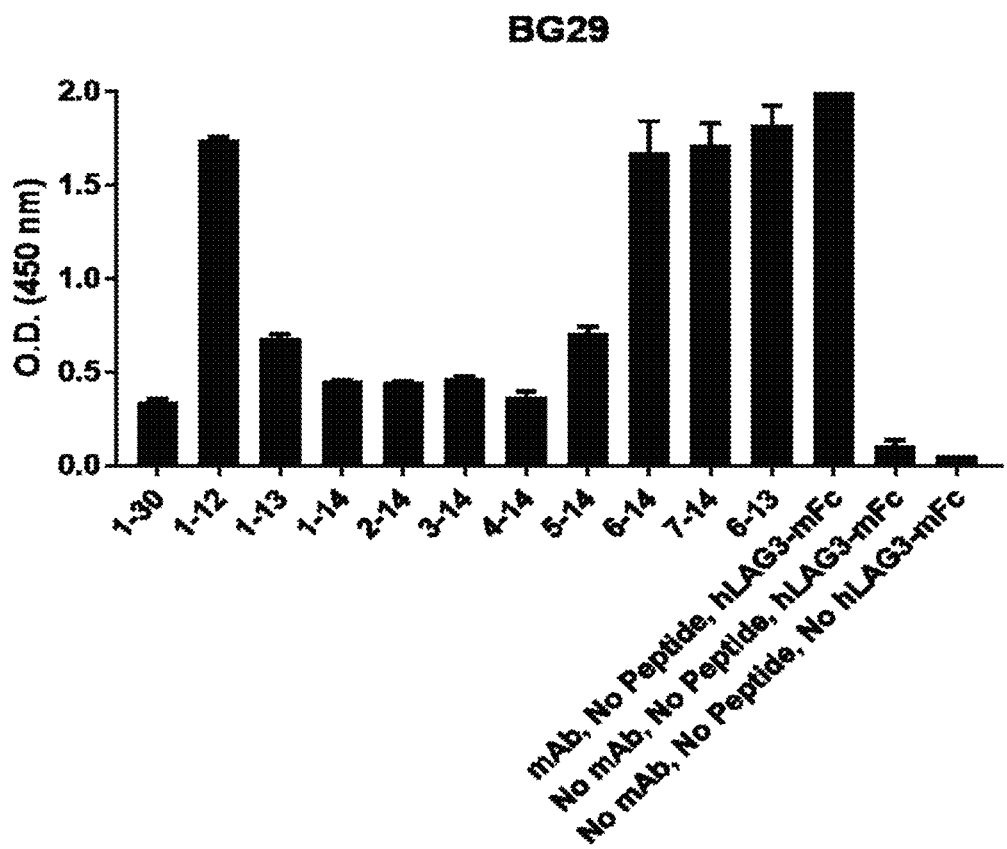
FIG. 8 shows the effect of competition peptides on human LAG-3 binding to anti-LAG-3 mAb BG29 (human IgG4 heavy chain and kappa light chain chimeric) measured by ELISA as described in FIG. 5A except that the final peptide concentration in the incubation was 200-fold that of hLAG3-mFc.
Figure 9A:
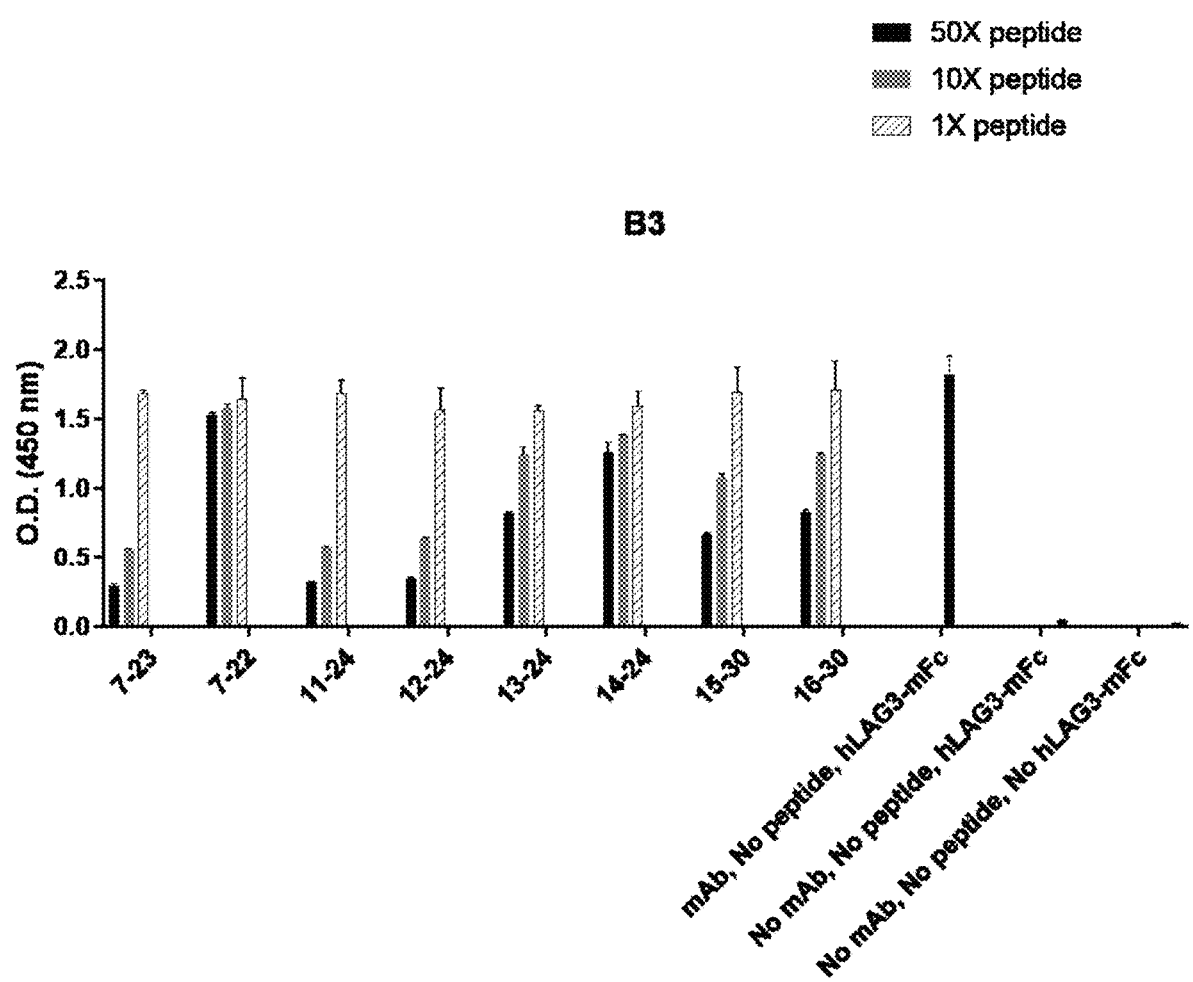
FIGS. 9A-9B show the effect of competition peptides on LAG-3 binding to anti-LAG-3 mAbs.
Figure 9B:
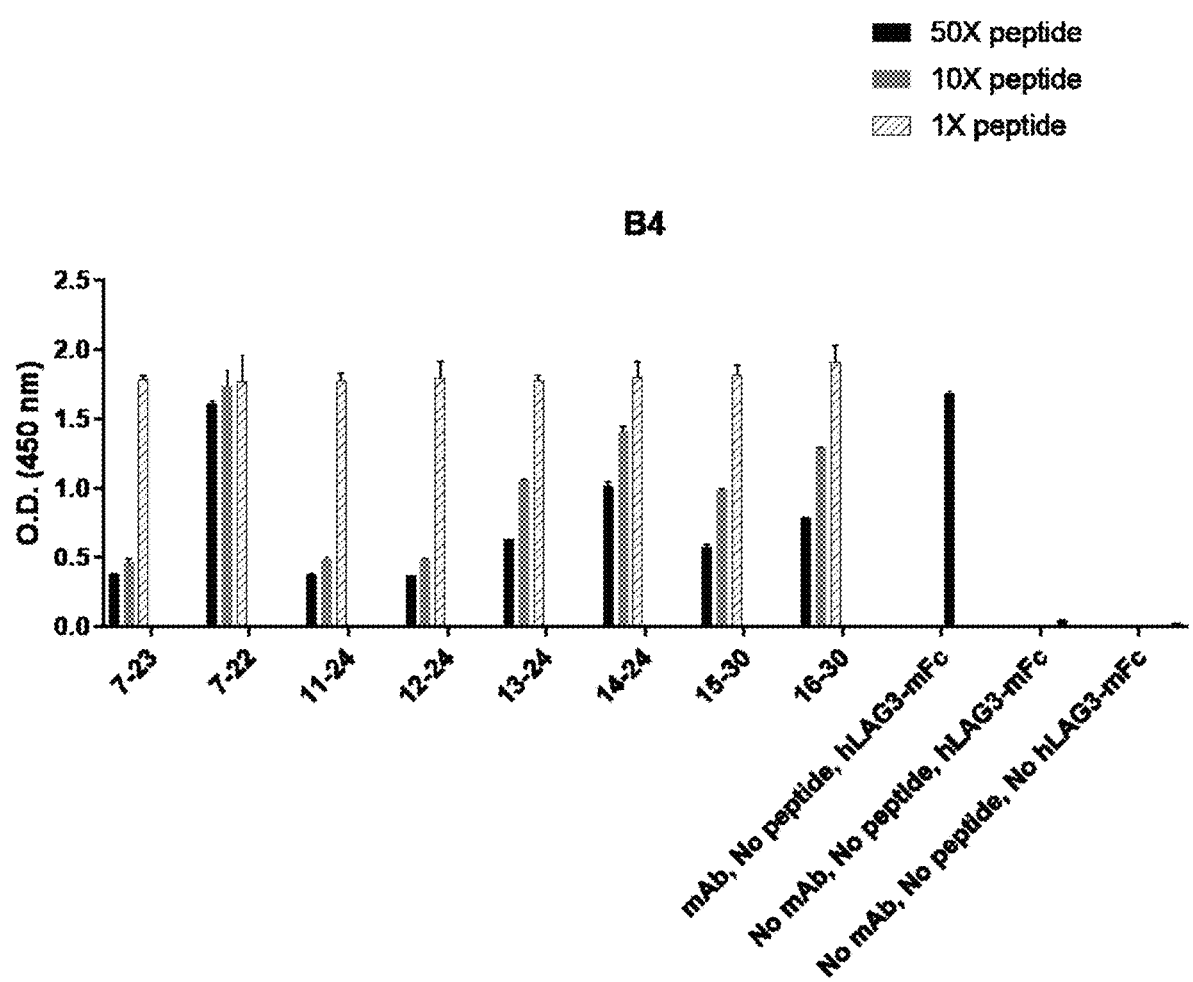

Inhibition of hLAG3-mFc binding to B5 by the competition peptides is shown in FIGS. 5A and 5B; inhibition of hLAG3-mFc binding to B6 by the competition peptides is shown in FIGS. 5C and 5D; inhibition of hLAG3-mFc binding to B7 by the competition peptides is shown in FIG. 6; inhibition of hLAG3-mFc binding to B12 by the competition peptides is shown in FIG. 7; inhibition of hLAG3-mFc binding to BG29 by the competition peptides is shown in FIG. 8; inhibition of hLAG3-mFc binding to B3 and B4 by the competition peptides is shown in FIGS. 9A and 9B.

Based on the peptide competition assay in FIG. 5, it was determined that B5 binds to the sequence SGPPAAAPGH-PLA (SEQ ID:192) and, therefore, this sequence is the epitope of B5. Based on the data in FIGS. 5C and 5D, it was determined that SGPPAAAPGHPLA (SEQ ID NO:192) is also the epitope of B6. The mapping data in FIG. 6 indicated that the epitope for B7 is PAAPSSWGPRP (SEQ ID:193). The mapping data in FIG. 7 indicated that the epitope for B12 is GPPAAAPGHPLA (SEQ ID:158). The mapping data in FIG. 8 indicated that the epitope for BG29 is AAAPGH-PLAPG (SEQ ID NO:180). The mapping data in FIGS. 9A and 9B indicated that the epitope for B3 and B4 is APGPH-PAAPSSW (SEQ ID NO:194).

Example 7: Humanization of Anti-LAG-3 mAbs

Figure 10A:
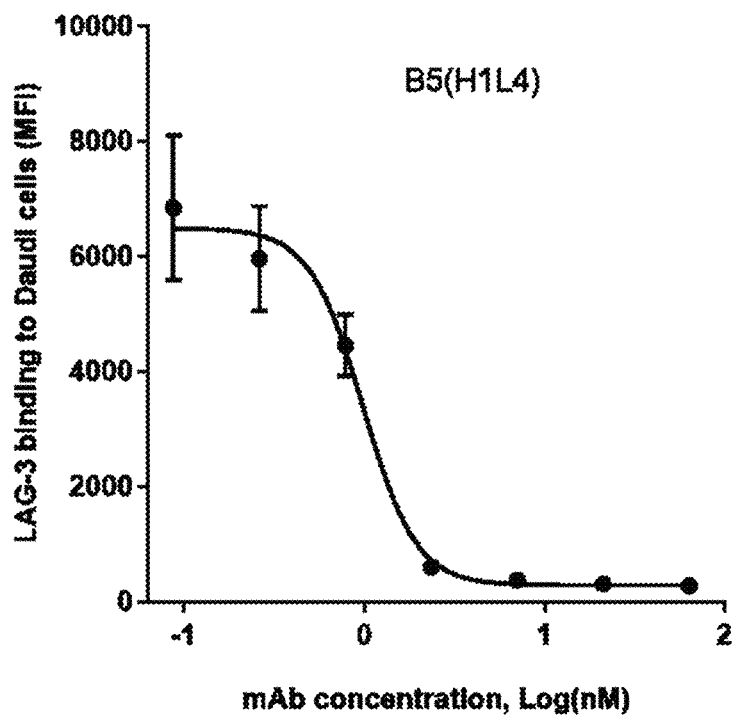
FIGS. 10A-10C show the inhibition of binding of LAG-3 to WIC class II molecules on cells by anti-LAG3 mAbs.
Figure 10B:
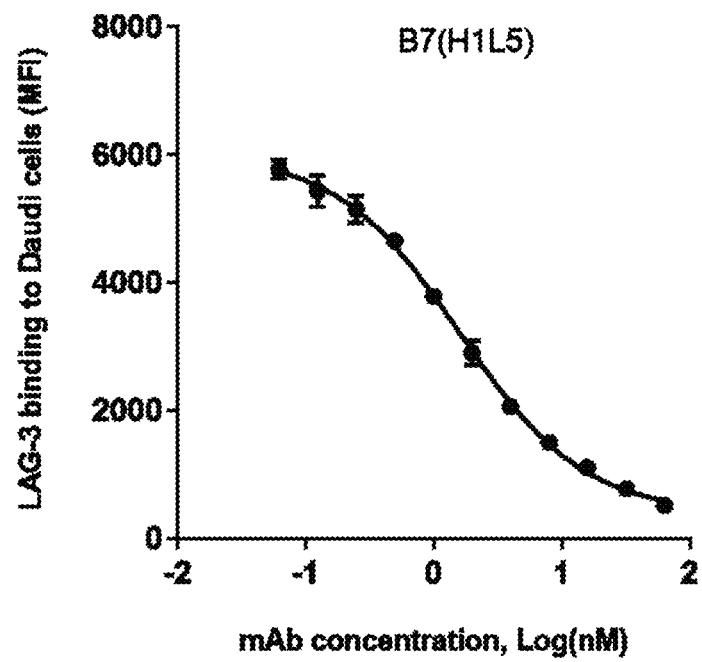
Figure 10C:
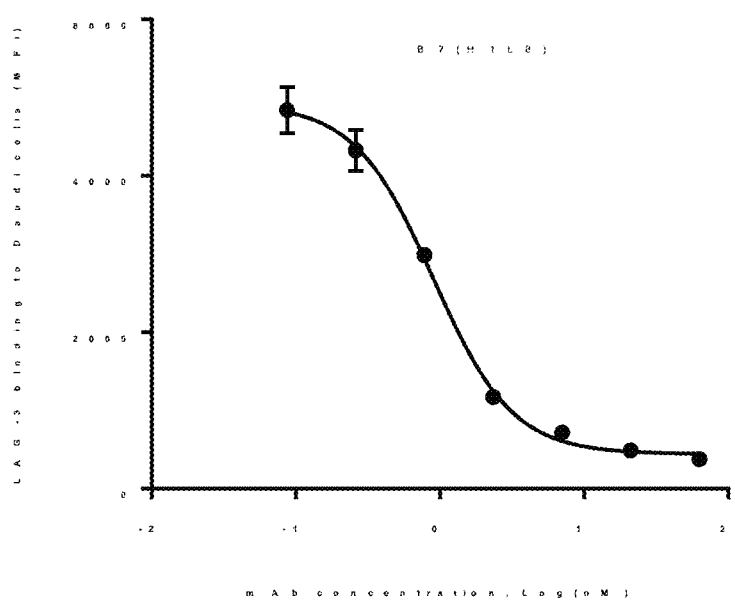

The mouse anti-hLAG-3 mAbs B5 and B7 were humanized to reduce the potential of immunogenicity when used in human patients. The CDRs in both the heavy and light chains of the mouse mAb were grafted into human framework that have the highest possibility of maintaining the proper structure required for antigen binding. Backmutations from human reside to mouse residue were designed when necessary. The sequences of the humanized VH and VL regions are shown in Table 11 and Table 12, respectively. The humanized VH and VL regions were fused to the constant regions of human IgG4 heavy chain and kappa light chain, respectively, to generate humanized mAbs. Constructs corresponding to the mAb sequences were used for transient transfection in 293E cells. Purified mAbs were analyzed for their ability to inhibit hLAG-3 binding to MHC class II molecules on Daudi cells. The $IC_{50}$ values for humanized mAbs are shown in Table 13; several representative $IC_{50}$ curves are shown in FIGS. 10A, 10B, and 10.

TABLE 11

Sequences of heavy chain variable regions of humanized B5 and B7

| Design | VH |
|---|---|
| B5/H1 | QVQLVQSGAEVKKPGASVKMSCKASGYTFTGYYMNWVRQAPGQSLEWLGVI NPYNGDTAYNRKFKGRVTLTVDKSTSTVYMELSSLRSEDTAVYYCARDDGYH VRFFDVWGQGTTVTVSS (SEQ ID NO: 195) |
| B5/H2 | QVQLVQSGAEVKKPGASVKMSCKASGYTFTGYYMNWMRQAPGQSLEWLGVI NPYNGDTAYNRKFKGRVTLTVDKSTSTAYMELSSLRSEDTAVYYCARDDGYH VRFFDVWGQGTTVTVSS (SEQ ID NO: 196) |
| B5H3 | QVQLVQSGAVVKKPGASVKMSCKASGYTFTGYYMNWMRQAPGQSLEWLAVI NPYNGDTAYNRKFKGRATLTVDKSTSTAYMELSSLRSEDTAVYYCARDDGYH VRFFDVWGQGTTVTVSS (SEQ ID NO: 197) |
| B5/H4 | QVQLRQSGAVVKKPGASVKMSCKASGYTFTGYYMNWMRQAHGQSLEWLAV INPYNGDTAYNRKFKGRATLTVDKSTSTAYMELSSLRSEDTAVYYCVRDDGY HVRFFDVWGQGTTVTVSS (SEQ ID NO: 198) |
| B7/H1 | EVQLVQSGAEVKKPGASVKVSCKASGYTFSDYNLNWVRQAPGQGLEWMGLI NLDSAATVYNQKFKGRVTMTRDTSTSTVYMELSSLRSEDTAVYYCASYDYWG QGTLVTVSS (SEQ ID NO: 199) |
| B7/H2 | EVQLVQSGAEVKKPGASVKVSCKASGYTFSDYNLNWVRQAPGQTLEWMGLIN LDSAATVYNQKFKGRVTMTRDTSTSTVYMELSSLRSEDTAVYYCASYDYWGQ GTLVTVSS (SEQ ID NO: 200) |
| B7/H3 | EVQLVQSGAEVKKPGASVKVSCKASGYTFSDYNLNWVRQAPGQGLEWMGLI NLDSAATVYNQKFKGKATMTRDTSTSTVYMELSSLRSEDTAVYYCASYDYWG QGTLVTVSS (SEQ ID NO: 201) |
| B7/H4 | EVQLVQSGAEVKKPGASVKVSCKASGYTFSDYNLNWVRQAPGQTLEWMGLIN LDSAATVYNQKFKGKATMTRDQSTSTAYMELSSLRSEDTAVYYCASYDYWG QGTLVTVSS (SEQ ID NO: 202) |
| B7/H5 | EVQLVQSGAEVKKPGASVKVSCKASGYSFSDYNLNWVRQAPGQTLEWMGLIN LDSAATVYNQKFKGKATMTIDQSTSTAYMELSSLRSEDTAVYYCASYDYWGQ GTLVTVSS (SEQ ID NO: 203) |
| B7/H6 | EFQLVQSGAEVKKPGASVKVSCKASGYSFSDYNLNWVRQAPGQTLEWMGLIN LDSAATVYNQKFKGKATMTIDQSTSTAYMELSSLRSEDTAVYYCASYDYWGQ GTLVTVSS (SEQ ID NO: 204) |

VH: heavy chain variable region

TABLE 12

Sequences of light chain variable regions of humanized B5 and B7

| Design | VL |
|---|---|
| B5/L1 | DIQMTQSPSSLSASVGDRVTITCRSSQDISDYLSWLQQKPGGAPKSLIYSTSTLDS<br>GVPSRFSGSRSGTDFTLTISSLQPEDFATYYCLQYASSPPTFGGGTKVEIK (SEQ ID NO: 205) |
| B5/L2 | DIQMTQSPSSLSASVGDRVTITCRSSQDISDYLSWLQQKPGGAIKSLIYSTSTLDS<br>GVPSRFSGSRSGTDFTLTISSLQPEDFATYYCLQYASSPPTFGGGTKVEIK (SEQ ID NO: 206) |
| B5/L3 | DIQMTQSPSSLSASVGDRVTITCRSSQDISDYLSWLQQKPGGAIKSLIYSTSTLDS<br>GVPSRFSGSRSGTDYTLTISSLQPEDFATYYCLQYASSPPTFGGGTKVEIK (SEQ ID NO: 207) |
| B5/L4 | DIQMTQSPSSLSASVGDRVTITCRSSQDISDYLSWLQQKPGGAIKRLIYSTSTLDS<br>GVPKRFSGSRSGSDYTLTISSLQPEDFATYYCLQYASSPPTFGGGTKVEIK (SEQ ID NO: 208) |
| B7/L5 | DIQMTQSPSSLSASVGDRVTITCRASQDISHYLNWFQQKPGKAPKLLIYETSTLD<br>FGVPSRFSGSGSGTDFTFTISSLQPEDIATYYCLQYATYPLTFGGGTKVEIK (SEQ ID NO: 209) |
| B7/L8 | DIQMTQSPSSLSASVGDRVTITCRASQDISHYLNWFQQKPGKAPKRLIYETSTLD<br>FGVPSRFSGSGSGTDFTFTISSLQPEDIATYYCLQYATYPLTFGGGTKVEIK (SEQ ID NO: 210) |

TABLE 13

IC$_{50}$ values for anti-LAG-3 mAbs in LAG-3/Daudi cell binding assay

| mAb ID | IC50 (nM) |
|---|---|
| B5(H1L4) | 0.98 |
| B5(H2L2) | 1.59 |
| B5(H3L1) | 6.77 |
| B5(H3L2) | 2.85 |
| B5(H3L3) | 2.91 |
| B5(H4L1) | 5.32 |
| B7(H1L5) | 1.59 |
| B7(H2L5) | 1.59 |
| B7(H3L5) | 4.18 |
| B7(H4L5) | 1.35 |
| B7(H5L5) | 0.28 |
| B7(H6L5) | 0.78 |
| B7(H1L8) | 0.90 |
| B7(H2L8) | 0.74 |
| B7(H3L8) | 0.66 |
| B7(H4L8) | 0.70 |
| B7(H5L8) | 0.72 |
| B7(H6L8) | 1.19 |

B5(H1L4) refers to the mAb with the B5/H1 heavy chain and the B5/L4 light chain; all the other humanized mAbs in the table adopt the same naming rule.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated monoclonal antibody or antigen-binding fragment thereof comprising a heavy chain variable region comprising a heavy chain complementarity determining region 1 (HCDR1), HCDR2, HCDR3, and a light chain variable region comprising a light chain complementarity determining region 1 (LCDR1), LCDR2, and LCDR3, having the polypeptide sequences of:
   a. SEQ ID NOs:35, 36, 37, 86, 87, and 88, respectively;
   b. SEQ ID NOs:38, 39, 40, 89, 90, and 91, respectively;
   c. SEQ ID NOs:41, 42, 137, 138, 93, and 94, respectively;
   d. SEQ ID NOs:139, 140, 141, 142, 99, and 143, respectively;
   e. SEQ ID NOs:144, 145, 146, 147, 148, and 149, respectively;
   f. SEQ ID NOs:65, 66, 67, 116, 117, and 118, respectively;
   g. SEQ ID NOs:68, 69, 70, 119, 120, and 121, respectively;
   h. SEQ ID NOs:71, 72, 73, 122, 123, and 124, respectively;
   i. SEQ ID NOs:74, 75, 76, 125, 126, and 127, respectively;
   j. SEQ ID NOs:77, 78, 79, 128, 129, and 130, respectively; or
   k. SEQ ID NOs:80, 150, 151, 131, 132, and 133, respectively;
   l. SEQ ID NOs:68, 69, 70, 119, 120, and 121, respectively;
   m. SEQ ID NOs:71, 72, 73, 122, 123, and 124, respectively;
   n. SEQ ID NOs:74, 75, 76, 125, 126, and 127, respectively;
   o. SEQ ID NOs:77, 78, 79, 128, 129, and 130, respectively;
   p. SEQ ID NOs: 80, 81, 82, 131, 132, and 133, respectively; or
   q. SEQ ID NOs: 83, 84, 85, 134, 135, and 136, respectively;
wherein the antibody or antigen-binding fragment thereof specifically binds LAG-3.

2. The isolated monoclonal antibody or antigen-binding fragment thereof of claim 1, comprising:
   a. a heavy chain variable region having a polypeptide sequence at least 95% identical to SEQ ID NO:1, and a light chain variable region having a polypeptide sequence at least 95% identical to SEQ ID NO:2;
   b. a heavy chain variable region having a polypeptide sequence at least 95% identical to SEQ ID NO:3, and a light chain variable region having a polypeptide sequence at least 95% identical to SEQ ID NO:4;
   c. a heavy chain variable region having a polypeptide sequence at least 95% identical to SEQ ID NO:5, and a light chain variable region having a polypeptide sequence at least 95% identical to SEQ ID NO:6;
   d. a heavy chain variable region having a polypeptide sequence at least 95% identical to SEQ ID NO:7, and a light chain variable region having a polypeptide sequence at least 95% identical to SEQ ID NO:8;
   e. a heavy chain variable region having a polypeptide sequence at least 95% identical to SEQ ID NO:9, and a light chain variable region having a polypeptide sequence at least 95% identical to SEQ ID NO:10;
   f. a heavy chain variable region having a polypeptide sequence at least 95% identical to SEQ ID NO:11, and a light chain variable region having a polypeptide sequence at least 95% identical to SEQ ID NO:12;
   g. a heavy chain variable region having a polypeptide sequence at least 95% identical to SEQ ID NO:13, and a light chain variable region having a polypeptide sequence at least 95% identical to SEQ ID NO:14;
   h. a heavy chain variable region having a polypeptide sequence at least 95% identical to SEQ ID NO:15, and a light chain variable region having a polypeptide sequence at least 95% identical to SEQ ID NO:16;
   i. a heavy chain variable region having a polypeptide sequence at least 95% identical to SEQ ID NO:17, and a light chain variable region having a polypeptide sequence at least 95% identical to SEQ ID NO:18;
   j. a heavy chain variable region having a polypeptide sequence at least 95% identical to SEQ ID NO:19, and a light chain variable region having a polypeptide sequence at least 95% identical to SEQ ID NO:20;
   k. a heavy chain variable region having a polypeptide sequence at least 95% identical to SEQ ID NO:21, and a light chain variable region having a polypeptide sequence at least 95% identical to SEQ ID NO:22;
   l. a heavy chain variable region having a polypeptide sequence at least 95% identical to SEQ ID NO:23, and a light chain variable region having a polypeptide sequence at least 95% identical to SEQ ID NO:24;
   m. a heavy chain variable region having a polypeptide sequence at least 95% identical to SEQ ID NO:25, and a light chain variable region having a polypeptide sequence at least 95% identical to SEQ ID NO:26;
   n. a heavy chain variable region having a polypeptide sequence at least 95% identical to SEQ ID NO:27, and a light chain variable region having a polypeptide sequence at least 95% identical to SEQ ID NO:28;
   o. a heavy chain variable region having a polypeptide sequence at least 95% identical to SEQ ID NO:29, and a light chain variable region having a polypeptide sequence at least 95% identical to SEQ ID NO:30;
   p. a heavy chain variable region having a polypeptide sequence at least 95% identical to SEQ ID NO:31, and a light chain variable region having a polypeptide sequence at least 95% identical to SEQ ID NO:32;

q. a heavy chain variable region having a polypeptide sequence at least 95% identical to SEQ ID NO:33, and a light chain variable region having a polypeptide sequence at least 95% identical to SEQ ID NO:34;
r. a heavy chain variable region having a polypeptide sequence at least 95% identical to SEQ ID NO:195, and a light chain variable region having a polypeptide sequence at least 95% identical to SEQ ID NO:208;
s. a heavy chain variable region having a polypeptide sequence at least 95% identical to SEQ ID NO:196, and a light chain variable region having a polypeptide sequence at least 95% identical to SEQ ID NO:206;
t. a heavy chain variable region having a polypeptide sequence at least 95% identical to SEQ ID NO:197, and a light chain variable region having a polypeptide sequence at least 95% identical to SEQ ID NO:205;
u. a heavy chain variable region having a polypeptide sequence at least 95% identical to SEQ ID NO:197, and a light chain variable region having a polypeptide sequence at least 95% identical to SEQ ID NO:206;
v. a heavy chain variable region having a polypeptide sequence at least 95% identical to SEQ ID NO:197, and a light chain variable region having a polypeptide sequence at least 95% identical to SEQ ID NO:207;
w. a heavy chain variable region having a polypeptide sequence at least 95% identical to SEQ ID NO:198, and a light chain variable region having a polypeptide sequence at least 95% identical to SEQ ID NO:205;
x. a heavy chain variable region having a polypeptide sequence at least 95% identical to SEQ ID NO:199, and a light chain variable region having a polypeptide sequence at least 95% identical to SEQ ID NO:209;
y. a heavy chain variable region having a polypeptide sequence at least 95% identical to SEQ ID NO:200, and a light chain variable region having a polypeptide sequence at least 95% identical to SEQ ID NO:209;
z. a heavy chain variable region having a polypeptide sequence at least 95% identical to SEQ ID NO:201, and a light chain variable region having a polypeptide sequence at least 95% identical to SEQ ID NO:209;
aa. a heavy chain variable region having a polypeptide sequence at least 95% identical to SEQ ID NO:202, and a light chain variable region having a polypeptide sequence at least 95% identical to SEQ ID NO:209;
bb. a heavy chain variable region having a polypeptide sequence at least 95% identical to SEQ ID NO:203, and a light chain variable region having a polypeptide sequence at least 95% identical to SEQ ID NO:209;
cc. a heavy chain variable region having a polypeptide sequence at least 95% identical to SEQ ID NO:204, and a light chain variable region having a polypeptide sequence at least 95% identical to SEQ ID NO:209;
dd. a heavy chain variable region having a polypeptide sequence at least 95% identical to SEQ ID NO:199, and a light chain variable region having a polypeptide sequence at least 95% identical to SEQ ID NO:210;
ee. a heavy chain variable region having a polypeptide sequence at least 95% identical to SEQ ID NO:200, and a light chain variable region having a polypeptide sequence at least 95% identical to SEQ ID NO:210;
ff. a heavy chain variable region having a polypeptide sequence at least 95% identical to SEQ ID NO:201, and a light chain variable region having a polypeptide sequence at least 95% identical to SEQ ID NO:210;
gg. a heavy chain variable region having a polypeptide sequence at least 95% identical to SEQ ID NO:202, and a light chain variable region having a polypeptide sequence at least 95% identical to SEQ ID NO:210;
hh. a heavy chain variable region having a polypeptide sequence at least 95% identical to SEQ ID NO:203, and a light chain variable region having a polypeptide sequence at least 95% identical to SEQ ID NO:210; or
ii. a heavy chain variable region having a polypeptide sequence at least 95% identical to SEQ ID NO:204, and a light chain variable region having a polypeptide sequence at least 95% identical to SEQ ID NO:210.

3. The isolated monoclonal antibody or antigen-binding fragment thereof of claim 1, comprising:
a. a heavy chain variable region having the polypeptide sequence of SEQ ID NO:1, and a light chain variable region having the polypeptide sequence of SEQ ID NO:2;
b. a heavy chain variable region having the polypeptide sequence of SEQ ID NO:3, and a light chain variable region having the polypeptide sequence of SEQ ID NO:4;
c. a heavy chain variable region having the polypeptide sequence of SEQ ID NO:5, and a light chain variable region having the polypeptide sequence of SEQ ID NO:6;
d. a heavy chain variable region having the polypeptide sequence of SEQ ID NO:7, and a light chain variable region having the polypeptide sequence of SEQ ID NO:8;
e. a heavy chain variable region having the polypeptide sequence of SEQ ID NO:9, and a light chain variable region having the polypeptide sequence of SEQ ID NO:10;
f. a heavy chain variable region having the polypeptide sequence of SEQ ID NO:11, and a light chain variable region having the polypeptide sequence of SEQ ID NO:12;
g. a heavy chain variable region having the polypeptide sequence of SEQ ID NO:13, and a light chain variable region having the polypeptide sequence of SEQ ID NO:14;
h. a heavy chain variable region having the polypeptide sequence of SEQ ID NO:15, and a light chain variable region having the polypeptide sequence of SEQ ID NO:16;
i. a heavy chain variable region having the polypeptide sequence of SEQ ID NO:17, and a light chain variable region having the polypeptide sequence of SEQ ID NO:18;
j. a heavy chain variable region having the polypeptide sequence of SEQ ID NO:19, and a light chain variable region having the polypeptide sequence of SEQ ID NO:20;
k. a heavy chain variable region having the polypeptide sequence of SEQ ID NO:21, and a light chain variable region having the polypeptide sequence of SEQ ID NO:22;
l. a heavy chain variable region having the polypeptide sequence of SEQ ID NO:23, and a light chain variable region having the polypeptide sequence of SEQ ID NO:24;
m. a heavy chain variable region having the polypeptide sequence of SEQ ID NO:25, and a light chain variable region having the polypeptide sequence of SEQ ID NO:26;

n. a heavy chain variable region having the polypeptide sequence of SEQ ID NO:27, and a light chain variable region having the polypeptide sequence of SEQ ID NO:28;

o. a heavy chain variable region having the polypeptide sequence of SEQ ID NO:29, and a light chain variable region having the polypeptide sequence of SEQ ID NO:30;

p. a heavy chain variable region having the polypeptide sequence of SEQ ID NO:31, and a light chain variable region having the polypeptide sequence of SEQ ID NO:32;

q. a heavy chain variable region having the polypeptide sequence of SEQ ID NO:33, and a light chain variable region having the polypeptide sequence of SEQ ID NO:34;

r. a heavy chain variable region having the polypeptide sequence of SEQ ID NO:195, and a light chain variable region having the polypeptide sequence of SEQ ID NO:208;

s. a heavy chain variable region having the polypeptide sequence of SEQ ID NO:196, and a light chain variable region having the polypeptide sequence of SEQ ID NO:206;

t. a heavy chain variable region having the polypeptide sequence of SEQ ID NO:197, and a light chain variable region having the polypeptide sequence of SEQ ID NO:205;

u. a heavy chain variable region having the polypeptide sequence of SEQ ID NO:197, and a light chain variable region having the polypeptide sequence of SEQ ID NO:206;

v. a heavy chain variable region having the polypeptide sequence of SEQ ID NO:197, and a light chain variable region having the polypeptide sequence of SEQ ID NO:207;

w. a heavy chain variable region having the polypeptide sequence of SEQ ID NO:198, and a light chain variable region having the polypeptide sequence of SEQ ID NO:205;

x. a heavy chain variable region having the polypeptide sequence of SEQ ID NO:199, and a light chain variable region having the polypeptide sequence of SEQ ID NO:209;

y. a heavy chain variable region having the polypeptide sequence of SEQ ID NO:200, and a light chain variable region having the polypeptide sequence of SEQ ID NO:209;

z. a heavy chain variable region having the polypeptide sequence of SEQ ID NO:201, and a light chain variable region having the polypeptide sequence of SEQ ID NO:209;

aa. a heavy chain variable region having the polypeptide sequence of SEQ ID NO:202, and a light chain variable region having the polypeptide sequence of SEQ ID NO:209;

bb. a heavy chain variable region having the polypeptide sequence of SEQ ID NO:203, and a light chain variable region having the polypeptide sequence of SEQ ID NO:209;

cc. a heavy chain variable region having the polypeptide sequence of SEQ ID NO:204, and a light chain variable region having the polypeptide sequence of SEQ ID NO:209;

dd. a heavy chain variable region having the polypeptide sequence of SEQ ID NO:199, and a light chain variable region having the polypeptide sequence of SEQ ID NO:210;

ee. a heavy chain variable region having the polypeptide sequence of SEQ ID NO:200, and a light chain variable region having the polypeptide sequence of SEQ ID NO:210;

ff. a heavy chain variable region having the polypeptide sequence of SEQ ID NO:201, and a light chain variable region having the polypeptide sequence of SEQ ID NO:210;

gg. a heavy chain variable region having the polypeptide sequence of SEQ ID NO:202, and a light chain variable region having the polypeptide sequence of SEQ ID NO:210;

hh. a heavy chain variable region having the polypeptide sequence of SEQ ID NO:203, and a light chain variable region having the polypeptide sequence of SEQ ID NO:210; or ii. a heavy chain variable region having the polypeptide sequence of SEQ ID NO:204, and a light chain variable region having the polypeptide sequence of SEQ ID NO:210.

4. The isolated monoclonal antibody or antigen-binding fragment thereof of claim 1, wherein the isolated monoclonal antibody or antigen-binding fragment thereof specifically binds to an epitope comprising an amino acid sequence selected from the group consisting of SEQ ID NO:192, SEQ ID NO:193, SEQ ID NO:158, SEQ ID NO:180, and SEQ ID NO:194.

5. The isolated monoclonal antibody or antigen-binding fragment thereof of claim 1, wherein the monoclonal antibody or antigen-binding fragment thereof inhibits LAG-3 activity and/or is capable of blocking binding to LAG-3 to MHC class II molecules.

6. The isolated monoclonal antibody or antigen-binding fragment thereof of claim 1, wherein the antibody or antigen-binding fragment thereof is chimeric and/or human or humanized.

7. The isolated monoclonal antibody or antigen-binding fragment thereof of claim 1, wherein the monoclonal antibody or antigen-binding fragment thereof specifically binds human LAG-3.

8. A pharmaceutical composition comprising the isolated monoclonal antibody or antigen-binding fragment thereof of claim 1 and a pharmaceutically acceptable carrier.

9. A method of producing a pharmaceutical composition comprising
the monoclonal antibody or antigen-binding fragment of claim 1, comprising combining the monoclonal antibody or antigen-binding fragment with a pharmaceutically acceptable carrier to obtain the pharmaceutical composition.

10. A bispecific antibody comprising the monoclonal antibody or antigen-binding fragment thereof of claim 1.

11. An isolated nucleic acid encoding the monoclonal antibody or antigen-binding fragment thereof of claim 1.

12. A vector comprising the isolated nucleic acid of claim 11.

13. A host cell comprising the vector of claim 12.

14. A method of producing the monoclonal antibody or antigen-binding fragment thereof of claim 1, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

15. A method of determining a level of LAG-3 in a subject, the method comprising:
   a. obtaining a sample from the subject;
   b. contacting the sample with an isolated monoclonal antibody or antigen-binding fragment thereof of claim 1; and
   c. determining a level of LAG-3 in the subject.

16. The method of claim 15, wherein the sample is a tissue sample or a blood sample.

17. The method of claim 16, wherein the tissue sample is a cancer tissue sample.

* * * * *